US007910107B2

(12) United States Patent
Walsh et al.

(10) Patent No.: US 7,910,107 B2
(45) Date of Patent: Mar. 22, 2011

(54) ANTAGONIST ANTIBODIES AGAINST GDF-8 AND USES IN TREATMENT OF ALS AND OTHER GDF-8 ASSOCIATED DISORDERS

(75) Inventors: Frank S. Walsh, Bryn Mawr, PA (US); Margaret M. Zaleska, Narberth, PA (US); David S. Howland, Yardley, PA (US); Erika L. F. Holzbaur-Howland, Yardley, PA (US); Lioudmila Tchistiakova, Andover, MA (US); Riyez Karim, North Andover, MA (US); Pamela Kelley, Reading, MA (US); William Kelley, legal representative, Reading, MA (US); Xiang-Yang Tan, Reading, MA (US); Seung Poon Kwak, Ewing, NJ (US); Karen Wallace, Newton Square, PA (US); Nicholas Weber, Mountaintop, PA (US); Menelas N. Pangalos, Pennington, NJ (US)

(73) Assignees: WYETH LLC, Wilmington, DE (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/508,618

(22) Filed: Jul. 24, 2009

(65) Prior Publication Data

US 2009/0285827 A1 Nov. 19, 2009

Related U.S. Application Data

(62) Division of application No. 11/503,062, filed on Aug. 14, 2006.

(60) Provisional application No. 60/709,704, filed on Aug. 19, 2005.

(51) Int. Cl.
A61K 39/395 (2006.01)
(52) U.S. Cl. ............... 424/145.1; 424/130.1; 424/133.1
(58) Field of Classification Search .................. None
See application file for complete search history.

(56) References Cited

U.S. PATENT DOCUMENTS

| | | | |
|---|---|---|---|
| 5,624,821 A | 4/1997 | Winter et al. |
| 5,648,260 A | 7/1997 | Winter et al. |
| 5,951,974 A | 9/1999 | Gilbert et al. |
| 6,030,613 A | 2/2000 | Blumberg et al. |
| 6,096,506 A | 8/2000 | Lee et al. |
| 6,102,035 A | 8/2000 | Asking et al. |
| 6,102,454 A | 8/2000 | Weyerstall |
| 6,407,213 B1 | 6/2002 | Carter et al. |
| 6,465,239 B1 | 10/2002 | Lee et al. |
| 6,607,884 B1 | 8/2003 | Lee et al. |
| 6,673,534 B1 | 1/2004 | Lee et al. |
| 6,891,082 B2 | 5/2005 | Lee et al. |
| 7,192,717 B2 | 3/2007 | Hill et al. |
| 7,261,893 B2 | 8/2007 | Veldman et al. |
| 7,320,789 B2 | 1/2008 | Aghajanian et al. |
| 7,381,528 B2 | 6/2008 | Lee et al. |
| 7,393,682 B1 | 7/2008 | Lee et al. |
| 2002/0127234 A1 | 9/2002 | El Halawani et al. |
| 2002/0157125 A1 | 10/2002 | Lee et al. |
| 2003/0074680 A1 | 4/2003 | Lee et al. |
| 2003/0118592 A1 | 6/2003 | Ledbetter et al. |
| 2003/0133939 A1 | 7/2003 | Ledbetter et al. |
| 2003/0138422 A1 | 7/2003 | Aghajanian et al. |
| 2004/0055027 A1 | 3/2004 | Lee et al. |
| 2004/0058445 A1 | 3/2004 | Ledbetter et al. |
| 2004/0142382 A1 | 7/2004 | Veldman et al. |
| 2005/0014733 A1 | 1/2005 | Whittemore et al. |
| 2005/0136049 A1 | 6/2005 | Ledbetter et al. |
| 2005/0175614 A1 | 8/2005 | Ledbetter et al. |
| 2005/0180970 A1 | 8/2005 | Ledbetter et al. |
| 2005/0186216 A1 | 8/2005 | Ledbetter et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2005/0257278 A1 | 11/2005 | Lee et al. |
| 2006/0240487 A1 | 10/2006 | Nowak et al. |
| 2006/0240488 A1 | 10/2006 | Nowak et al. |
| 2008/0178310 A1 | 7/2008 | Lee et al. |
| 2008/0213426 A1 | 9/2008 | Lee et al. |

FOREIGN PATENT DOCUMENTS

EP 1411064 A2 4/2004

(Continued)

OTHER PUBLICATIONS

The Merck Manuals Online Medical Library, [online]. Whitehouse Station, NJ: Merck Research Laboratories, 2006-2007. [retrieved on Mar. 22, 2010]. Retrieved from the Internet: < URL: http://www.merck.com/mmpe/print/sec15/ch199/ch199b.html>. Anorexia Nervosa: East Disorders Shock. see pp. 1-4.*
Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*

(Continued)

*Primary Examiner* — Sharon Wen
(74) *Attorney, Agent, or Firm* — Finnegan, Henderson, Farabow, Garrett & Dunner, L.L.P.

(57) ABSTRACT

The disclosure provides novel molecules related to growth and differentiation factor-8 (GDF-8), in particular mouse and humanized antibodies, and antibody fragments, including those that inhibit GDF-8 activity and signaling in vitro and/or in vivo. The disclosure also provides methods for diagnosing, treating, ameliorating, preventing, prognosing, or monitoring degenerative orders of muscle, bone, and insulin metabolism, etc., in particular amyotrophic lateral sclerosis (ALS). In addition, the disclosure provides pharmaceutical compositions for the treatment of such disorders by using the antibodies, polypeptides, polynucleotides, and vectors of the invention.

14 Claims, 16 Drawing Sheets

FOREIGN PATENT DOCUMENTS

| WO | WO 94/21681 | 9/1994 |
|---|---|---|
| WO | WO 96/33735 | 10/1996 |
| WO | WO 96/34015 | 10/1996 |
| WO | WO 96/34096 | 10/1996 |
| WO | WO 97/10847 | 3/1997 |
| WO | WO 98/33887 | 8/1998 |
| WO | WO 99/02667 | 1/1999 |
| WO | WO 99/06559 | 2/1999 |
| WO | WO 99/24618 | 5/1999 |
| WO | WO 99/40181 | 8/1999 |
| WO | WO 00/43781 | 7/2000 |
| WO | WO 01/05820 | 1/2001 |
| WO | WO 03/072714 | 9/2003 |
| WO | WO 03/072715 | 9/2003 |
| WO | WO 2004/037861 | 5/2004 |
| WO | WO 2004/039948 | 5/2004 |
| WO | WO 2004/108157 | 12/2004 |
| WO | WO 2006/102574 | 9/2006 |
| WO | WO 2006/107611 | 10/2006 |

OTHER PUBLICATIONS

Al-Lazikani et al. (1997) "Standard Conformations for the Canonical Structures of Immunoglobulins," *J. Mol. Biol.* 273:927-48.

Alfarano et al. (2005) "The Biomolecular Interaction Network Database and related tools 2005 update," *Nuc. Acids Res.* Database Issue 33:D418-24.

Attwood (2000) "Genomics: The Babel of Bioinformatics," *Science* 290:471-473.

Azzouz et al. (2004) "VEGF delivery with retrogradely transported lentivector prolongs survival in a mouse ALS model," *Nature* 429:413-17.

Bellinge et al. (2005) "Myostatin and Its Implications on animal breeding: a review," *Animal Genetics* 36:1-6.

Bendig Methods: A Companion to Methods in Enzymology 8:83-93 (1995).

Bogdanovich et al. (2002) "Functional improvement of dystrophic muscle by myostatin blockade," *Nature* 420:418-21.

Brown et al. (1999) "Physicochemical Activation of Recombinant Latent Transforming Growth Factor-beta's 1, 2, and 3," *Growth Factors* 3:35-43.

Bruijn et al. (2004) "Unraveling the Mechanisms Involved in Motor Neuron Degeneration in ALS," *Annu. Rev. Neurosci.* 27:723-49.

Casas et al. (1998) "Association of the Muscle Hypertrophy Locus with Carcass Traits in Beef Cattle," *J. Anim. Sci.* 76:468-473.

Chao (2003) "Retrograde Transport Redux" *Neuron* 39:1-2.

Clement et al. (2003) "Wild-Type Nonneuronal Cells Extend Survival of SOD1 Mutant Motor Neurons in ALS Mice," *Science* 302:113-17.

Davis et al. (2005) "Crystal structure of prostate-specific membrane antigen, a tumor marker and peptidase," *Proc. Natl. Acad. Sci. USA* 102:5981-86.

Dennler et al. (1998) "Direct binding of Smad3 and Smad4 to critical TGFβ-inducible elements in the promoter of human plasminogen activator inhibitor-type 1 gene," *EMBO J.* 17:3091-3100.

Dickman, Steven (1997) "Gene Mutation Provides More Meat on the Hoof," *Science* 277:1922-1923.

Dobrowolny et al. (2005) "Muscle expression of a local Igf-1 isoform protects motor neurons in an ALS mouse model," *J. Cell Biol.* 168:193-99.

Downer, J. (2002) "New, Better Rat Model Reveals Astrocyte Role in ALS," *UniSci* (3 pgs.) Jan. 30, 2002 http://www.unisci.com/stories/20021/0130021.htm printed Nov. 19, 2007.

Dunlop et al. (2003) "Impaired Spinal Cord Glutamate Transport Capacity and Reduced Sensitivity to Riluzole in a Transgenic Superoxide Dismutase Mutant Rat Model of Amyotrophic Lateral Sclerosis," *J. Neurosci.* 23:1688-96.

Dupuis et al. (2004) "Evidence for defective energy homeostasis in amyotrophic lateral sclerosis: Benefit of a high-energy diet in a transgenic mouse model," *Proc. Natl. Acad. Sci. U.S.A.* 101:11159-64.

Fischer et al. (2004) "Amyotrophic lateral sclerosis is a distal axonopathy: evidence in mice and man," *Exp. Neurol.* 185:232-40.

Frev et al. (2000) "Early and Selective Loss of Neuromuscular Synapse Subtypes with Low Sprouting Competence in Motoneuron Diseases," *J. Neurosci.* 20:2534-42.

Gamer et al. (1999) "A Novel BMP Expressed in Developing Mouse Limb, Spinal Cord, and Tail Bud Is a Potent Mesoderm Inducer in Xenopus Embryos," *Dev. Biol.* 208:222-32.

Gardlik et al. (2005) "Vectors and delivery systems in gene therapy," *Med. Sci. Monit.* 11:RA110-21.

Gonzalez-Cadavid et al. (1998) "Organization of the human myostatin gene and expression in healthy men and HIV-infected men with muscle wasting," *Proc. Natl. Acad. Sci. U.S.A.* 95:14938-43.

Grobet et al. (1997) "A Deletion in the Bovine Myostatin Gene Causes the Double-Muscled Phenotype in Cattle," *Nature Genetics* 17:71-74.

Guo et al. (2003) "Increased expression of the glial glutamate transporter EAAT2 modulates excitotoxicity and delays the onset but not the outcome of ALS in mice," *Hum. Mol. Genet.* 12:2519-32.

Halpin and Harbury (2004) "DNA Display II. Genetic Manipulation of Combinatorial Chemistry Libraries for Small-Molecule Evolution," *PLoS Biology* 2:1022-30.

Hamrick et al. (2000) "Femoral Morphology and Cross-sectional Geometry of Adult Myostatin-Deficient Mice," *Bone* 27:343-49.

Holzbaur (2004) "Motor neurons rely on motor proteins," *Trends Cell Biol.* 14:233-40.

Holzbaur et al. (2006) "Myostatin inhibition slows muscle atrophy in rodent models of amyotrophic lateral sclerosis," *Neurobiol. Dis.* 23:697-707.

Hoodless and Wrana (1998) "Mechanism and Function of Signaling by the TGFβSuperfamily," *Curro Top. Microbiol. Immunol.* 228:235-72.

Howland et al. (2002) "Focal loss of the glutamate transporter EAAT2 in a transgenic rat model of SOD1 mutant-mediated amyotrophic lateral sclerosis (ALS)," *Proc. Natl. Acad. Sci. U.S.A.* 99:1604-09.

Kambadur et al. (1997) "Mutations in myostatin (GDF8) in Double-Muscled Belgian Blue and Piedmontese Cattle," *Genome Res.* 7:910-15.

Karp (2000) "An ontology for biological function based on molecular interactions," *Bioinformatics Ontology* 16:269-85.

Kaspar et al. (2003) "Retrograde Viral Delivery of IGF-1 Prolongs Survival in a Mouse ALS Model," *Science* 301:839-42.

Kieran et al. (2004) "Treatment with arimoclomol, a coinducer of heat shock proteins, delays disease progression in ALS mice," *Nat. Med.* 10:402-05.

Kim et al. (2001) "Inhibition of Preadipocyte Differentiation by Myostatin Treatment in 3T3-L1 Cultures," *Biochem. Biophys. Res. Commun.* 281:902-06.

LaMonte et al. (2002) "Disruption of Dyneinl/Dynactin Inhibits Axonal Transport in Motor Neurons Causing Late-Onset Progressive Degeneration," *Neuron* 34:715-27.

Langley et al. (2002) "Myostatin Inhibits Myoblast Differentiation by Down-Regulating MyoD Expression," *J. Biol. Chem.* 277:49831-40.

Lechtzin et al. (2002) "Amyotrophic lateral sclerosis: evaluation and treatment of respiratory impairment," *Amyotroph. Lateral Seler. Other Motor Neuron Disord.* 3:5-13.

Lee and McPherron (1999) "Myostatin and the control of skeletal muscle mass," *Curr. Opin. Genet. Dev.* 9:604-07.

Ligon et al. (2005) "Mutant superoxide dismutase disrupts cytoplasmic dynein in motor neurons," *Neuro Report* 16:533-36.

McCroskery et al. (2003) "Myostatin negatively regulates satellite cell activation and self-renewal," *J. Cell Biol.* 162:1135-47.

McCroskery et al. (2005) "Improved muscle healing through enhanced regeneration and reduced fibrosis in myostatin-null mice," *J. Cell. Sci.* 118:3531-41.

McKnight, Steven L. (1997) "Gatekeepers of Organ Growth," *Proc. Natl. Acad. Sci. U.S.A.* 94:12249-12250.

McPherron and Lee (1997) "Double muscling in cattle due to mutations in the myostatin gene," *Proc. Natl. Acad. Sci. U.S.A.* 94:12457-61.

McPherron et al. (1997) "Regulation of skeletal muscle mass in mice by a new TGF-β superfamily member," *Nature* 387:83-90.

Mennissier, F. (1982) "Present State of Knowledge About the Genetic Determination of Muscular Hypertrophy or the Double Muscled Trait in Cattle," *Muscle Hypertrophy of Genetic Origin and Its Uses to Improve Beef Production: A Seminar in CEC Programme of Coordinated Research on Beef Production* pp. 387-428.

Molina et al. (1996) "Improved Performances of Spot Multiple Peptide Synthesis," *Peptide Res.* 9:151-55.

Morgan et al. (1995) "The N-terminal end of the $C_H2$ domain of chimeric human IgG1 and anti-HLA-DR is necessary for C1q, FcγR1 and FcγRIII binding," *Immunology* 86:319-24.

Muyldermans (2001) "Single domain camel antibodies: current status," *Rev. Mol. Biotechnol.* 74:277-302.

Muyldermans et al. (2001) "Recognition of antigens by single-domain antibody fragments: the superfluous luxury of paired domains," *Trends Biochem. Sci.* 26:230-35.

Padlan et al. (1989) "Structure of an antibody-antigen complex: crystal structure of the HyHEL-10 Fab-lysozyme complex," *Proc. Natl. Acad. Sci. U.S.A.* 86:5938-5942.

Reaume et al. (1996) "Motor neurons in Cu/Zn superoxide dismutase-deficient mice develop normally but exhibit enhanced cell death after axonal injury," *Nat. Genet.* 13:43-47.

Rudikoff et al. (1982) "Single amino acid substitution altering antigen-binding specificity," *Proc. Natl. Acad. Sci. U.S.A.* 79:1979-1983.

Schier et al. (1996) "Isolation of Picomolar Affinity Anti-c-erbB-2 Single-chain Fv by Molecular Evolution of the Complementarity Determining Regions in the Center of the Antibody Binding Site," *J. Mol. Biol.* 263:551-67.

Schmitz and Hof (2000) "Recommendations for straightforward and rigorous methods of counting neurons based on a computer simulation approach," *J. Chem. Neuroanat.* 20:93-114.

Schmitz and Hof (2005) "Design-based stereology in neuroscience," *Neuroscience* 130:813-31.

Schütz et al. (2005) "The Oral Antidiabetic Pioglitazone Protects from Neurodegeneration and Amyotrophic Lateral Sclerosis-Like Symptoms in Superoxide Dismutase-G93A Transgenic Mice," *J. Neurosci.* 25:7805-12.

Sharp (2005) "The effect of peripheral nerve injury on disease progression in the SOD1(G93A) mouse model of amyotrophic lateral sclerosis," *Neuroscience* 130:897-910.

Shields et al. (2001) "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276:6591-604.

Skolnick et al. (2000) "From genes to protein structure and function: novel applications of computational approaches in the genomic era," *Trends in Biotechnol.* 18:34-39.

The Merck Manuals Online Medical Library, [online]. Whitehouse Station, NJ: Merck Research Laboratories, 2006-2007. [retrieved on Dec. 6, 2007]. Retrieved from the Internet:, URL: http://www.merck.com/mmpe/print/sec16/ch223/ch223f.html>. Motor Neuron Disorders, see pp. 1-4.

Thies et al. (2001) "GDF-8 Propeptide Binds to GDF-8 and Antagonizes Biological Activity by Inhibiting GDF-8 Receptor Binding," *Growth Factors* 18:251-59.

Thomas et al. (2000) "Myostatin, a Negative Regulator of Muscle Growth, Functions by Inhibiting Myoblast Proliferation," *J. Biol. Chem.* 275:40235-43.

Tobin and Celeste (2005) "Myostatin, a negative regulator of muscle mass: implications for muscle degenerative diseases," *Curro Opin. Pharmacol.* 5:328-32.

van den Beucken et al. (2001) "Building Novel Binding Ligands to B7.1 and B7.2 Based on Human Antibody Single Variable Light Chain Domains," *J. Mol. Biol.* 310:591-601.

Verkman (2004) "Drug discovery in academia," *Am. J. Physiol. Cell Physiol.* 286:465-74.

Vukicevic et al. (1996) "Induction of nephrogenic mesenchyme by osteogenic protein 1 (bone morphogenetic protein 7)," *Proc. Natl. Acad. Sci. U.S.A.* 93:9021-9026.

Wagner et al. (2002) "Loss of Myostatin Attenuates Severity of Muscular Dystrophy in mdx Mice," *Ann. Neurol.* 52:832-36.

Wang et al. (2002) "Neuroprotective Effects of Glial Cell Line-Derived Neurotrophic Factor Mediated by an Adeno-Associated Virus Vector in a Transgenic Animal Model of Amyotrophic Lateral Sclerosis," *J. Neurosci.* 22:6920-28.

Ward et al. (1989) "Binding activities of a repertoire of single immunoglobulin variable domains secreted from *Escherichia coli*," *Nature* 341:544-46.

Whittemore et al. (2003) "Inhibition of myostatin in adult mice increases skeletal muscle mass and strength," *Biochem. Biophys. Res. Commun.* 300:965-71.

Wooley et al. (2005) "Gait analysis detects early changes in transgenic SOD1(G93A) mice," *Muscle Nerve* 32:43-50.

Zimmers et al. (2002) "Induction of Cachexia in Mice by Systemically Administered Myostatin," *Science* 296:1486-88.

\* cited by examiner

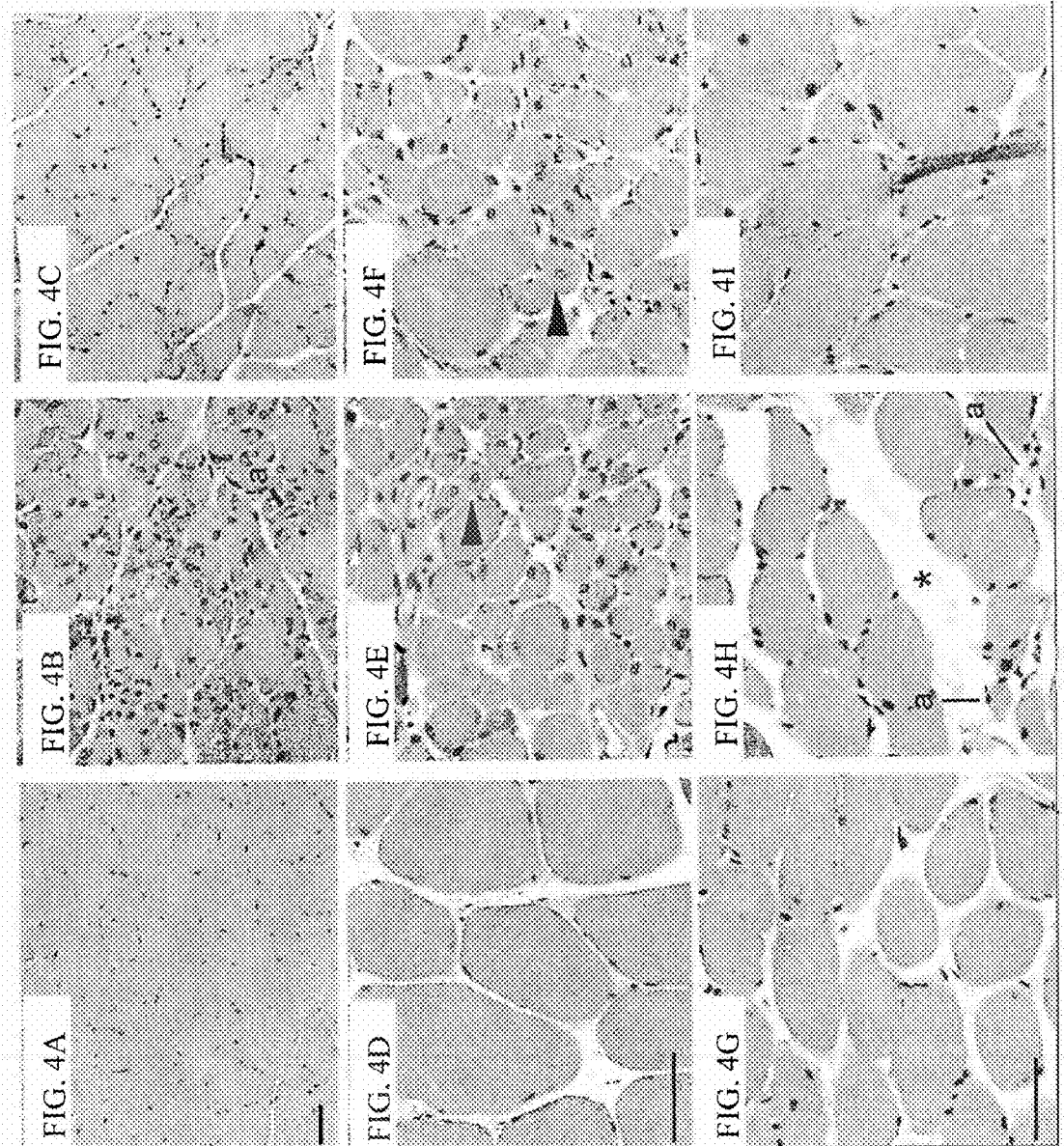

DFGLDCDEHSTESRCCRYPLTVDFEAFGWDWIIAPKRYKANYCSGECEF
VFLQKY
PHTHLVHQANPRGSAGPCCTPTKMSPINMLYFNGKEQIIYGKIPAMVVDR
CGCS

FIG. 7

Alignment of RK35 light chain variable region with DPK9

Identities = 65/95 (68%)

```
MRK35 VL    1   DIEMTQSHKFMSTSVGDRVSITCKASQDVSTAVAWYQQKPGQSPKLLLYSASYRTTGVPD  60
HuRK35 VL   1   DIQMTQSPSSLSASVGDRVTITCKASQDVSTAVAWYQQKPGKAPKLLIYSASYRYTGVPS  60
DPK-9       1   DIQMTQSPSSLSASVGDRVTITCRASQSISSYLNWYQQKPGKAPKLLIYAASSLQSGVPS  60
                   ****** ****   ******   *********          * * **** *    **

MRK35 VL   61   RFTGSGSGTDFTFTISSVQAEDLAVYYCQQHYSTPWTFGGGTKLEIK  107
HuRK35 VL  61   RFSGSGSGTDFTLTISSLQPEDFATYYCQQHYSTPWTFGQGTKVEIK  107
DPK-9      61   RFSGSGSGTDFTLTISSLQPEDFATYYCQQSYSTP              95
                ** ********* *** * ** *****                *
```

20 amino acid substitutions
Potential back-mutations: P80A

Alignment of RK35 heavy chain variable region with DP-47

Identities = 79/98 (80%)

```
mRK35 VH    1   EVQLVESGGGLVKPGGSLKLLSCAASGFTFSSYAMSWVRQTPEKRLEWVATISSGGSYTSY  60
HuRK35 VH   1   EVQLLESGGGLVQPGGSLRLSCAASGFTFSSYAMSWVRQAPGKGLEWVSTISSGGSYTSY  60
DP-47       1   EVQLLESGGGLVQPGGSLRLSCAASGFTFSSYAMSWVRQAPGKGLEWVSAISGSGSTYY  60
                ****  ****** **** * ***************    * * ****  *   *  *

RK35 VH    61   PDSVKGRFTISRDNAKNTLYLQMSSLRSEDTAMYYCARQDYAMNYWGQGTSVTVSS  116
HuRK35 VH  61   PDSVKGRFTISRDNSKNTLYLQMNSLRAEDTAVYYCAKQDYAMNYWGQGTMVTVSS  116
DP-47      61   ADSVKGRFTISRDNSKNTLYLQMNSLRAEDTAVYYCAK                 98
                 ***********   ********  ***  ***** ***
```

13 amino acid substitutions in the framework regions
Potential back-mutations: L5V; G42E, G44R; S49A; V93M

FIG. 8

ANTAGONIST ANTIBODIES AGAINST GDF-8 AND USES IN TREATMENT OF ALS AND OTHER GDF-8 ASSOCIATED DISORDERS

This application is a divisional of U.S. patent application Ser. No. 11/503,062, filed Aug. 14, 2006, which claims the benefit of priority from U.S. Provisional Patent Application 60/709,704, filed Aug. 19, 2005, the contents of which are hereby incorporated by reference herein in their entirety.

STATEMENT REGARDING FEDERALLY SPONSORED RESEARCH

This invention was made with U.S. Government support under grants from the National Institutes of Health (R01 GM-48661 and R01 GM-56707). The Government has certain rights in the invention.

SEQUENCE LISTING

The instant application contains an amended Sequence Listing which has been submitted via EFS-Web and is hereby incorporated by reference in its entirety. Said ASCII copy, created on Jan. 8, 2010, is named 08702021.txt, and is 23,475 bytes in size.

BACKGROUND OF THE INVENTION

1. Field of the Invention

The technical field of the invention relates to growth and differentiation factor-8 (GDF-8) antagonists, in particular, antibodies against GDF-8, e.g., mouse, human and humanized antibodies and their fragments, particularly those that inhibit GDF-8 activity in vitro and/or in vivo. The field further relates to treating, ameliorating, preventing, prognosing, or monitoring GDF-8-associated disorders, e.g., muscle disorders, neuromuscular disorders, bone degenerative disorders, metabolic or induced bone disorders, adipose disorders, glucose metabolism disorders or insulin-related disorders, particularly amyotrophic lateral sclerosis ("ALS").

2. Related Background Art

Growth and differentiation factor-8 (GDF-8), also known as myostatin, is a secreted protein and member of the transforming growth factor-beta (TGF-β) superfamily of structurally related growth factors. Members of this superfamily possess growth-regulatory and morphogenetic properties (Kingsley et al. (1994) *Genes Dev.* 8:133-46; Hoodless et al. (1998) *Curr. Topics Microbiol. Immunol.* 228:235-72). Human GDF-8 is synthesized as a 375 amino acid precursor protein that forms a homodimer complex. During processing, the amino-terminal propeptide, known as the "latency-associated peptide" (LAP), is cleaved and may remain noncovalently bound to the homodimer, forming an inactive complex designated the "small latent complex" (Miyazono et al. (1988) *J. Biol. Chem.* 263:6407-15; Wakefield et al. (1988) *J. Biol. Chem.* 263:7646-54; Brown et al. (1999) *Growth Factors* 3:35-43; Thies et al. (2001) *Growth Factors* 18:251-59; Gentry et al. (1990) *Biochemistry* 29:6851-57; Derynck et al. (1995) *Nature* 316:701-05; Massague (1990) *Ann. Rev. Cell Biol.* 12:597-641). Proteins such as follistatin and its relatives also bind mature GDF-8 homodimers and inhibit GDF-8 biological activity (Garner et al. (1999) *Dev. Biol.* 208:222-32).

An alignment of the deduced GDF-8 amino acid sequence from various species demonstrates that GDF-8 is highly conserved (McPherron et al. (1997) *Proc. Natl. Acad. Sci. U.S.A.* 94:12457-61). The sequences of human, mouse, rat, porcine, and chicken GDF-8 are 100% identical in the C-terminal region, while baboon, bovine, and ovine GDF-8 differ by a mere 3 amino acids at the C-terminus. The high degree of GDF-8 conservation across species suggests that GDF-8 has an essential physiological function.

GDF-8 has been shown to play a major role in the regulation of muscle development and homeostasis by inhibiting both proliferation and differentiation of myoblasts and satellite cells (Lee and McPherron (1999) *Curr. Opin. Genet. Dev.* 9:604-07; McCroskery et al. (2003) *J. Cell. Biol.* 162:1135-47). It is expressed early in developing skeletal muscle, and continues to be expressed in adult skeletal muscle, preferentially in fast twitch types. Additionally, GDF-8 overexpressed in adult mice results in significant muscle loss (Zimmers et al. (2002) *Science* 296:1486-88). Also, natural mutations that render the GDF-8 gene inactive have been shown to cause both hypertrophy and hyperplasia in both animals and humans (Lee and McPherron (1997) supra). For example, GDF-8 knockout transgenic mice are characterized by a marked hypertrophy and hyperplasia of the skeletal muscle and altered cortical bone structure (McPherron et al. (1997) *Nature* 387:83-90; Hamrick et al. (2000) *Bone* 27:343-49). Similar increases in skeletal muscle mass are evident in natural GDF-8 mutations in cattle (Ashmore et al. (1974) *Growth* 38:501-07; Swatland et al. (1994) *J. Anim. Sci.* 38:752-57; McPherron et al., supra; Kambadur et al. (1997) *Genome Res.* 7:910-15). In addition, various studies indicate that increased GDF-8 expression is associated with HIV-induced muscle wasting (Gonzalez-Cadavid et al. (1998) *Proc. Natl. Acad. Sci. U.S.A.* 95:14938-43). GDF-8 has also been implicated in the production of muscle-specific enzymes (e.g., creatine kinase) and myoblast proliferation (WO 00/43781).

In addition to its growth-regulatory and morphogenetic properties, GDF-8 is believed to participate in numerous other physiological processes, including glucose homeostasis during type 2 diabetes development, impaired glucose tolerance, metabolic syndromes (i.e., a syndrome such as, e.g., syndrome X, involving the simultaneous occurrence of a group of health conditions, which may include insulin resistance, abdominal obesity, dyslipidemia, hypertension, chronic inflammation, a prothrombotic state, etc., that places a person at high risk for type 2 diabetes and/or heart disease), insulin resistance (e.g., resistance induced by trauma such as burns or nitrogen imbalance), and adipose tissue disorders (e.g., obesity, dyslipidemia, nonalcoholic fatty liver disease, etc.) (Kim et al. (2000) *Biochem. Biophys. Res. Comm.* 281:902-06).

A number of human and animal disorders are associated with functionally impaired muscle tissue, e.g., amyotrophic lateral sclerosis ("ALS"), muscular dystrophy ("MD"; including Duchenne's muscular dystrophy), muscle atrophy, organ atrophy, frailty, congestive obstructive pulmonary disease (COPD), sarcopenia, cachexia, and muscle wasting syndromes caused by other diseases and conditions. Currently, few reliable or effective therapies exist to treat these disorders. The pathology of these diseases indicates a potential role for GDF-8 signaling as a target in the treatment of these diseases.

ALS is a late onset and fatal neurodegenerative disease characterized by degeneration of the central nervous system and muscle atrophy. ALS typically initiates with abnormalities in gait and loss of dexterity, and then progresses to paralysis of limbs and diaphragm. While most cases of ALS are sporadic and are of unknown etiology, 5-10% of cases have been shown to result from dominant familial (FALS) inheritance. Approximately 10-20% of FALS cases are attributed to mutations in the Cu/Zn superoxide dismutase (SOD1) gene (reviewed in Bruijn et al. (2004) *Ann. Rev. Neurosci.* 27:723-49). SOD1 is a heterodimeric metallo-protein that catalyzes the reaction of superoxide into hydrogen peroxide and diatomic oxygen, and as loss of SOD1 does not result in motor neuron disease (Reaume et al. (1996) *Nat. Genet.* 13:43-47), it is believed to induce disease by toxic gain of function (reviewed in Bruijn et al., supra). The specific mechanisms of SOD1-induced neuronal cell death are unclear, and may involve alterations in axonal transport, cellular responses to misfolded protein, mitochondrial dysfunction, and excitotoxicity (Bruijn et al., supra).

The degeneration of motor neurons observed in ALS may occur via multiple mechanisms, including uptake or transport disruption of trophic factors by motor neurons (reviewed in Holzbaur (2004) *Trends Cell Biol.* 14:233-40). Thus, ALS might be treated by therapies that rejuvenate a degenerating neuron by providing an optimal survival environment. A nerve's environment includes nonneuronal cells such as glia and the muscle cells innervated by the motor neuron. This environment provides trophic and growth factors that are endocytosed by the neuron and transported via retrograde axonal transport to the cell body (Chao (2003) *Neuron* 39:1-2; Holzbaur, supra).

FALS has been modeled in both mouse and rat by the overexpression of mutant SOD1 (Howland et al. (2002) *Proc. Natl. Acad. Sci. U.S.A.* 99:1604-09). Transgenic mice overexpressing the G93A form of mutant SOD1 display muscle weakness and atrophy by 90 to 100 days of age, and typically die near 130 days of age (Gurney et al. (1994) *Science* 264: 1772-75). However, the underlying SODG93A-induced pathology, which includes grip strength weakness and loss of neuromuscular junctions, is significant as early as 50 days of age (Frey et al. (2000) *J. Neurosci.* 20:2534-42; Fisher et al. (2004) *Exp. Neuro.* 185:232-40; Ligon et al. (2005) *NeuroReport* 16:533-36; Wooley et al. (2005) *Muscle Nerve* 32:43-50). Transgenic rats expressing the SODG93A mutation follow a similar time course of degeneration (Howland et al., supra). Recent work has suggested that the development of pathology is not cell autonomous, consistent with the hypothesis that the degeneration of motor neurons observed in ALS occurs via multiple mechanisms, including the disruption of uptake and transport of trophic factors by the motor neuron (see above). Clement and coworkers have used chimeric mice to show that wild type nonneuronal cells can extend survival of motor neurons expressing mutant SOD1 (Clement et al. (2003) *Science* 302:113-17). These observations have led to the investigation of therapies that might slow neuronal degeneration by providing an optimal microenvironment for survival. For example, treatment of the SODG93A mouse via direct intramuscular injection of virally expressed growth factors (including IGF-1, GDNF and VEGF) prolongs animal survival (Kaspar et al. (2003) *Science* 301:839-42; Azzouz et al. (2004) *Nature* 429:413-17; Wang et al. (2002) *J. Neurosci.* 22:6920-28). In addition, muscle-specific expression of a local IGF-1-specific isoform (mIGF-1) stabilizes neuromuscular junctions, enhances motor neuron survival and delays onset and progression of disease in the SODG93A transgenic mouse model, indicating that direct effects on muscle can impact disease onset and progression in transgenic SOD 1 animals (Dobrowolny et al. (2005) *J. Cell Biol.* 168:193-99). Links between muscle hypermetabolism and motor neuron vulnerability have also been reported in ALS mice, supporting the hypothesis that defects in muscle may contribute to the disease etiology (Dupois et al. (2004) *Proc. Natl. Acad. Sci. USA.* 101:11159-64). Thus, enhancing muscle growth should provide improved local support for motor neurons, and therefore result in therapeutic benefits.

Inhibition of myostatin expression leads to both muscle hypertrophy and hyperplasia (Lee and McPherron, supra; McPherron et al., supra). Myostatin negatively regulates muscle regeneration after injury, and lack of myostatin in GDF-8 null mice results in accelerated muscle regeneration (McCroskery et al., (2005) *J. Cell. Sci.* 118:3531-41). Myostatin-neutralizing antibodies increase body weight, skeletal muscle mass, and muscle size and strength in the skeletal muscle of wild type mice (Whittemore et al. (2003) *Biochem. Biophys. Res. Commun.* 300:965-71) and the mdx mouse, a model for muscular dystrophy (Bogdanovich et al. (2002) *Nature* 420:418-21; Wagner et al. (2002) *Ann. Neurol.* 52:832-36). Furthermore, myostatin antibody in these mice decreased the damage to the diaphragm, a muscle that is also targeted during ALS pathogenesis. It has been hypothesized that the action of growth factors, such as HGF, on muscle may be due to inhibition of myostatin expression (McCroskery et al. (2005), supra), thereby helping to shift the "push and pull," or balance, between regeneration and degeneration in a positive direction. Thus, GDF-8 inhibition presents as a potential pharmacological target for the treatment of ALS, muscular dystrophy (MD), and other GDF-8-associated disorders, e.g., neuromuscular disorders for which it is desirable to increase muscle mass, strength, size, etc. With the availability of animal models (mouse and rat) of ALS, it is possible to test therapeutics in two different species, thus increasing the confidence of therapeutic effects in humans in vivo.

In addition to neuromuscular disorders in humans, there are also growth factor-related conditions associated with a loss of bone, such as osteoporosis and osteoarthritis, which predominantly affect the elderly and/or postmenopausal women. In addition, metabolic bone diseases and disorders include low bone mass due to chronic glucocorticoid therapy, premature gonadal failure, androgen suppression, vitamin D deficiency, secondary hyperparathyroidism, nutritional deficiencies, and anorexia nervosa. Although many current therapies for these conditions function by inhibiting bone resorption, a therapy that promotes bone formation would be a useful alternative treatment. Because GDF-8 plays a role in bone development as well as muscular development, regulation of GDF-8 is also an excellent pharmacological target for the treatment of bone-degenerative disorders.

Thus, a need exists to develop compounds and methods of treatment that contribute to an overall increase in muscle mass and/or strength and/or bone density, etc., particularly in humans, and particularly in those suffering from ALS and other muscle-wasting diseases as well as bone-degenerative disorders. Generating neutralizing antibodies and other small molecules with enhanced affinity to GDF-8 is an excellent pharmacological approach to treat these disorders.

SUMMARY OF THE INVENTION

The GDF-8 antagonists of the invention relate to antibodies (e.g., intact antibodies and antigen-binding fragments thereof), which are referred to herein as "anti-GDF-8 antibodies" or "GDF-8 antibodies." In one embodiment, an anti-GDF-8 antibody reduces, neutralizes, and/or antagonizes at least one GDF-8-associated activity (i.e., "GDF-8 activity"). The present invention thus provides methods to treat various bone, muscle, glucose and adipose disorders associated with GDF-8 activity using these anti-GDF-8 antibodies. The present invention discloses that GDF-8 antagonists, e.g., GDF-8 antibodies, are highly effective therapeutics when used to treat animals suffering from ALS, and that administration of such antibodies reduces the wasting of muscles targeted during ALS pathology, e.g., diaphragm, gastrocnemius, etc. In addition, the present invention discloses that these antagonists are highly effective at increasing muscle mass and grip strength in ALS-afflicted animals. As a result, the invention teaches that anti-GDF-8 antibodies are effective compositions to treat GDF-8-associated disorders, e.g., ALS, muscle wasting disorders or other disorders that result from GDF-8 dysregulation.

In one aspect, the invention features a method of treating (e.g., curing, suppressing), ameliorating, or preventing (e.g., delaying or preventing the onset, recurrence or relapse of) a GDF-8-associated disorder in a subject. The method includes: administering to the subject a GDF-8 antagonist, e.g., an anti-GDF-8 antibody, in an amount sufficient to treat or prevent the GDF-8-associated disorder. The GDF-8 antagonist, e.g., the anti-GDF-8 antibody, can be administered to the subject alone or in combination with other therapeutic modalities as described herein. The GDF-8 antibody can be administered therapeutically, prophylactically, or both. In one embodiment, the subject is a mammal, e.g., a human suffering from a GDF-8-associated disorder, including, e.g., bone and muscle disorders. Preferably, the subject is a human. More preferably, the subject is a human suffering from a GDF-8-associated disorder as described herein.

In one embodiment, the present invention provides safe and effective therapeutic methods for diagnosing, prognosing, monitoring, screening, treating, ameliorating, and/or preventing GDF-8-associated disorders, e.g., muscle disorders, neuromuscular disorders, bone-degenerative disorders, metabolic or induced bone disorders, adipose disorders, glucose metabolism disorders, or insulin-related disorders which include, but are not limited to, glucose homeostasis, type 2 diabetes, impaired glucose tolerance, metabolic syndrome (i.e., a syndrome involving the simultaneous occurrence of a group of health conditions, which may include insulin resistance, abdominal obesity, dyslipidemia, hypertension, chronic inflammation, a prothrombotic state, etc., that places a person at high risk for type 2 diabetes and/or heart disease), insulin resistance (e.g., resistance induced by trauma such as burns or nitrogen imbalance), adipose tissue disorders (e.g., obesity, dyslipidemia, nonalcoholic fatty liver disease, etc.), HIV-induced muscle wasting, muscular dystrophy (including Duchenne's muscular dystrophy), amyotrophic lateral sclerosis ("ALS"), muscle atrophy, organ atrophy, frailty, congestive obstructive pulmonary disease, sarcopenia, cachexia, muscle wasting syndromes, osteoporosis, osteoarthritis, metabolic bone diseases, and metabolic bone disorders (including low bone mass due to chronic glucocorticoid therapy, premature gonadal failure, androgen suppression, vitamin D deficiency, secondary hyperparathyroidism, nutritional deficiencies, and anorexia nervosa). In a preferred, but not limiting, embodiment, the invention provides safe and effective therapeutic methods for diagnosing, prognosing, monitoring, screening, treating, ameliorating, and/or preventing a GDF-8-associated disorder, e.g., a muscular disorder in vertebrates, particularly mammals, and more particularly humans. In a most preferred embodiment of the invention, the GDF-8-associated disorder, e.g., muscle disorder, diagnosed, prognosed, monitored, screened, treated, ameliorated, and/or prevented is ALS.

In another embodiment, this invention provides methods of inhibiting GDF-8 function in vivo or in vitro. These methods are useful for treating GDF-8-associated disorders, e.g., muscle and bone degenerative disorders, particularly muscle disorders such as ALS, and for increasing muscle mass and/or bone strength and/or density. The methods are also useful for increasing muscle mass and bone density in normal animals including, but not limited to, humans. The subject methods can be used in vitro (e.g., in a cell-free system, in culture, etc.), ex vivo, or in vivo. For example, GDF-8 receptor-expressing cells can be cultured in vitro in culture medium and contacted with, e.g., one or more anti-GDF-8 antibodies, e.g., as described herein. Alternatively, the method can be performed on cells present within a subject, e.g., as part of an in vivo (e.g., therapeutic or prophylactic) protocol.

Accordingly, in one aspect, the invention features a GDF-8 antagonist, e.g., an isolated antibody, that interacts with, e.g., binds to, and neutralizes and/or inhibits, GDF-8. In particular, the GDF-8 protein bound by the GDF-8 antibody is mammalian, e.g., human, sheep, nonhuman primate GDF-8. In another embodiment, the invention provides antibodies that bind GDF-8 with high affinity, e.g., with a Kd of at least $10^{-7}$ M, preferably $10^{-8}$, $10^{-9}$, $10^{-10}$, more preferably, $10^{-11}$ M or higher. The affinity and binding kinetics of the anti-GDF-8 antibody can be tested using several well-known methods, e.g., biosensor technology (Biacore, Piscataway, N.J.).

In one embodiment, the anti-GDF-8 antibody (e.g., an intact antibody or an antibody fragment (e.g., a Fab, F(ab')$_2$, Fv or a single chain Fv fragment)) is a monoclonal antibody. The antibody may be a human, humanized, chimeric, or an in vitro-generated antibody. In a preferred, but not limiting, embodiment, an anti-GDF-8 antibody of the invention is a humanized antibody.

These anti-GDF-8 antibodies can be used to diagnose, prognose, monitor, screen, treat, ameliorate, and/or prevent muscle, bone, adipose and glucose metabolism-related disorders. A nonlimiting example of an anti-GDF-8 antibody is referred to herein as "RK35," and includes both mouse and modified antibodies, e.g., chimeric or humanized forms. The nucleotide and amino acid sequences for the heavy chain variable region of mouse RK35 are set forth herein as SEQ ID NO:2 and SEQ ID NO:3, respectively. The nucleotide and amino acid sequences for the heavy chain variable region of humanized RK35 are set forth herein as SEQ ID NO:6 and SEQ ID NO:7, respectively. The nucleotide and amino acid sequences for the light chain variable region of mouse RK35 are set forth herein as SEQ ID NO:4 and SEQ ID NO:5, respectively. The nucleotide and amino acid sequences for the light chain variable region of humanized RK35 are set forth herein as SEQ ID NO:8 and SEQ ID NO:9, respectively.

In a preferred, but not limiting, embodiment of the invention, the antibody is a mouse or humanized antibody to GDF-8. In a more preferred embodiment of the invention, the antibody is comprised of the VH (variable heavy) domain set forth in SEQ ID NO:3 and the VL (variable light) domain set forth in SEQ ID NO:5. In another preferred embodiment of the invention, the antibody is comprised of the VH domain set forth in SEQ ID NO:7 and the VL domain set forth in SEQ ID NO:9. Additional embodiments of the invention comprise one or more VH or VL domains listed in Table 1.

Other embodiments of the invention comprise an H3 fragment of RK35, i.e., the sequence set forth as SEQ ID NO: 12. In yet another embodiment, a GDF-8 antagonist comprises one, two, or three complementarity determining regions (CDRs) from a heavy chain variable region of an antibody disclosed herein with sequences selected from SEQ ID NOs: 10-12 and 20-22. In yet another embodiment, an antagonist of the invention comprises one, two, or three CDRs from a light chain variable region of an antibody disclosed herein with sequences selected from SEQ ID NOs:13-15 and 23-25. In yet another embodiment, the antibody comprises one, two, three, four, five, or six CDRs with sequences selected from SEQ ID NOs:10-15 and 20-25.

The heavy and light chains of an anti-GDF-8 antibody of the invention may be full-length (e.g., an antibody can include at least one, and preferably two, complete heavy chains, and at least one, and preferably two, complete light chains) or may include an antigen-binding fragment (e.g., a Fab, F(ab')₂, Fv or a single chain Fv fragment ("scFv")). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa (e.g., human kappa). In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 117 and 120 of SEQ ID NO: 19. In one embodiment, the anti-GDF-8 antibody comprises the human IgG1 constant region shown in SEQ ID NO: 19. In another embodiment, the anti-GDF-8 antibody comprises a human kappa sequence, e.g., the sequence shown as SEQ ID NO:17.

In another embodiment, the invention provides GDF-8 antibodies as novel antibody fragments that bind GDF-8 and retain the ability to neutralize or reduce GDF-8 activity. In a preferred, but not limiting, embodiment of the invention, the antibody fragment is selected from the group consisting of a dAb fragment, a diabody, an Fd fragment, an Fab fragment, an F(ab')₂ fragment, an scFV fragment, and an Fv fragment. In a more preferred embodiment of the invention, the antibody fragment is encoded by a polynucleotide selected from SEQ ID NOs:2, 4, 6 or 8. In another preferred embodiment of the invention, the antibody fragment comprises an amino acid sequence selected from an amino acid sequence set forth in SEQ ID NOs: 10-15 and 20-25. In another preferred embodiment, the invention provides novel antibody fragments that differ in sequence (e.g., due to the redundancy of the genetic code) from those sequences listed in Table 1, yet retain the ability to bind GDF-8 and neutralize or reduce GDF-8 activity.

In another embodiment, the anti-GDF-8 antibody comprises at least one, two, three or four antigen-binding regions, e.g., variable regions, having an amino acid sequence as listed in Table 1 (SEQ ID NOs:3 or 7 for VH, and/or SEQ ID NOs:5 or 9 for VL), or a sequence substantially identical thereto (e.g., a sequence at least about 85%, 90%, 95%, 99% or more identical thereto, or which differs by no more than 1, 2, 5, 10 or 15 amino acid residues from SEQ ID NOs:3, 5, 7 or 9). In another embodiment, the antibody includes a VH and/or VL domain encoded by a nucleic acid having a nucleotide sequence as listed in Table 1 (SEQ ID NOs:2 or 6 for VH, and/or SEQ ID NOs:4 or 8 for VL), or a sequence substantially identical thereto (e.g., a sequence at least about 85%, 90%, 95%, 99% or more identical thereto, or which differs by no more than 3, 6, 15, 30 or 45 nucleotides from SEQ ID NOs:2, 4, 6, or 8). In yet another embodiment, the antibody comprises one, two, or three CDRs from a heavy chain variable region having amino acid sequences as listed in Table 1 (SEQ ID NOs:10-12 and 20-22), or a sequence substantially homologous thereto (e.g., a sequence at least about 85%, 90%, 95%, 99% or more identical thereto, and/or having one or more substitutions, e.g., conserved substitutions). In yet another embodiment, the antibody comprises at least one, two, or three CDRs from a light chain variable region having amino acid sequences as listed in Table 1 (SEQ ID NOs: 13-15 and 23-25), or a sequence substantially homologous thereto (e.g., a sequence at least about 85%, 90%, 95%, 99% or more identical thereto, and/or having one or more substitutions, e.g., conserved substitutions). In yet another embodiment, the antibody comprises one, two, three, four, five or six CDRs from heavy and light chain variable regions having amino acid sequences as listed in Table 1 (SEQ ID NOs:10-12 and 20-22 for VH CDRs; and SEQ ID NOs:13-15 and 23-25 for VL CDRs), or a sequence substantially homologous thereto (e.g., a sequence at least about 85%, 90%, 95%, 99% or more identical thereto, and/or having one or more substitutions, e.g., conserved substitutions).

In another embodiment, the anti-GDF-8 antibody comprises a human IgG1 constant region having an amino acid sequence as set forth in SEQ ID NO: 19 or a sequence substantially homologous thereto (e.g., a sequence at least about 85%, 90%, 95%, 99% or more identical thereto, or which differs by no more than 1, 2, 5, 10, 50, or 100 amino acid residues from SEQ ID NO: 19). In another embodiment, the anti-GDF-8 antibody comprises a human kappa constant chain, e.g., a human kappa constant chain having an amino acid sequence as set forth in SEQ ID NO: 17 or a sequence substantially homologous thereto (e.g., a sequence at least about 85%, 90%, 95%, 99% or more identical thereto, or which differs by no more than 1, 2, 5, 10, 20, or 50 amino acid residues from SEQ ID NO:17). In yet another embodiment, the antibody comprises a human IgG1 constant region and a human kappa constant chain as described herein.

In a preferred, but not limiting, embodiment, the invention provides antibodies encoded by polynucleotides set forth in SEQ ID NO:2, 4, 6, or 8. In another preferred embodiment, the invention provides antibodies encoded by polynucleotide sequences that hybridize under stringent conditions to the polynucleotides set forth in SEQ ID NOs:2, 4, 6, or 8. In another preferred embodiment, the invention provides antibodies encoded by polynucleotides, which differ from those sequences set forth in SEQ ID NOs:2, 4, 6, or 8, but due to the degeneracy of the genetic code, encode an amino acid sequence set forth in SEQ ID NOs:3, 5, 7, 9, or 10-15.

The GDF-8 antagonist, e.g., an anti-GDF-8 antibody, can be derivatized or linked to another functional molecule, e.g., another peptide or protein (e.g., an Fab fragment). For example, a fusion protein or an antibody, or antigen-binding portion, can be functionally linked (e.g., by chemical coupling, genetic fusion, noncovalent association or otherwise) to one or more other molecular entities, such as an antibody (e.g., a bispecific or a multispecific antibody), toxins, radioisotopes, cytotoxic or cytostatic agents, among others.

A further aspect of the invention provides as GDF-8 antagonists purified and isolated nucleic acids that encode the GDF-8 antagonists, e.g., anti-GDF-8 antibodies, of the invention. In one embodiment, the invention provides polynucleotides comprised of a sequence encoding a VH (SEQ ID NO:3 or SEQ ID NO:7), VL (SEQ ID NO:5 or SEQ ID NO:9), and/or CDR (SEQ ID NOs:10-15 and 20-25) as listed in Table 1. In another embodiment, the invention provides polynucleotides that hybridize under stringent conditions to nucleic acids encoding a VH, VL, or CDR (SEQ ID NOs:3, 5, 7, 9, 10-15, or 20-25) as listed in Table 1. In another embodiment, the invention provides nucleic acids that comprise SEQ ID NOs:2, 4, 6, or 8 or fragments of SEQ ID NOs:2, 4, 6, or 8. In yet a further embodiment, the invention provides polynucleotides that hybridize under stringent conditions to SEQ ID NOs:2, 4, 6 or 8. Another aspect of the invention provides host cells and vectors comprising the polynucleotides of the invention as GDF-8 antagonists.

The antibodies of the invention possess a number of useful properties. First, the antibodies are capable of binding mature GDF-8 with high affinity. Second, the disclosed antibodies inhibit GDF-8 activity in vitro and in vivo. Third, the disclosed antibodies inhibit GDF-8 activity associated with negative regulation of skeletal muscle mass and bone density. Fourth, the disclosed antibodies are an effective treatment for muscular disorders, particularly ALS. These antibodies have many additional uses, including diagnosing, prognosing, monitoring, screening, treating, ameliorating, and/or preventing GDF-8-associated disorders, e.g., muscle and/or bone-associated disorders.

Other aspects of the invention provide compositions comprised of a GDF-8 antagonist of the invention, e.g., an anti-GDF-8 antibody of the invention, and the use of such compositions in inhibiting or neutralizing GDF-8 in animals, particularly in humans or other animals with muscular disorders such as ALS. The antibodies of the invention may also be used in a GDF-8-associated disorder, e.g., in a disorder in which it is desirable to increase muscle tissue or bone density. For example, anti-GDF-8 antibodies may be used in therapies and compositions to repair damaged muscle, e.g., myocardium, diaphragm, etc. Exemplary GDF-8-associated disorders and diseases treated by the disclosed methods and compositions include muscle and neuromuscular disorders such as muscular dystrophy (including Duchenne's muscular dystrophy); amyotrophic lateral sclerosis; muscle atrophy; organ atrophy; frailty; tunnel syndrome; congestive obstructive pulmonary disease (COPD); sarcopenia, cachexia, and other muscle wasting syndromes; adipose tissue disorders (e.g., obesity); type 2 diabetes; impaired glucose tolerance; metabolic syndromes (e.g., syndrome X); insulin resistance (including resistance induced by trauma, e.g., burns or nitrogen imbalance), and bone-degenerative diseases (e.g., osteoarthritis and osteoporosis).

In a preferred, but not limiting, embodiment of the invention, a composition containing an anti-GDF-8 antibody is used in a method of treating, reducing, or ameliorating ALS.

In another aspect, the invention provides compositions, e.g., pharmaceutical compositions, that include a pharmaceutically acceptable carrier and at least one GDF-8 antagonist, e.g., an anti-GDF-8 antibody described herein. In one embodiment, the compositions, e.g., pharmaceutical compositions, comprise a combination of two or more of the aforesaid GDF-8 antagonists, e.g., anti-GDF-8 antibodies or fragments thereof. Also within the scope of the invention are combinations of the GDF-8 antagonist, e.g., an anti-GDF-8 antibody, with a therapeutic agent, e.g., growth factor inhibitors, immunosuppressants, anti-inflammatory agents (e.g., systemic anti-inflammatory agents), metabolic inhibitors, enzyme inhibitors, and/or cytotoxic or cytostatic agents.

In yet another embodiment, the GDF-8 antagonist, e.g., an anti-GDF-8 antibody, or a pharmaceutical composition thereof, is administered alone or in combination therapy, i.e., combined with other agents, e.g., therapeutic agents, which are useful for treating GDF-8-associated disorders.

In addition to use in the treatment of various diseases or disorders, anti-GDF-8 antibodies may be used as diagnostic tools to quantitatively or qualitatively detect GDF-8 protein or protein fragments in a biological sample. The presence or amount of GDF-8 protein detected can be correlated with one or more of the medical conditions listed herein. Thus, in one embodiment, the invention provides methods to diagnose, prognose, monitor, and/or screen for GDF-8-associated disorders.

In another aspect, the invention provides a method for detecting the presence of GDF-8 in a sample in vitro (e.g., a biological sample, such as serum, plasma, tissue, biopsy). The subject method can be used to diagnose a GDF-8-associated disorder, e.g., a bone, muscle, adipose or glucose metabolism-associated disorder. The method includes: (i) contacting the sample or a control sample with an anti-GDF-8 antibody as described herein; and (ii) detecting formation of a complex between the anti-GDF-8 antibody, and the sample or the control sample, wherein a substantially significant change in the formation of the complex in the sample relative to the control sample is indicative of the presence of GDF-8 in the sample.

In yet another aspect, the invention provides a method for detecting the presence of GDF-8 in vivo in a subject (e.g., in vivo imaging in a subject). The subject method can be used to diagnose a GDF-8-associated disorder, e.g., ALS. The method includes: (i) administering an anti-GDF-8 antibody as described herein to a subject or a control subject under conditions that allow binding of the antibody to GDF-8; and (ii) detecting formation of a complex between the antibody and GDF-8, wherein a substantially significant difference in the formation of the complex in the subject relative to the control subject provides an indication related to the presence of GDF-8.

Other embodiments of the invention provide a method of diagnosing or detecting whether a patient is suffering from a GDF-8-associated disorder (e.g., muscle disorder, neuromuscular disorder, bone degenerative disorder, metabolic or induced bone disorder, adipose disorder, glucose metabolism disorder, or insulin-related disorder) comprising the steps of: (a) obtaining a sample from a patient of interest; (b) contacting the sample with an anti-GDF-8 antibody as described herein; (c) determining the level of GDF-8 present in the patient sample; and (d) comparing the level of GDF-8 in the patient sample to the level of GDF-8 in a control sample, wherein a substantial increase, decrease, or similarity in the level of GDF-8 in the patient sample compared to the level of GDF-8 in the control sample indicates whether the patient is suffering from a GDF-8-associated disorder.

Another further embodiment of a method for diagnosing or detecting whether a patient is suffering from a GDF-8-associated disorder described herein comprises the steps of: (a) obtaining a first sample taken from the patient of interest; (b) contacting the first sample with an anti-GDF-8 antibody as described herein; (c) determining the level of a GDF-8 in the first sample; (d) obtaining a second sample from an individual not afflicted with the GDF-8-associated disorder; (e) contacting the second sample with an anti-GDF-8 antibody as described herein; (f) determining the level of GDF-8 in the second sample; and (g) comparing the levels of GDF-8 in the first and second samples, wherein a substantial increase, decrease, or similarity in the level of first sample compared to the second sample indicates whether the patient is suffering from a GDF-8-associated disorder caused (in part or in full) by overexpression of GDF-8. For example, an increase in the level of GDF-8 in the first sample compared to the second sample may indicate that the patient is suffering from the GDF-8-associated disorder. In contrast, a decrease or similarity in the level of GDF-8 in the first sample compared to the second sample may indicate that the patient is not suffering from the GDF-8-associated disorder.

Antibodies of the invention are also useful in methods of prognosing the likelihood that a patient will develop a GDF-8-associated disorder, e.g., a muscle disorder, neuromuscular disorder, bone degenerative disorder, metabolic or induced bone disorder, adipose disorder, glucose metabolism disorder, or insulin-related disorder. In a preferred, but nonlimiting, embodiment, the method comprises the steps of: (a) obtaining a first sample from a patient of interest; (b) contacting the first sample with an anti-GDF-8 antibody as described herein; (c) determining the level of GDF-8 in the first sample;

(d) obtaining a second sample from an individual not afflicted with the GDF-8-associated disorder; (e) contacting the second sample with an anti-GDF-8 antibody as described herein; (f) determining the level of GDF-8 in the second sample; and (g) comparing the levels of GDF-8 in the first and second samples, wherein an increase, decrease, or similarity in the level of GDF-8 in the first sample as compared with the second sample indicates the likelihood that the patient will develop the GDF-8-associated disorder. For example, for a GDF-8-associated disorder caused (in part or in full) by overexpression of GDF-8, it is likely that the patient will develop the GDF-8-associated disorder if the first sample has an increased level of GDF-8 compared to second sample. In contrast, for a GDF-8-associated disorder caused (in part or in full) by overexpression of GDF-8, it is unlikely that the patient will develop the GDF-8-associated disorder if the first sample has a similar or decreased level of GDF-8 compared to second sample.

Antibodies of the invention are also useful in methods of monitoring the severity of a GDF-8-associated disorder, e.g., muscle disorder, neuromuscular disorder, bone degenerative disorder, metabolic or induced bone disorder, adipose disorder, glucose metabolism disorder, or insulin-related disorder. In a preferred, but not limiting, embodiment, the method comprises the steps of: (a) obtaining a first sample taken from a patient of interest at a first time point; (b) contacting the first sample with an anti-GDF-8 antibody as described herein; (c) determining the level of GDF-8 in the first sample; (d) obtaining a second sample taken from the patient at a second time point; (e) contacting the second sample with an anti-GDF-8 antibody as described herein; (f) determining the level of GDF-8 in the second sample; and (g) comparing the levels of GDF-8 in the first and second samples, wherein an increase, decrease, or similarity in the level of GDF-8 in the second sample indicates whether the GDF-8-associated disorder has changed in severity. In one embodiment, a method of monitoring of the invention is used to monitor ALS, and a decrease in the level of GDF-8 in the second sample indicates that ALS has decreased in severity.

An additional method of monitoring a disorder as described herein comprises the steps of: (a) obtaining a first sample from a patient of interest; (b) contacting the first sample with an anti-GDF-8 antibody as described herein; (c) determining the level of GDF-8 in the first sample; (d) obtaining a second sample from an individual not afflicted with a muscle disorder, neuromuscular disorder, bone degenerative disorder, metabolic or induced bone disorder, adipose disorder, glucose metabolism disorder, or insulin-related disorder; (e) contacting the second sample with an anti-GDF-8 antibody as described herein; (f) determining the level of GDF-8 in the second sample; and (g) comparing the levels of GDF-8 in the first and second samples, wherein an increase, decrease, or similarity in the level of GDF-8 in the first sample compared to the second sample indicates the severity of the GDF-8 disorder at that point. In one embodiment, a method of monitoring of the invention is used to monitor ALS, and a decrease or similarity in the level of GDF-8 in the first sample compared to the second sample indicates that ALS has low severity.

Preferably, the antibody is directly or indirectly labeled with a detectable substance to facilitate detection of the bound or unbound antibody. Suitable detectable substances include various enzymes, prosthetic groups, fluorescent materials, luminescent materials and radioactive materials.

Methods for delivering or targeting an antagonist of the invention, e.g., an antibody, to a GDF-8-expressing cell in vivo are also disclosed herein and are within the scope of the invention.

Kits comprising the GDF-8 antagonists, e.g., the anti-GDF-8 antibodies, of the invention for therapeutic and diagnostic uses are also within the scope of the invention Additional objects of the invention will be set forth in the following description. Various objects, aspects, and advantages of the invention will be realized and attained by means of the elements and combinations particularly pointed out in the claims.

It is to be understood that both the foregoing general description and the following detailed description are exemplary and explanatory only, and are not restrictive of the invention as claimed.

BRIEF DESCRIPTION OF THE DRAWINGS

FIG. 7. is an image of a dot blot showing epitope mapping of GDF-8 for the RK35 antibody. The binding sites on GDF-8 for RK35 were identified using forty-eight (48) overlapping 13 amino acid peptides (13-mers) of human GDF-8 (RK35 antibody binding to 13-mers 1 through 24 is shown in the top row of the blot and RK35 binding to 13-mers 25-48 is shown in the bottom row of the blot). FIG. 7 discloses amino acid residues 1-55 (top row) and amino acid residues 56-109 (bottom row) of human GDF-8 relative to SEQ ID NO: 1. The amino acid residue RK35 contact sites with GDF-8 are indicated in bold.

FIG. 8. Alignment of the light chain and heavy chain variable regions of RK35 (VL and VH, respectively) with the human germline frameworks DPK9 and DP-47, respectively. The alignment of the amino acid sequences of the VL regions of murine RK35 (MRK35 VL; SEQ ID NO:5), humanized RK35 (HuRK35 VL; SEQ ID NO:9) and germline DPK-9 (SEQ ID NO:32) is shown. The alignment of the amino acid sequences of the VH regions of murine RK35 (mRK35 VH; SEQ ID NO:3), humanized RK35 (HuRK35 VH; SEQ ID NO:7) and germline DP-47 (SEQ ID NO:33) is also shown. The amino acids of the murine RK35 (MRK35) variable chains that are changed in the humanized RK35 (HuRK35) regions are designated with an asterisk (*) and are in bold; complementarity determining regions of RK35 are boxed and underlined.

DETAILED DESCRIPTION OF THE INVENTION

I. Definitions

Figure 1A:
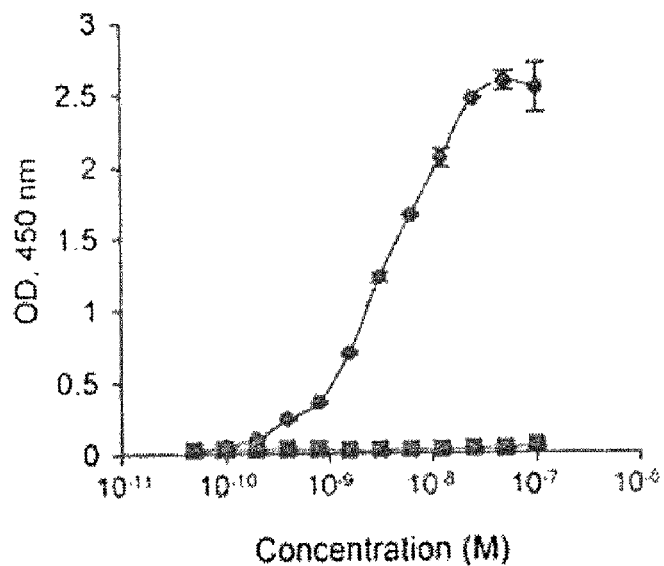
FIG. 1. Characterization of the RK35 anti-GDF-8 antibody. A. Direct binding of RK35 antibody to GDF-8, as measured in an ELISA assay with biotinylated GDF-8. The binding affinity of RK35 antibody (circles) for GDF-8 was determined to be 4 nM. Control IgG shows no appreciable binding (squares). B. Effect of RK35 antibody on GDF-8 binding to its high affinity receptor. In a competition ELISA using the high affinity GDF-8 receptor, ActRIIB was used to measure the GDF-8 inhibitory activity of RK35. The binding of biotinylated GDF-8 to immobilized human chimeric protein ActRIIB fused to the human IgG constant region (Fc) was evaluated in the absence (diamonds) or presence of various concentrations of RK35 mAb, soluble ActRIIB or control IgG. Soluble ActRIIB-Fc receptor (squares) and irrelevant mouse IgG (triangles) were used as positive and negative controls, respectively. RK35 (circles) blocked the binding of biotinylated GDF-8 to immobilized ActRIIB with an $IC_{50}$~2.5 µM. C. Inhibition of GDF-8-induced signal transduction. Rhabdomyosarcoma cells expressing a TGF-β promoter-luciferase fusion gene were treated with 10 ng/ml of GDF-8 in the absence (squares) or presence (circles) of varying concentrations of RK35 antibody. RK35 reduced the GDF-8 induction of luciferase activity in a dose-responsive manner, with an $IC_{50}$ of 0.2 nM. Background (diamonds) signal was measured with no GDF-8 added.

"Antibody," as used herein, refers to an immunoglobulin or a part thereof, and encompasses any polypeptide comprising an antigen-binding site regardless of the source, species of origin, method of production, and characteristics. For the purposes of the present invention, it also includes, unless otherwise stated, antibody fragments such as Fab, F(ab')$_2$, Fv, scFv, Fd, dAb, diabodies, and other antibody fragments that retain antigen-binding function. Antibodies can be made, for example, via traditional hybridoma techniques, recombinant DNA methods, or phage display techniques using antibody libraries. For various other antibody production techniques, see Antibodies: A Laboratory Manual, eds. Harlow et al., Cold Spring Harbor Laboratory, 1988.

The term "antigen-binding domain" refers to the part of an antibody molecule that comprises the area specifically binding to or complementary to a part or all of an antigen. Where an antigen is large, an antibody may only bind to a particular part of the antigen. The "epitope" or "antigenic determinant" is a portion of an antigen molecule that is responsible for interactions with the antigen-binding domain of an antibody. An antigen-binding domain may be provided by one or more antibody variable domains (e.g., a so-called Fd antibody fragment consisting of a VH domain). An antigen-binding domain may comprise an antibody light chain variable region (VL) and an antibody heavy chain variable region (VH).

The term "GDF-8" refers to a specific growth and differentiation factor-8, but not other factors that are structurally or functionally related to GDF-8, for example, BMP-11 and other factors belonging to the TGF-β superfamily. The term refers to the full-length unprocessed precursor form of GDF-8 as well as the mature and propeptide forms resulting from post-translational cleavage. The term also refers to any fragments and variants of GDF-8 that maintain at least some biological activities associated with mature GDF-8, as discussed herein, including sequences that have been modified. The amino acid sequence of mature human GDF-8 is provided in SEQ ID NO: 1. The present invention relates to GDF-8 from all vertebrate species, including, but not limited to, human, bovine, chicken, mouse, rat, porcine, ovine, turkey, baboon, and fish (for sequence information, see, e.g., McPherron et al., supra).

The term "GDF-8 activity" refers to one or more of physiologically growth-regulatory or morphogenetic activities associated with active GDF-8 protein. For example, active GDF-8 is a negative regulator of skeletal muscle mass. Active GDF-8 can also modulate the production of muscle-specific enzymes (e.g., creatine kinase), stimulate myoblast proliferation, and modulate preadipocyte differentiation to adipocytes. Exemplary procedures for measuring GDF-8 activity in vivo and in vitro are set forth in the Examples.

The term "GDF-8 antagonist" or "GDF-8 inhibitor" includes any agent capable of inhibiting activity, expression, processing, or secretion of GDF-8. Such inhibitors include macromolecules and small molecules, e.g., proteins, antibodies, peptides, peptidomimetics, siRNA, ribozymes, antisense oligonucleotides, double-stranded RNA, and other small molecules, that inhibit GDF-8. A GDF-8 antagonist includes, in addition to the antibodies provided herein, any antibody that efficiently inhibits GDF-8, including antibodies with high specificity for binding to GDF-8 (e.g., antibodies with a low affinity for other members of the TGF-β superfamily (e.g., BMP-11)). Variants, including humanized variants, of these antibodies are contemplated in the methods of diagnosing, prognosing, monitoring, treating, ameliorating, and preventing of the invention. Such inhibitors are said to "inhibit," "decrease," or "reduce" the biological activity of GDF-8.

The terms "neutralize," "neutralizing," and their cognates refer to a dramatic reduction or abrogation of GDF-8 activity relative to the activity of GDF-8 in the absence of the same inhibitor. For example, a reduction of 75-100% of activity may be said to "neutralize" GDF-8 activity.

The term "treatment" is used interchangeably herein with the term "therapeutic method" and refers to both therapeutic treatment and prophylactic/preventative measures. Those in need of treatment may include individuals already having a particular medical disorder as well as those who may ultimately acquire the disorder (i.e., those needing preventive measures).

The term "isolated" refers to a molecule that is substantially separated from its natural environment. For instance, an isolated protein is one that is substantially separated from the cell or tissue source from which it is derived.

The term "purified" refers to a molecule that is substantially free of other material that associates with the molecule in its natural environment. For instance, a purified protein is substantially free of the cellular material or other proteins from the cell or tissue from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure.

The term "effective dose," "therapeutically effective dose," "effective amount," or the like refers to that amount of the compound that results in either amelioration of symptoms in a patient or a desired biological outcome (e.g., increasing skeletal muscle mass and/or bone density). Such amount should be sufficient to reduce the activity of GDF-8 associated with negative regulation of skeletal muscle mass and bone density or with glucose homeostasis and adipose metabolism. The effective amount can be determined as described herein.

A "disorder associated with GDF-8 activity," "disorder associated with GDF-8," "GDF-8-associated disorder" or the like refers to disorders that may be caused, in full or in part, by dysregulation of (e.g., abnormally increased or decreased) GDF-8 (and/or GDF-8 activity), and/or disorders that may be treated, ameliorated, prevented, diagnosed, prognosed, or monitored by regulating and/or monitoring GDF-8 (and/or GDF-8 activity). GDF-8-associated disorders include muscle disorders, neuromuscular disorders, bone degenerative disorders, metabolic or induced bone disorders, adipose disorders, glucose metabolism disorders or insulin-related disorders. A preferred GDF-8-associated disorder of the invention is amyotrophic lateral sclerosis (ALS).

The term "small molecule" refers to compounds that are not macromolecules (see, e.g., Karp (2000) Bioinformatics Ontology 16:269-85; Verkman (2004) AJP-Cell Physiol. 286: 465-74). Thus, small molecules are often considered those compounds that are less than one thousand daltons (e.g., Voet and Voet, Biochemistry, $2^{nd}$ ed, ed. N. Rose, Wiley and Sons, New York, 14 (1995)). For example, Davis et al. ((2005) Proc. Natl. Acad. Sci. USA 102:5981-86) use the phrase small molecule to indicate folates, methotrexate, and neuropeptides, while Halpin and Harbury ((2004) PLos Biology 2:1022-30) use the phrase to indicate small molecule gene products, e.g., DNAs, RNAs and peptides. Examples of natural small molecules include, but are not limited to, cholesterols, neurotransmitters, and siRNAs; synthesized small molecules include, but are not limited to, various chemicals listed in numerous commercially available small molecule databases, e.g., FCD (Fine Chemicals Database), SMID (Small Molecule Interaction Database), ChEBI (Chemical Entities of Biological Interest), and CSD (Cambridge Structural Database) (see, e.g., Alfarano et al. (2005) Nuc. Acids Res. Database Issue 33:D416-24).

II. Antibodies Against GDF-8 and Antibody Fragments

A. Mouse and Humanized Antibody RK35

The present disclosure provides novel antibodies (e.g., intact antibodies and antibody fragments) that efficiently bind GDF-8. A nonlimiting illustrative embodiment of such an antibody is termed RK35. This exemplary embodiment is provided in the form of mouse and humanized antibodies, and antibody fragments thereof.

The exemplary antibody of the invention, referred to herein as "RK35," possesses unique and beneficial characteristics. First, this antibody and antibody fragments are capable of binding mature GDF-8 with high affinity. Second, the antibody and antibody fragments of the invention inhibit GDF-8 activity in vitro and in vivo as demonstrated, for example, by inhibition of ActRIIB binding and reporter gene assays. Third, the disclosed antibody and antibody fragments are useful to treat symptoms associated with a GDF-8-associated disorder, e.g., muscular disorders, particularly ALS, as demonstrated, e.g., by increasing muscle mass in treated mutant SOD mice.

In an exemplary embodiment, GDF-8 antagonists are antibodies that efficiently bind to GDF-8 and inhibit one or more GDF-8 associated activities. One of ordinary skill in the art will recognize that the antibodies of the invention may be used to detect, measure, and inhibit GDF proteins derived from various species, e.g., those described in the present specification. The percent identity is determined by standard alignment algorithms such as, for example, Basic Local Alignment Tool (BLAST) described in Altschul et al. (1990) *J. Mol. Biol.* 215:403-10, the algorithm of Needleman et al. (1970) *J. Mol. Biol.* 48:444-53, or the algorithm of Meyers et al. (1988) *Comput. Appl. Biosci.* 4:11-17. In general, the antibody and antibody fragments of the invention can be used with any protein that retains substantial GDF-8 biological activity and comprises an amino acid sequence which is at least about 70%, 80%, 90%, 95%, or more identical to any sequence of at least 100, 80, 60, 40, 20, or 15 contiguous amino acids of the mature form of GDF-8 set forth in SEQ ID NO:1.

B. Antibody Variable Domains

Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain is composed of an N-terminal variable (V) domain (VL) and a constant (C) domain (CL). Each heavy chain is composed of an N-terminal V domain (VH), three or four C domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

Nonlimiting examples of binding fragments encompassed within the term "antibody fragment" used herein include: (i) an Fab fragment, a monovalent fragment consisting of the VL, VH, CL and CH1 domains; (ii) an $F(ab')_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH regions pair to form monovalent molecules (known as single chain Fv (scFv). The most commonly used linker is a 15-residue $(Gly_4Ser)_3$ (SEQ ID NO: 34) peptide, but other linkers are also known in the art. Single chain antibodies are also intended to be encompassed within the term "antibody" or "antigen-binding fragment" of an antibody. These antibodies are obtained using conventional techniques known to those skilled in the art, and the fragments are screened for utility in the same manner as intact antibodies.

Antibody diversity is created by multiple germline genes encoding variable regions and a variety of somatic events. The somatic events include recombination of variable gene segments with diversity (D) and joining (J) gene segments to make a complete VH region, and the recombination of variable and joining gene segments to make a complete VL region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Thus, the present invention provides novel antibodies that bind GDF-8. The antibody fragments of the invention, e.g., structures containing a CDR, will generally be an antibody heavy or light chain sequence, or an active fragment thereof, in which the CDR is placed at a location corresponding to the CDR of naturally occurring VH and VL. The structures and locations of immunoglobulin variable domains, e.g., CDRs, may be defined using well-known numbering schemes, e.g., the Kabat numbering scheme, the Chothia numbering scheme, a combination of Kabat and Chothia (AbM), etc. (see, e.g., Sequences of Proteins of Immunological Interest, U.S. Department of Health and Human Services (1991), eds. Kabat et al.; Al-Lazikani et al. (1997) *J. Mol. Biol.* 273:927-48).

Thus, the present invention further provides novel CDRs. The structure for carrying a CDR of the invention will generally be a polypeptide, e.g., an antibody heavy or light chain sequence or a substantial portion thereof, in which the CDR is located at a position corresponding to the CDR of naturally occurring VH and VL regions. The structures and locations of immunoglobulin variable domains may be determined as described in, e.g., Kabat et al., supra and Al-Lazikani et al., supra.

Antibody molecules (including antibody fragments) of the present invention, i.e., antibody molecules that antagonize GDF-8, include, but are not limited to, murine monoclonal antibody RK35 and its variants, specifically the humanized variant. GDF-8 antagonists of the invention include, in addition to RK35, other antibodies that bind efficiently to GDF-8, including antibodies with high specificity for binding to GDF-8 (e.g., antibodies with a lower affinity for other members of the TGF-β superfamily (e.g., BMP-11)). Variants, including humanized variants, of these antibodies are contemplated in the methods of diagnosing, prognosing, monitoring, treating, ameliorating, and preventing of the invention. These antibody molecules may be useful in preventing or treating a GDF-8-associated disorder, e.g., bone, muscle, adipose and glucose metabolism-related pathologies. The amino acid sequences of the light chain variable regions of murine and humanized RK35 are set forth in SEQ ID NOs:5 and 9, respectively. The amino acid sequences of the heavy chain variable regions of murine and humanized RK35 are set forth in SEQ ID NOs:3 and 7, respectively. The amino acid sequences of the three complementarity determining regions (CDRs) in the variable light chains of murine and humanized RK35 are set forth in SEQ ID NOs:13, 14, 15, 23, 24, and 25. The amino acid sequences of the three CDRs in the variable heavy chains of murine and humanized RK35 are set forth in SEQ ID NOs:10, 11, 12, 20, 21, and 22.

As described above, the CDRs contain most of the residues responsible for interactions with an antigen, and are contained within the VH and VL domains, i.e., the heavy chain variable region and the light chain variable region, respectively. Consequently, provided that an antibody comprises at least one CDR comprising an amino acid sequence selected from the amino acid sequences set forth in SEQ ID NOs: 10-15 and 20-25, or an active antibody fragment thereof, it is an antibody of the invention, i.e., one that binds to GDF-8 and interferes with GDF-8 signaling. Therefore, an embodiment of the invention includes polypeptides, e.g., antibodies, that contain one or more CDRs that comprise an amino acid sequence selected from the amino acid sequences set forth in SEQ ID NOs: 10-15 and 20-25, or an active fragment thereof. Consequently, one of skill in the art will recognize that the antibodies of the invention include an antibody in which the CDRs of the VL chain are those set forth in SEQ ID NOs: 13-15 and 23-25, or the CDRs of the VH chain are those set forth in SEQ ID NOs: 10-12 and 20-22.

An antigen-binding fragment may be an Fv fragment, which consists of VH and VL domains. Thus, an Fv fragment of RK35 may constitute an antibody of the invention, provided that it binds to GDF-8 and interferes with GDF-8 signaling. One of skill in the art will recognize that any antibody fragment containing the Fv fragment of, e.g., RK35, may also be an antibody of the invention. Additionally, any Fv fragment, scFv fragment, Fab fragment, or F(ab')$_2$ fragment, that contains one or more CDRs having an amino acid sequence selected from the amino acid sequences set forth in SEQ ID NOs:10-15 and 20-25, may also be an antibody of the invention.

Such antibody molecules may be produced by methods well known to those skilled in the art. For example, monoclonal antibodies may be produced by generation of hybridomas in accordance with known methods. Hybridomas formed in this manner are then screened using standard methods, such as enzyme-linked immunosorbent assay (ELISA) and Biacore analysis, to identify one or more hybridomas that produce an antibody that binds GDF-8, interferes with GDF-8 signaling, and neutralizes or inhibits one or more GDF-8-associated activities. Recombinant GDF-8, naturally occurring GDF-8, any variants thereof, and antigenic peptide fragments of GDF-8 may be used as the immunogen. An antigenic peptide fragment of GDF-8 comprises at least seven continuous amino acid residues and encompasses an epitope such that an antibody raised against the peptide forms an immune complex with GDF-8. Preferably, the antigenic peptide comprises at least 10 amino acid residues, more preferably at least 15 amino acid residues, even more preferably at least 20 amino acid residues, and most preferably at least 30 amino acid residues. Additionally, it is preferable that the antigenic peptide fragment of GDF-8 comprises the GDF-8 receptor-binding site.

Polyclonal sera and antibodies of the invention may be produced by immunizing a suitable subject with GDF-8, its variants, and/or portions thereof. The antibody titer in the immunized subject may be monitored over time by standard techniques, such as an ELISA, or by using immobilized GDF-8 or other marker proteins (e.g., FLAG). If desired, the antibody molecules of the present invention may be isolated from the subject or culture media and further purified by well-known techniques, such as protein A chromatography, to obtain an IgG fraction.

Certain embodiments of the invention comprise the VH and/or VL domain of the Fv fragment of RK35. Fragments of antibodies of the present invention, e.g., Fab, F(ab')$_2$, Fd, and dAb fragments, may be produced by cleavage of the antibodies in accordance with methods well known in the art. For example, immunologically active Fab and F(ab')$_2$ fragments may be generated by treating the antibodies with an enzyme such as papain and pepsin.

Further embodiments comprise one or more CDRs of any of these VH and VL domains, as set forth in SEQ ID NOs: 10-15 and 20-25. One embodiment comprises an H3 fragment of the VH domain of RK35 as set forth in SEQ ID NO: 12.

DNA and amino acid (AA) sequences of VH and VL domains, and CDRs of the presently disclosed antibodies are enumerated as listed in Table 1. For convenience, the approximate positions of each CDR within the VH and VL domains are listed in Table 2.

TABLE 1

DNA and Amino Acid Sequences of
VH, VL, CH, CL and CDRs in RK35

| | | |
|---|---|---|
| MOUSE | DNA seq. of VH | SEQ ID NO: 2 |
| | AA seq. of VH | SEQ ID NO: 3 |
| | DNA seq. of VL | SEQ ID NO: 4 |
| | AA seq. of VL | SEQ ID NO: 5 |
| HUMANIZED | DNA seq. of VH | SEQ ID NO: 6 |
| | AA seq. of VH | SEQ ID NO: 7 |

TABLE 1-continued

DNA and Amino Acid Sequences of
VH, VL, CH, CL and CDRs in RK35

|  | | |
|---|---|---|
| | DNA seq. of VL | SEQ ID NO: 8 |
| | AA seq. of VL | SEQ ID NO: 9 |
| CDRs BASED ON KABAT | AA sequence of H1 | SEQ ID NO: 10 or *SEQ ID NO: 20* |
| OR AbM (ital) DEFINITIONS | AA sequence of H2 | SEQ ID NO: 11 or *SEQ ID NO: 21* |
| | AA sequence of H3 | SEQ ID NO: 12 or *SEQ ID NO: 22* |
| | AA sequence of L1 | SEQ ID NO: 13 or *SEQ ID NO: 23* |
| | AA sequence of L2 | SEQ ID NO: 14 or *SEQ ID NO: 24* |
| | AA sequence of L3 | SEQ ID NO: 15 or *SEQ ID NO: 25* |
| | DNA seq. of CL | SEQ ID NO: 16 |
| | AA seq. of CL | SEQ ID NO: 17 |
| | DNA seq. of CH | SEQ ID NO: 18 |
| | AA seq. of CH | SEQ ID NO: 19 |

TABLE 2

Approximate CDR position according to Kabat (not ital.) or AbM (ital.) definitions within variable regions of RK35 mouse and humanized antibodies

| CDR | RK35 | RK35 |
|---|---|---|
| | SEQ ID NO: 3 | SEQ ID NO: 7 |
| H1 | 31-35 or *26-35* | 31-35 or *26-55* |
| H2 | 50-66 or *50-59* | 50-66 or *50-59* |
| H3 | 99-105 or *99-105* | 99-105 or *99-105* |
| | SEQ ID NO: 5 | SEQ ID NO: 9 |
| L1 | 24-34 or *24-34* | 24-34 or *24-34* |
| L2 | 50-56 or *50-56* | 50-56 or *50-56* |
| L3 | 89-95 or *89-95* | 89-95 or *89-95* |

Anti-GDF-8 antibodies may further comprise antibody constant regions or parts thereof. For example, a VL domain of the invention may be attached at its C-terminal end to an antibody light chain constant domain, e.g., a human Cκ or Cλ chain, preferably a Cλ chain. Similarly, an antigen-binding fragment based on a VH domain may be attached at its C-terminal end to all or part of an immunoglobulin heavy chain derived from any antibody isotype, e.g., IgG, IgA, IgE, and IgM, and any of the isotype subclasses, particularly IgG, and IgG$_4$. In exemplary embodiments, antibodies comprise C-terminal fragments of heavy and light chains of human IgG$_{1\lambda}$. Preferred DNA and amino acid sequences for the C-terminal constant fragment of the light λ chain are set forth in SEQ ID NO: 16 and SEQ ID NO: 17, respectively. Preferred DNA and amino acid sequences for the C-terminal constant fragment of IgG$_1$ heavy chain are set forth in SEQ ID NO: 18 and SEQ ID NO: 19, respectively. It is understood that, due to the degeneracy of the genetic code, DNA sequences listed in Table 1 are merely representative of nucleic acids that encode the amino acid sequences, peptides, and antibodies of interest, and are not to be construed as limiting.

Certain embodiments of the invention comprise the VH and/or VL domain of the Fv fragment of RK35. Further embodiments comprise one or more complementarity determining regions (CDRs) of any of these VH and VL domains. One embodiment comprises an H3 fragment of the VH domain of RK35. The VH and VL domains of the invention, in certain embodiments, are germlined, i.e., the framework regions (FRs) of these domains are changed using conventional molecular biology techniques to match the consensus amino acid sequences of human germline gene products. This is also known as a humanized or germlined antibody. In other embodiments, the framework sequences remain diverged from the germline. Humanized antibodies may be produced using transgenic mice that are incapable of expressing endogenous immunoglobulin heavy and light chain genes, but are capable of expressing human heavy and light chain genes.

C. Modified Antibodies and Their Fragments

A further aspect of the invention provides methods for obtaining an antibody antigen-binding domain directed against GDF-8. The skilled artisan will appreciate that the antibodies of the invention are not limited to the specific sequences of VH and VL as listed in Table 1 but also include variants of these sequences that retain antigen-binding ability. Such variants may be derived from the provided sequences using techniques known in the art. Amino acid substitutions, deletions, or additions, can be made in either the FRs or in the CDRs. While changes in the framework regions are usually designed to improve stability and reduce immunogenicity of the antibody, changes in the CDRs are usually designed to increase affinity of the antibody for its target. Such affinity-increasing changes are typically determined empirically by altering the CDR and testing the antibody. Such alterations can be made according to the methods described in, e.g., Antibody Engineering, 2nd. ed., Borrebaeck, ed., Oxford University Press, 1995.

Thus, the antibodies of the invention also include those that bind to GDF-8, interfere with GDF-8 signaling, and have mutations in the constant regions of the heavy and light chains. It is sometimes desirable to mutate and inactivate certain fragments of the constant region. For example, mutations in the heavy constant region are sometimes desirable to produce antibodies with reduced binding to the Fc receptor (FcR) and/or complement; such mutations are well known in the art. One of skill in the art will also recognize that the determination of which active fragments of the CL and CH subunits are necessary will depend on the application to which an antibody of the invention is applied. For example, the active fragments of the CL and CH subunits that are involved with their covalent link to each other will be important in the generation of an intact antibody.

The method for making a VH domain that is an amino acid sequence variant of a VH domain set out herein comprises a step of adding, deleting, substituting or inserting one or more amino acids in the amino acid sequence of the presently disclosed VH domain, optionally combining the VH domain thus provided with one or more VL domains, and testing the VH domain or VH/VL combination or combinations for binding to GDF-8, and (preferably) testing the ability of such antigen-binding domain to modulate one or more GDF-8-associated activities. The VL domain may have an amino acid sequence that is substantially as set out herein. An analogous method may be employed in which one or more sequence variants of a VL domain disclosed herein are combined with one or more VH domains.

A further aspect of the invention provides a method of preparing an antigen-binding fragment that interacts with GDF-8. The method comprises:
    (a) providing a starting repertoire of nucleic acids encoding a VH domain that either includes a CDR, e.g., CDR3, to be replaced or a VH domain that lacks a CDR, e.g., CDR3, encoding region;
    (b) combining the repertoire with a donor nucleic acid encoding a donor CDR comprising an active fragment of SEQ ID NO:2 or 6, e.g., a donor nucleic acid encoding the amino acid sequence set forth in SEQ ID NO:3 or 7, such that the donor nucleic acid is inserted into the CDR, e.g., CDR3, region in the repertoire so as to provide a product repertoire of nucleic acids encoding a VH domain;

(c) expressing the nucleic acids of the product repertoire;

(d) selecting an antigen-binding fragment that interacts with GDF-8; and (e) recovering the selected antigen-binding fragment or nucleic acid encoding it.

Again, an analogous method may be employed in which a VL CDR (e.g., L3) of the invention is combined with a repertoire of nucleic acids encoding a VL domain, which either includes a CDR to be replaced or lacks a CDR encoding region.

A coding sequence of a CDR of the invention (e.g., CDR3) may be introduced into a repertoire of variable domains lacking a CDR (e.g., CDR3), using recombinant DNA technology. For example, Marks et al. (1992) *Bio/Technology* 10:779-83, describes methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. The repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide antigen-binding fragments of the invention. The repertoire may then be displayed in a suitable host system, such as the phage display system of, e.g., WO 92/01047, so that suitable antigen-binding fragments can be selected.

Analogous shuffling or combinatorial techniques are also disclosed by Stemmer (1994) *Nature* 370:389-91, which describes a technique in relation to a β-lactamase gene but observes that the approach may be used for the generation of antibodies.

A further alternative is to generate novel VH or VL regions carrying a CDR-derived sequence of the invention using random mutagenesis of one or more selected VH and/or VL genes to generate mutations within the entire variable domain. Such a technique is described in Gram et al. (1992) *Proc. Natl. Acad. Sci. U.S.A.* 89:3576-80 by using error-prone PCR.

Another method that may be used to generate novel antibodies or fragments thereof is to direct mutagenesis to CDRs of VH or VL genes. Such techniques are disclosed in Barbas et al. (1994) *Proc. Natl. Acad. Sci. U.S.A.* 91:3809-13 and Schier et al. (1996) *J. Mol. Biol.* 263:551-67.

Similarly, one, two, or all three CDRs, may be grafted into a repertoire of VH or VL domains which are then screened for a binding partner or binding fragments for GDF-8.

A substantial portion of an immunoglobulin variable domain will comprise at least the CDRs and, optionally, their intervening framework regions from the antibody fragments as set out herein. The portion will also include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domain regions. For example, construction of antibody fragments of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example, in the production of diabodies) or protein labels as discussed in more details below.

Although the embodiments illustrated in the Examples comprise a "matching" pair of VH and VL domains, the invention also encompasses binding fragments containing a single variable domain, e.g., a dAb fragment, derived from either VH or VL domain sequences, especially VH domains. In the case of either of the single chain binding domains, these domains may be used to screen for complementary domains capable of forming a two-domain antigen-binding domain capable of binding GDF-8. This may be achieved by phage display screening methods using the so-called hierarchical dual combinatorial approach as disclosed in, e.g., WO 92/01047. In this technique, an individual colony containing either an H or L chain clone is used to infect a complete library of clones encoding the other chain (L or H) and the resulting two-chain antigen-binding domain is selected in accordance with phage display techniques, such as those described in that reference. This technique is also disclosed in Marks et al., supra.

Antibodies can be conjugated by chemical methods with radionuclides, drugs, macromolecules, or other agents, and may be made as fusion proteins comprising one or more CDRs of the invention.

An antibody fusion protein contains a VH-VL pair in which one of these chains (usually VH) and another protein are synthesized as a single polypeptide chain. These types of products differ from antibodies in that they generally have an additional functional element—the active moiety of a small molecule or the principal molecular structural feature of the conjugated or fused macromolecule.

In addition to the changes to the amino acid sequence outlined above, the antibodies can be glycosylated, pegylated, or linked to albumin or a nonproteinaceous polymer. For instance, anti-GDF-8 antibodies may be linked to one of a variety of nonproteinaceous polymers, e.g., polyethylene glycol, polypropylene glycol, or polyoxyalkylenes. The antibodies may be chemically modified, e.g., to increase their circulating half-life by covalent conjugation to a polymer. Exemplary polymers, and methods to attach them to peptides are known in the art.

In other embodiments, the antibody may be modified to have an altered glycosylation pattern (i.e., relative to the original or native glycosylation pattern). As used herein, "altered" means having one or more carbohydrate moieties deleted, and/or having one or more glycosylation sites added to the original antibody. Addition of glycosylation sites to an anti-GDF-8 antibody is accomplished by well-known methods of altering the amino acid sequence to contain glycosylation site consensus sequences. Another means of increasing the number of carbohydrate moieties on the antibodies is by chemical or enzymatic coupling of glycosides to the amino acid residues of the antibody. Removal of any carbohydrate moieties present on the antibodies may be accomplished chemically or enzymatically as known in the art.

Antibodies of the invention may also be tagged with a detectable or functional label such as $^{131}$I or $^{99}$Tc, which may be attached to antibodies of the invention using conventional chemistry known in the art. Labels also include enzyme labels such as horseradish peroxidase or alkaline phosphatase. Labels further include chemical moieties such as biotin, which may be detected via binding to a specific cognate detectable moiety, e.g., labeled avidin.

Antibodies, in which CDR sequences differ only insubstantially from those listed in Table 1, are encompassed within the scope of the invention. Insubstantial differences include minor amino acid changes, e.g., substitutions of one or two out of any five amino acids in the sequence of a CDR. Typically, an amino acid is substituted by a related amino acid having similar charge, hydrophobicity, or stereochemical characteristics. Such substitutions would be within the ordinary skills of an artisan. The structure framework regions (FRs) can be modified more substantially than CDRs without adversely affecting the binding properties of an antibody. Changes to FRs include, but are not limited to, humanizing a nonhuman derived framework or engineering certain framework residues that are important for antigen contact or for stabilizing the binding site, e.g., changing the class or subclass of the constant region, changing specific amino acid residues which might alter an effector function such as Fc receptor binding (e.g., Lund et al. (1991) *J. Immunol.* 147: 2657-62; Morgan et al. (1995) *Immunology* 86:319-24), or changing the species from which the constant region is derived. Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. In the $IgG_1$ or $IgG_2$ heavy chain, for example, such mutations may be made at amino acid residues 117 and 120 of SEQ ID NO: 19, which represents the Fc portion of IgG, (these residues correspond to amino acids 234 and 237 in the full-length sequence of IgG1 or $IgG_2$). Antibodies may also have mutations that stabilize the disulfide bond between the two heavy chains of an immunoglobulin, such as mutations in the hinge region of IgG4, as disclosed in, e.g., Angal et al. (1993) *Mol. Immunol.* 30:105-08.

The polypeptides and antibodies of the present invention also encompass proteins that are structurally different from the disclosed polypeptides and antibodies, e.g., which have an altered sequence but substantially the same biochemical properties as the disclosed polypeptides and antibodies, e.g., have changes only in functionally nonessential amino acids. Such molecules include naturally occurring allelic variants and deliberately engineered variants containing alterations, substitutions, replacements, insertions, or deletions. Techniques for such alterations, substitutions, replacements, insertions, or deletions are well known to those skilled in the art.

Antibodies of the invention may additionally be produced using transgenic nonhuman animals that are modified so as to produce fully human antibodies rather than the animal's endogenous antibodies in response to challenge by an antigen. See, e.g., PCT publication WO 94/02602. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. One embodiment of such a nonhuman animal is a mouse, and is termed the XENOMOUSE™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

Consequently, the term antibody as used herein includes intact antibodies, fragments of antibodies, e.g., Fab, F(ab')$_2$Fd, dAb and scFv fragments, and intact antibodies and fragments that have been mutated either in their constant and/or variable regions (e.g., mutations to produce chimeric, partially humanized, or fully humanized antibodies, as well as to produce antibodies with a desired trait, e.g., enhanced GDF-8 binding and/or reduced FcR binding). As such these antibodies are included in the scope of the invention, provided that the antibody binds specifically to GDF-8, interferes with GDF-8 signaling, and/or neutralizes or inhibits one or more GDF-8-associated activities.

Other protein-binding molecules may also be employed to modulate the activity of GDF-8. Such protein-binding molecules include small modular immunopharmaceutical (SMIP™) drugs (Trubion Pharmaceuticals, Seattle, Wash.). SMIPs are single-chain polypeptides composed of a binding domain for a cognate structure such as an antigen, a counter-receptor or the like, a hinge-region polypeptide having either one or no cysteine residues, and immunoglobulin CH2 and CH3 domains (see also www.trubion.com). SMIPs and their uses and applications are disclosed in, e.g., U.S. Published Patent Appln. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

The binding capacity of an antibody of the invention may be measured by the following methods: Biacore analysis, enzyme linked immunosorbent assay (ELISA), X-ray crystallography, sequence analysis and scanning mutagenesis as described in the Examples below, and other methods that are well known in the art. The ability of an antibody of the invention to neutralize and/or inhibit one or more GDF-8-associated activities may be measured by the following non-limiting list of methods: assays for measuring the proliferation of a GDF-8-dependent cell line; assays for measuring the expression of GDF-8-mediated polypeptides; assays measuring the activity of downstream signaling molecules; assays testing the efficiency of an antibody of the invention to prevent muscle disorders in a relevant animal model; assays as described in the Examples below; and other assays that are well known in the art.

A further aspect of the invention provides a method of selecting antibodies capable of binding GDF-8 and neutralizing and/or inhibiting one or more GDF-8-associated activities. The method comprises:

a) contracting a plurality of antibodies with GDF-8;
    b) choosing antibodies that bind to GDF-8;
    c) testing the ability of chosen antibodies to prevent GDF-8 from binding to the GDF-8 receptor; and
    d) selecting antibodies capable of preventing GDF-8 from binding to its receptor.

The anti-GDF-8 antibodies of the invention are also useful for isolating, purifying, and/or detecting GDF-8 in supernatants, cellular lysates, or on a cell surface. Antibodies disclosed in this invention can be used diagnostically to monitor GDF-8 protein levels as part of a clinical testing procedure. Additionally, antibodies of the invention can be used in treatments requiring the neutralization and/or inhibition of one or more GDF-8-associated activities, e.g., treatments for ALS and other muscle-related pathologies. The present invention also provides novel isolated and purified polynucleotides and polypeptides related to novel antibodies directed against human GDF-8. The genes, polynucleotides, proteins, and polypeptides of the present invention include, but are not limited to, murine and humanized antibodies to GDF-8 (e.g., RK35) and variants thereof.

D. Nucleic Acids, Cloning, and Expression Systems

The present invention further provides isolated and purified nucleic acids encoding antibodies of the present invention. Nucleic acids according to the present invention may comprise DNA or RNA and may be wholly or partially synthetic. Reference to nucleotide sequences as set out herein encompass DNA molecules with the specified sequences or genomic equivalents, as well as RNA molecules with the specified sequences in which U is substituted for T, unless context requires otherwise.

For example, the invention provides purified and isolated polynucleotides encoding the variable region of a murine antibody to GDF-8 that modulates one or more GDF-8-associated activities (e.g., neutralizes GDF-8 bioactivity) (RK35), and a humanized version of RK35. Preferred DNA sequences of the invention include genomic, cDNA, and chemically synthesized DNA sequences.

The nucleotide sequences of the invention include those that encode the light chain variable regions of mouse RK35 set forth in SEQ ID NO:4, including those that encode a leader sequence preceding the light chain variable region sequence, e.g., the nucleotide sequence set forth as SEQ ID NO:30 (nucleotides 1-60 correspond to the leader sequence, and nucleotides 61-381 correspond to SEQ ID NO:4). The nucleotide sequences of the invention also include those that encode the heavy chain variable region of RK35 set forth in SEQ ID NO:2, including those that encode a leader sequence preceding the heavy chain variable region, e.g., the nucleotide sequence set forth as SEQ ID NO:28 (nucleotides 1-57 correspond to the leader sequence, and nucleotides 58-405 correspond to SEQ ID NO:2). The nucleotide sequences of the invention also include humanized sequences of the heavy and light chain variable regions, such as those set forth in SEQ ID NOs:6 and 8, respectively. Polynucleotides of the present invention also include polynucleotides that hybridize under stringent conditions to the nucleic acid sequences set forth in SEQ ID NOs:2, 4, 6, and 8, and complements thereof, and/or encode polypeptides that retain substantial biological activity (i.e., active fragments) in the variable regions. Polynucleotides of the present invention also include continuous portions of the sequences set forth in SEQ ID NOs:2, 4, 6, and 8, comprising at least 15 consecutive nucleotides.

The amino acid sequence of the variable light chains of mouse RK35 is set forth in SEQ ID NO:5. An example of an amino acid sequence of the variable light chain domain of mouse RK35 preceded by a leader sequence is set forth as SEQ ID NO:31. The amino acid sequence of the variable heavy chains of RK35 is set forth in SEQ ID NO:3. An example of an amino acid sequence of the variable heavy chain domain of mouse RK35 preceded by a leader sequence is set forth as SEQ ID NO:29. The amino acid sequences of humanized variable heavy and light chains are set out in SEQ ID NOs:7 and 9, respectively. The amino acid sequences of the CDRs contained within the heavy chains of mouse RK35 are set forth in SEQ ID NOs:10-12 and 20-22. The amino acid sequences of the CDRs contained within the light chains of mouse RK35 are set forth in SEQ ID NOs: 13-15 and 23-25. Polypeptides of the present invention also include continuous portions of any of the sequences substantially set forth in SEQ ID NOs:3, 5, 7, 9, 10-15, and 20-25 comprising at least 5 consecutive amino acids. A preferred polypeptide of the present invention includes any continuous portion of any sequence substantially set forth in SEQ ID NOs:3, 5, 7, 9, and 10-15 retaining substantial biological activity of an antibody of the invention. In addition to those polynucleotides described above, the present invention also includes polynucleotides that encode the amino acid sequences substantially set forth in SEQ ID NOs:3, 5, 7, 9, and 10-15 or a continuous portion thereof, and that differ from the polynucleotides described above only due to the well-known degeneracy of the genetic code.

The isolated polynucleotides of the present invention may be used as hybridization probes and primers to identify and isolate nucleic acids having sequences identical to or similar to those encoding the disclosed polynucleotides. Polynucleotides isolated in this fashion may be used, for example, to produce antibodies against GDF-8 or other TGF-β family members or to identify cells expressing such antibodies. Hybridization methods for identifying and isolating nucleic acids include polymerase chain reaction (PCR), Southern hybridizations, in situ hybridization and Northern hybridization, and are well known to those skilled in the art.

Hybridization reactions can be performed under conditions of different stringencies. The stringency of a hybridization reaction includes the difficulty with which any two nucleic acid molecules will hybridize to one another. Preferably, each hybridizing polynucleotide hybridizes to its corresponding polynucleotide under reduced stringency conditions, more preferably stringent conditions, and most preferably highly stringent conditions. Examples of stringency conditions are shown in Table 3 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 3

| Condition | Hybrid | Hybrid Length (bp)[1] | Hybridization Temperature and Buffer[2] | Wash Temperature and Buffer[2] |
|---|---|---|---|---|
| A | DNA:DNA | >50 | 65° C.; 1X SSC -or- 42° C.; 1X SSC, 50% formamide | 65° C.; 0.3X SSC |
| B | DNA:DNA | <50 | $T_B$*; 1X SSC | $T_B$*; 1X SSC |
| C | DNA:RNA | >50 | 67° C.; 1X SSC -or- 45° C.; 1X SSC, 50% formamide | 67° C.; 0.3X SSC |
| D | DNA:RNA | <50 | $T_D$*; 1X SSC | $T_D$*; 1X SSC |
| E | RNA:RNA | >50 | 70° C.; 1X SSC -or- 50° C.; 1X SSC, 50% formamide | 70° C.; 0.3X SSC |
| F | RNA:RNA | <50 | $T_F$*; 1X SSC | $T_F$*; 1X SSC |
| G | DNA:DNA | >50 | 65° C.; 4X SSC -or- 42° C.; 4X SSC, 50% formamide | 65° C.; 1X SSC |
| H | DNA:DNA | <50 | $T_H$*; 4X SSC | $T_H$*; 4X SSC |
| I | DNA:RNA | >50 | 67° C.; 4X SSC -or- 45° C.; 4X SSC, 50% formamide | 67° C.; 1X SSC |
| J | DNA:RNA | <50 | $T_J$*; 4X SSC | $T_J$*; 4X SSC |
| K | RNA:RNA | >50 | 70° C.; 4X SSC -or- 50° C.; 4X SSC, 50% formamide | 67° C.; 1X SSC |
| L | RNA:RNA | <50 | $T_L$*; 2X SSC | $T_L$*; 2X SSC |
| M | DNA:DNA | >50 | 50° C.; 4X SSC -or- 40° C.; 6X SSC, 50% formamide | 50° C.; 2X SSC |

TABLE 3-continued

| Condition | Hybrid | Hybrid Length (bp)[1] | Hybridization Temperature and Buffer[2] | Wash Temperature and Buffer[2] |
|---|---|---|---|---|
| N | DNA:DNA | <50 | $T_N^*$; 6X SSC | $T_N^*$; 6X SSC |
| O | DNA:RNA | >50 | 55° C.; 4X SSC -or- 42° C.; 6X SSC, 50% formamide | 55° C.; 2X SSC |
| P | DNA:RNA | <50 | $T_P^*$; 6X SSC | $T_P^*$; 6X SSC |
| Q | RNA:RNA | >50 | 60° C.; 4X SSC -or- 45° C.; 6X SSC, 50% formamide | 60° C.; 2X SSC |
| R | RNA:RNA | <50 | $T_R^*$; 4X SSC | $T_R^*$; 4X SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[2]SSPE (1xSSPE is 0.15M NaCl, 10 mM NaH$_2$PO$_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
$T_B^*$-$T_R^*$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6(log$_{10}$Na$^+$) + 0.41(% G + C) − (600/N), where N is the number of bases in the hybrid, and Na$^+$ is the concentration of sodium ions in the hybridization buffer (Na$^+$ for 1X SSC = 0.165 M).
Additional examples of stringency conditions for polynucleotide hybridization are provided in Sambrook, et al., Molecular Cloning: A Laboratory Manual, Chs. 9 & 11, Cold Spring Harbor Laboratory Press, Cold Spring Harbor, NY (1989), and Ausubel et al., eds., Current Protocols in Molecular Biology, Sects. 2.10 & 6.3-6.4, John Wiley & Sons, Inc., herein incorporated by reference.

The isolated polynucleotides of the present invention may be used as hybridization probes and primers to identify and isolate DNAs having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least 90% sequence identity (more preferably, at least 95% identity; most preferably, at least 99% identity) with the disclosed polynucleotides.

The isolated polynucleotides of the present invention may also be used as hybridization probes and primers to identify and isolate DNAs having sequences encoding polypeptides homologous to the disclosed polynucleotides. These homologs are polynucleotides and polypeptides isolated from a different species than that of the disclosed polypeptides and polynucleotides, or within the same species, but with significant sequence similarity to the disclosed polynucleotides and polypeptides. Preferably, polynucleotide homologs have at least 50% sequence identity (more preferably, at least 75% identity; most preferably, at least 90% identity) with the disclosed polynucleotides, whereas polypeptide homologs have at least 30% sequence identity (more preferably, at least 45% identity; most preferably, at least 60% identity) with the disclosed antibodies/polypeptides. Preferably, homologs of the disclosed polynucleotides and polypeptides are those isolated from mammalian species.

The isolated polynucleotides of the present invention may also be used as hybridization probes and primers to identify cells and tissues that express the antibodies of the present invention and the conditions under which they are expressed.

Additionally, the isolated polynucleotides of the present invention may be used to alter (i.e., enhance, reduce, or modify) the expression of the genes corresponding to the polynucleotides of the present invention in a cell or organism. These "corresponding genes" are the genomic DNA sequences of the present invention that are transcribed to produce the mRNAs from which the polynucleotides of the present invention are derived.

The present invention also provides constructs in the form of plasmids, vectors, transcription or expression cassettes which comprise at least one nucleic acid of the invention as above.

The isolated polynucleotides of the present invention may be operably linked to an expression control sequence for recombinant production of the polypeptides of the present invention. Additionally one of skill in the art will recognize that the polynucleotides of the invention may be operably linked to well-known nucleotide sequences encoding the constant region for various antibody isotypes. For example, a polynucleotide of the invention that encodes a light chain variable region(s) of the invention (e.g., the sequence set forth in SEQ ID NOs:4 or 8) may be operably linked to a nucleotide sequence that encodes the constant region (or derivatives thereof) of either a κ light chain or λ light chain, such that the expression of the linked nucleotides will result in a full kappa or lambda light chain with a variable region that specifically binds to and neutralizes GDF-8. Similarly, a polynucleotide of the invention that encodes a heavy chain variable region of the invention (e.g., the sequence set forth in SEQ ID NOs:2 or 6) may be operably linked to a nucleotide sequence that encodes the constant region of a heavy chain isotype (or derivatives thereof), e.g., IgM, IgD, IgE, IgG and IgA. General methods of expressing recombinant proteins are well known in the art. Such recombinant proteins may be expressed in soluble form for use in treatment of disorders related to GDF-8 activity, e.g., muscle and bone degenerative disorders.

The recombinant expression vectors of the invention may carry additional sequences, such as sequences that regulate replication of the vector in host cells (e.g., origins of replication), tag sequences such as histidine, and selectable marker genes. The selectable marker gene facilitates selection of host cells into which the vector has been introduced. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Suitable vectors, containing appropriate regulatory sequences, including promoter sequences, terminator sequences, polyadenylation sequences, enhancer sequences, marker genes and other sequences as appropriate, may be either chosen or constructed. Vectors may be plasmids or viral, e.g., phage, or phagemid, as appropriate. For further details see, for example, Molecular Cloning: a Laboratory Manual: 2nd ed., Sambrook et al., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd ed., Ausubel et al. eds., John Wiley & Sons, 1992.

The present invention also provides a host cell that comprises one or more constructs as above. A nucleic acid encoding any CDR(H1, H2, H3, L1, L2, or L3), VH or VL domain, or antigen-binding fragment as provided herein, forms an aspect of the present invention.

The present invention also includes a method of producing a peptide by expressing the protein from the encoding nucleic acid in a host cell. Expression may be achieved by culturing recombinant host cells containing the nucleic acid under appropriate conditions.

Specific antibody fragments, VH and/or VL domains, and encoding nucleic acid molecules and vectors according to the present invention may be provided isolated and purified, e.g., from their natural environment, in substantially pure or homogeneous form, or, in the case of nucleic acids, free or substantially free of nucleic acids or genes of origin other than the sequence encoding a polypeptide with the required function.

A number of cell lines are suitable host cells for recombinant expression of the polypeptides and antibodies of the present invention. Mammalian host cell lines include, for example, COS cells, CHO cells, 293T cells, A431 cells, 3T3 cells, CV-1 cells, HeLa cells, L cells, BHK21 cells, HL-60 cells, U937 cells, HaK cells, Jurkat cells, as well as cell strains derived from in vitro culture of primary tissue and primary explants. Such host cells also allow splicing of the polynucleotides of the invention that consist of genomic DNA.

Alternatively, it may be possible to recombinantly produce the polypeptides and antibodies of the present invention in lower eukaryotes such as yeast or in prokaryotes. Potentially suitable yeast strains include *Saccharomyces cerevisiae, Schizosaccharomyces pombe, Kluyveromyces* strains, and *Candida* strains. Potentially suitable bacterial strains include *Escherichia coli, Bacillus subtilis,* and *Salmonella typhimurium.* If the polypeptides of the present invention are made in yeast or bacteria, it may be necessary to modify them by, for example, phosphorylation or glycosylation of appropriate sites, in order to obtain functional proteins. Such covalent attachments may be accomplished using well-known chemical or enzymatic methods.

The polypeptides and antibodies of the present invention may also be recombinantly produced by operably linking the isolated polynucleotides of the present invention to suitable control sequences in one or more insect expression vectors, such as baculovirus vectors, and employing an insect cell expression system. Materials and methods for baculovirus/Sf9 expression systems are commercially available in kit form (e.g., the MAXBAC® kit, Invitrogen, Carlsbad, Calif.).

Following recombinant expression in the appropriate host cells, the polypeptides and antibodies of the present invention may be purified from culture medium or cell extracts using known purification processes, such as gel filtration and ion exchange chromatography. Purification may also include affinity chromatography with agents known to bind the polypeptides and antibodies of the present invention. These purification processes may also be used to purify the polypeptides and antibodies of the present invention from natural sources.

Alternatively, the polypeptides and antibodies of the present invention may be recombinantly expressed in a form that facilitates purification. For example, the polypeptides may be expressed as fusions with proteins such as maltose-binding protein (MBP), glutathione-S-transferase (GST), or thioredoxin (TRX). Kits for expression and purification of such fusion proteins are commercially available from New England BioLabs (Beverly, Mass.), Pharmacia (Piscataway, N.J.), and Invitrogen, respectively. The polypeptides and antibodies of the present invention can also be tagged with a small epitope and subsequently identified or purified using a specific antibody to the epitope. A preferred epitope is the FLAG epitope, which is commercially available from Eastman Kodak (New Haven, Conn.).

The polypeptides and antibodies of the present invention may also be produced by known conventional chemical synthesis. Methods for chemically synthesizing the polypeptides and antibodies of the present invention are well known to those skilled in the art. Such chemically synthetic polypeptides and antibodies may possess biological properties in common with the natural purified polypeptides and antibodies, and thus may be employed as biologically active or immunological substitutes for the natural polypeptides and antibodies.

A further aspect of the present invention provides a host cell comprising nucleic acids, polypeptides, vectors, or antibodies and fragments thereof as disclosed herein. A still further aspect provides a method comprising introducing a nucleic acid of the invention into a host cell. The introduction may employ any available technique. For eukaryotic cells, suitable techniques may include calcium phosphate transfection, DEAE-Dextran, electroporation, liposome-mediated transfection and transduction using a retrovirus or another virus, e.g., vaccinia or, for insect cells, baculovirus. For bacterial cells, suitable techniques may include calcium chloride transformation, electroporation and infection using bacteriophage.

The introduction of nucleic acids may be followed by causing or allowing protein production from the nucleic acid, e.g., by culturing the host cells under conditions suitable for gene expression. Such conditions are well known in the art.

III. Methods of Treating, Ameliorating, Preventing, and Inhibiting the Progress of Bone, Adipose, Glucose Metabolism, Insulin and Muscle Disorders The involvement of GDF-8 in ALS, and the discovery of the novel antibodies of the invention, enables methods for treating, alleviating, and ameliorating GDF-8-associated disorders, e.g., muscle disorders, neuromuscular disorders, bone degenerative disorders, metabolic or induced bone disorders, glucose metabolism disorders, adipose disorders, and insulin-related disorders. In addition, the antibodies allow for diagnosing, prognosing and monitoring the progress of bone, muscle, adipose or insulin disorders by measuring the level of GDF-8 in a biological sample. In particular, the antibodies of the invention can be used to treat an individual with ALS or other muscle disorder, or in a method of distinguishing whether a patient is suffering from ALS or another muscle disorder.

The antibodies and other molecules of the present invention are useful to prevent, diagnose, or treat various medical disorders in humans or animals. The antibodies can be used to inhibit or reduce one or more activities associated with GDF-8. Most preferably, the antibodies inhibit or reduce one or more of the activities of GDF-8 relative to unbound GDF-8 activities. In certain embodiments, the activity of GDF-8, when bound by one or more anti-GDF-8 antibody is inhibited at least 50%, preferably at least 60, 62, 64, 66, 68, 70, 72, 72, 76, 78, 80, 82, 84, 86, or 88%, more preferably at least 90, 91, 92, 93, or 94%, and even more preferably at least 95% to 100% relative to a mature GDF-8 protein that is not bound by one or more of the anti-GDF-8 antibodies. Inhibition or neutralization of GDF-8 activity can be measured, e.g., in pGL3 $(CAGA)_{12}$ reporter gene assays (RGA) as described in Thies et al., supra, and in ActRIIB receptor assays as illustrated in the Examples.

The medical disorders diagnosed, prognosed, monitored, treated, ameliorated or prevented by GDF-8 antibodies are GDF-8-associated disorders, e.g., muscle or neuromuscular disorders including, e.g., muscular dystrophy (MD; including Duchenne's muscular dystrophy), amyotrophic lateral sclerosis (ALS), muscle atrophy, organ atrophy, frailty, carpal tunnel syndrome, congestive obstructive pulmonary disease, sarcopenia, cachexia, and other muscle wasting syndromes (e.g., caused by other diseases and conditions). In addition, other medical disorders that may be diagnosed, prognosed, monitored, treated, ameliorated or prevented by the GDF-8 antibodies are adipose tissue disorders such as obesity, type 2 diabetes, impaired glucose tolerance, metabolic syndromes (e.g., syndrome X), insulin resistance induced by trauma (such as burns or nitrogen imbalance), or bone degenerative diseases (e.g., osteoarthritis, osteoporosis, etc.). In preferred embodiments, the disorders that are diagnosed, prognosed, monitored, treated, ameliorated or prevented by GDF-8 antibodies are muscular or neuromuscular disorders. In a more preferred embodiment, the muscular or neuromuscular disorder that is diagnosed, prognosed, monitored, treated, ameliorated or prevented by anti-GDF-8 antibodies is either MD or ALS. In the most preferred embodiment of the invention, the muscular or neuromuscular disorder that is diagnosed, prognosed, monitored, treated, ameliorated or prevented by GDF-8 antagonists of the present invention, e.g., antibodies that inhibit GDF-8 activity, is ALS.

Other medical disorders that may be diagnosed, prognosed, monitored, treated, ameliorated or prevented by GDF-8 antagonists are those associated with a loss of bone, which include osteoporosis, especially in the elderly and/or postmenopausal women, glucocorticoid-induced osteoporosis, osteopenia, osteoarthritis, and osteoporosis-related fractures. Other target metabolic bone diseases and disorders include low bone mass due to chronic glucocorticoid therapy, premature gonadal failure, androgen suppression, vitamin D deficiency, secondary hyperparathyroidism, nutritional deficiencies, and anorexia nervosa. The antibodies are preferably used to diagnose, prognose, monitor, treat, ameliorate or prevent such disorders in mammals, particularly in humans.

The antibodies of the present invention are administered in therapeutically effective amounts. Generally, a therapeutically effective amount may vary with the subject's age, condition, and sex, as well as the severity of the medical condition in the subject. The dosage may be determined by a physician and adjusted, as necessary, to suit observed effects of the treatment. Toxicity and therapeutic efficacy of such compounds can be determined by standard pharmaceutical procedures in cell cultures or experimental animals, e.g., for determining the $LD_{50}$ (the dose lethal to 50% of a population) and the $ED_{50}$ (the dose therapeutically effective in 50% of a population). The dose ratio between toxic and therapeutic effects, i.e., the $LD_{50}/ED_{50}$, is the therapeutic index, and antibodies exhibiting large therapeutic indices are preferred.

The data obtained from cell culture assays and animal studies can be used in formulating a range of dosage for use in humans. The dosage of such compounds lies preferably within a range of circulating concentrations that includes the $ED_{50}$ with little or no toxicity. The dosage may vary within this range depending upon the form of dosage and the route of administration. For any antibody used in the present invention, the therapeutically effective dose can be estimated initially from cell culture assays. A dose may be formulated in animal models to achieve a circulating plasma concentration range that includes the $IC_{50}$ (e.g., the concentration of the test antibody which achieves a half-maximal inhibition of symptoms or half-maximal inhibition of inhibition of biological activity) as determined in cell culture. Levels in plasma may be measured, for example, by high performance liquid chromatography. The effects of any particular dosage can be monitored by a suitable bioassay. Examples of suitable bioassays include, but are not limited to, DNA replication assays, transcription-based assays, GDF-8 protein/receptor binding assays, creatine kinase assays, assays based on the differentiation of preadipocytes, assays based on glucose uptake in adipocytes, and immunological assays.

Generally, the compositions are administered so that antibodies or their binding fragments are given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg to 1 mg/kg, and 500 µg/kg to 1 mg/kg. Preferably, the antibodies are given as a bolus dose to maximize the circulating levels of antibodies for the greatest length of time after the dose. Continuous infusion may also be used before, after, or in place of the bolus dose.

IV. Methods of Identifying Therapeutic Agents

Yet another aspect of the invention provides a method of identifying therapeutic agents useful in treatment of muscle, e.g., glucose metabolism, adipose, and bone disorders. Appropriate screening assays, e.g., ELISA-based assays, are known in the art. In such a screening assay, a first binding mixture is formed by combining an antibody of the invention and its ligand, GDF-8, and the amount of binding between the ligand and the antibody in the first binding mixture ($M_0$) is measured. A second binding mixture is also formed by combining the antibody, the ligand, and a compound or agent to be screened, and the amount of binding between the ligand and the antibody in the second binding mixture ($M_1$) is measured. The amounts of binding in the first and second binding mixtures are then compared, for example, by calculating the $M_1/M_0$ ratio. The compound or agent is considered to be capable of inhibiting GDF-8 activity if a decrease in binding in the second binding mixture as compared to the first binding mixture is observed (i.e., $M_1/M_0<1$). The formulation and optimization of binding mixtures is within the level of skill in the art; such binding mixtures may also contain buffers and salts necessary to enhance or to optimize binding, and additional control assays may be included in the screening assay of the invention.

Compounds found to reduce the antibody-ligand binding by at least about 10% (i.e., $M_1/M_0<0.9$), preferably greater than about 30%, may thus be identified and then, if desired, secondarily screened for the capacity to inhibit GDF-8 activity in other assays such as the ActRIIB binding assay, or other cell-based and in vivo assays as described in the Examples or well known in the art.

V. Small Molecules

Inhibiting GDF-8 activity in an organism (or subject) afflicted with (or at risk for) a GDF-8-associated disorder, or in a cell from such an organism involved in such disorders, may also be achieved through the use of antagonist small molecules (usually organic small molecules) that antagonize, i.e., inhibit the activity of, GDF-8. Novel antagonistic small molecules may be identified by the screening methods described above and may be used in the treatment methods of the present invention described herein.

Conversely, increasing GDF-8 activity in an organism (or subject) afflicted with (or at risk for) a disorder related to decreased GDF-8 expression and/or activity or a disorder related to decreased GDF-8 levels may also be achieved through the use of small molecules (usually organic small molecules) that agonize, i.e., enhance the activity of, GDF-8. Novel agonistic small molecules may be identified by the screening methods described above and may be used in the treatment methods of the present invention described herein.

VI. Methods of Diagnosing, Prognosing, and Monitoring the Progress of Bone, Adipose, Glucose Metabolism, and Muscle Disorders In addition to treating, e.g., muscle, bone, glucose metabolism, and adipose disorders, the present invention provides methods for diagnosing such disorders by detecting the decrease or increase of GDF-8 in a biological sample, e.g., serum, plasma, bronchoalveolar lavage fluid, sputum, biopsies (e.g., of muscle), etc. "Diagnostic" or "diagnosing" means identifying the presence or absence of a pathologic condition. Diagnostic methods involve detecting the presence of GDF-8 by, e.g., determining a test amount of GDF-8 polypeptide in a biological sample from a subject (human or nonhuman mammal), and comparing the test amount with a normal amount or range (e.g., an amount or range from an individual(s) known not to suffer from such a disorder) for the GDF-8 polypeptide. While a particular diagnostic method may not provide a definitive diagnosis of ALS or other GDF-8-associated disorders, it suffices if the method provides a positive indication that aids in diagnosis.

The present invention also provides methods for prognosing ALS or other muscle disorders, or e.g., bone, glucose metabolism, and adipose disorders by detecting upregulation of GDF-8. "Prognostic" or "prognosing" means predicting the probable development and/or severity of a pathologic condition. Prognostic methods involve determining the test amount of GDF-8 in a biological sample from a subject, and comparing the test amount to a prognostic amount or range (e.g., an amount or range from individuals with varying severities of, e.g., ALS) for GDF-8. Various amounts of the GDF-8 in a test sample are consistent with certain prognoses for ALS or other GDF-8-associated disorders. The detection of an amount of GDF-8 at a particular prognostic level provides a prognosis for the subject.

The present invention also provides methods for monitoring the course of ALS or other GDF-8-associated disorders by detecting the upregulation or downregulation of GDF-8. Monitoring methods involve determining the test amounts of GDF-8 in biological samples taken from a subject at a first and second time, and comparing the amounts. A change in amount of GDF-8 between the first and second time indicates a change in the course of, e.g., severity of, ALS or other GDF-8-associated disorders. A skilled artisan will recognize that in GDF-8-associated disorders similar to ALS, e.g., where an increase in muscle mass is desirable, a decrease in amount of GDF-8 and/or GDF-8 activity between the first and second time indicates remission of the disorder, and an increase in amount indicates progression of the disorder. Such monitoring assays are also useful for evaluating the efficacy of a particular therapeutic intervention (e.g., disease attenuation and/or reversal) in patients being treated for ALS or other GDF-8-associated disorders.

The antibodies of the present invention may be used for diagnosis, prognosis or monitoring by detecting the presence of GDF-8 in vivo or in vitro. Such detection methods are well known in the art and include ELISA, radioimmunoassay, immunoblot, Western blot, immunofluorescence, immunoprecipitation, and other comparable techniques. The antibodies may further be provided in a diagnostic kit that incorporates one or more of these techniques to detect GDF-8. Such a kit may contain other components, packaging, instructions, or other material to aid the detection of the protein and use of the kit.

Where the antibodies are intended for diagnostic, prognostic, or monitoring purposes, it may be desirable to modify them, for example, with a ligand group (such as biotin) or a detectable marker group (such as a fluorescent group, a radioisotope or an enzyme). If desired, the antibodies (whether polyclonal or monoclonal) may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. Other suitable labels may include biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

VII. Pharmaceutical Compositions and Methods of Administration

The present invention provides compositions comprising a GDF-8 antagonist of the invention, i.e., polypeptides, polynucleotides, vectors, antibodies, antibody fragments, and small molecules. Such compositions may be suitable for pharmaceutical use and administration to patients. The compositions typically comprise one or more molecules of the present invention, preferably an antibody, and a pharmaceutically acceptable excipient. The anti-GDF-8 antibodies of the present invention can be used in vitro, ex vivo, or incorporated into a pharmaceutical composition when combined with a pharmaceutically acceptable carrier. As used herein, the phrase "pharmaceutically acceptable excipient" includes any and all solvents, solutions, buffers, dispersion medias, coatings, antibacterial and antifungal agents, isotonic and absorption delaying agents, and the like, that are compatible with pharmaceutical administration. Such a composition may contain, in addition to the antibodies of the invention and carrier, various diluents, fillers, salts, buffers, stabilizers, solubilizers, and other materials well known in the art. The term "pharmaceutically acceptable" means a nontoxic material that does not interfere with the effectiveness of the biological activity of the active ingredient(s). The characteristics of the carrier will depend on the route of administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

The pharmaceutical composition of the invention may be in the form of a liposome in which an antibody of the invention is combined, in addition to other pharmaceutically acceptable carriers, with amphipathic agents such as lipids that exist in aggregated form as micelles, insoluble monolayers, liquid crystals, or lamellar layers while in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone.

When applied to a combination, the term refers to combined amounts of the active ingredients that result in the therapeutic effect, whether administered in combination, serially or simultaneously.

In practicing the method of treatment or use of the present invention, a therapeutically effective amount of, e.g., an antibody that binds to GDF-8 and interferes with GDF-8 signaling is administered to a subject, e.g., mammal (e.g., a human). An antibody of the invention may be administered in accordance with the method of the invention either alone or in combination with other therapies such as anti-inflammatory agents. When coadministered with one or more agents, an antibody of the invention may be administered either simultaneously with the second agent, or sequentially. If administered sequentially, the attending physician will decide on the appropriate sequence of administering an antibody of the invention in combination with other agents.

In one embodiment, the antibodies of the invention, e.g., pharmaceutical compositions thereof, are administered in combination therapy, i.e., combined with other agents, e.g., therapeutic agents, that are useful for treating pathological conditions or disorders, such as muscle disorders, neuromuscular disorders, bone degenerative disorders, metabolic or induced bone disorders, adipose disorders, glucose metabolism disorders or insulin-related disorders, e.g., as well as allergic and inflammatory disorders. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment or in the subject.

A pharmaceutical composition of the invention is formulated to be compatible with its intended route of administration. Methods to accomplish the administration are known to those of ordinary skill in the art. It may also be possible to obtain compositions which may be topically or orally administered, or which may be capable of transmission across mucous membranes. Administration of an antibody of the invention used in a pharmaceutical composition to practice the method of the present invention can be carried out in a variety of conventional ways, such as oral ingestion, inhalation, cutaneous, subcutaneous, or intravenous injection.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor™ EL (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

When a therapeutically effective amount of an antibody of the invention is administered by, e.g., intravenous, cutaneous or subcutaneous injection, the binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agents, an isotonic vehicle such as sodium chloride injection, Ringer's injection, dextrose injection, dextrose and sodium chloride injection, lactated Ringer's injection, or other vehicle as known in the art. The pharmaceutical composition(s) of the present invention may also contain stabilizers, preservatives, buffers, antioxidants, or other additive known to those of skill in the art.

The amount of an antibody of the invention (or other antagonist of the invention) in the pharmaceutical composition of the present invention will depend upon the nature and severity of the condition being treated, and on the nature of prior treatments undergone by the patient. Ultimately, the attending physician will decide the amount of antibody with which to treat each individual patient. Initially, an attending physician administers low doses of antibody and observes the patient's response. Larger doses of antibody may be administered until the optimal therapeutic effect is obtained for the patient, and at that point the dosage is generally not increased further. It is contemplated that the various pharmaceutical compositions used to practice the method of the present invention should contain about 0.1 µg to 50 mg antibody per kg body weight.

The duration of therapy using the pharmaceutical composition of the present invention will vary, depending on the severity of the disease being treated and the condition and potential idiosyncratic response of each individual patient. It is contemplated that the duration of each application of antibody will be via, e.g., the subcutaneous route and, e.g., in the range of once a week. Ultimately the attending physician will decide on the appropriate duration of therapy using the pharmaceutical composition of the present invention.

Oral compositions generally include an inert diluent or an edible carrier. They can be enclosed in gelatin capsules or compressed into tablets. For the purpose of oral therapeutic administration, the GDF-8 antagonist (e.g., antibody, small molecule, etc.) can be incorporated with excipients and used in the form of tablets or capsules. Pharmaceutically compatible binding agents, and/or adjuvant materials can be included as part of the composition. The tablets, pills, capsules, and the like can contain any of the following ingredients, or compounds of a similar nature; a binder such as microcrystalline cellulose, gum tragacanth or gelatin; an excipient such as starch or lactose; a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

When a therapeutically effective amount of a pharmaceutical composition of the invention, e.g., an antibody that binds to GDF-8 and interferes with GDF-8 signaling, is administered orally, the binding agent will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin such as peanut oil, mineral oil, soybean oil, or sesame oil, or synthetic oils may be added (after taking into account the allergies of the individual patient and/or vast population of individuals to such liquid carriers). The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the binding agent, and preferably from about 1 to 50% the binding agent.

For administration by inhalation, a GDF-8 antagonist is delivered in the form of an aerosol spray from a pressured container or dispenser, which contains a suitable propellant, e.g., a gas such as carbon dioxide, or a nebulizer. Accordingly, the compounds described herein can be administered by inhalation to pulmonary tissue. The term "pulmonary tissue" as used herein refers to any tissue of the respiratory tract and includes both the upper and lower respiratory tract, except where otherwise indicated. One or more GDF-8 antibodies can be administered in combination with one or more of the existing modalities for treating pulmonary diseases.

In one example, the compound is formulated for a nebulizer. In one embodiment, the compound can be stored in a lyophilized form (e.g., at room temperature) and reconstituted in solution prior to inhalation.

It is also possible to formulate the compound for inhalation using a medical device, e.g., an inhaler (see, e.g., U.S. Pat. Nos. 6,102,035 (a powder inhaler) and 6,012,454 (a dry powder inhaler)). The inhaler can include separate compartments for the active compound at a pH suitable for storage and another compartment for a neutralizing buffer, and a mechanism for combining the compound with a neutralizing buffer immediately prior to atomization. In one embodiment, the inhaler is a metered dose inhaler.

Although not necessary, delivery enhancers such as surfactants can be used to further enhance pulmonary delivery. A "surfactant" as used herein refers to a compound having hydrophilic and lipophilic moieties that promote absorption of a drug by interacting with an interface between two immiscible phases. Surfactants are useful with dry particles for several reasons, e.g., reduction of particle agglomeration, reduction of macrophage phagocytosis, etc. When coupled with lung surfactant, a more efficient absorption of the compound can be achieved because surfactants, such as DPPC, will greatly facilitate diffusion of the compound. Surfactants are well known in the art and include, but are not limited to, phosphoglycerides, e.g., phosphatidylcholines, L-alpha-phosphatidylcholine dipalmitoyl (DPPC) and diphosphatidyl glycerol (DPPG); hexadecanol; fatty acids; polyethylene glycol (PEG); polyoxyethylene-9-; auryl ether; palmitic acid; oleic acid; sorbitan trioleate (Span 85); glycocholate; surfactin; poloxomer; sorbitan fatty acid ester; sorbitan trioleate; tyloxapol; and phospholipids.

Systemic administration can also be by transmucosal or transdermal means. For example, in the case of antibodies that comprise the Fe portion, compositions may be capable of transmission across mucous membranes (e.g., intestine, mouth, or lungs) via the FcRn receptor-mediated pathway (e.g., U.S. Pat. No. 6,030,613). In general, transmucosal administration can be accomplished, for example, through the use of lozenges, nasal sprays, inhalers, or suppositories. For transdermal administration, the active compounds are formulated into ointments, salves, gels, patches or creams as generally known in the art. For transmucosal or transdermal administration, penetrants appropriate to the barrier to be permeated are used in the formulation. Such penetrants are generally known in the art, and include, for example, detergents, bile salts, and fusidic acid derivatives.

Pharmaceutical compositions may also consist of compositions suitable for gene therapy, i.e., compositions comprised of the polynucleotides disclosed herein. In the case of gene therapy, the pharmaceutically acceptable carrier may include, e.g., lipids, collagen spheres, cationic emulsion systems, water, saline buffers, viral vectors, chylomicron remnants, polymer nanoparticles (e.g., gelatin-DNA or chitosan-DNA), gold particles, polymer complexes, lipoplexes, polyplexes, etc. (see, e.g., Gardlik et al. (2005) *Med. Sci. Monit.* 11 (4):RA110-21).

Stabilization and Retention

In one embodiment, a GDF-8 antibody is physically associated with a moiety that improves its stabilization and/or retention in circulation, e.g., in blood, serum, lymph, bronchopulmonary or bronchoalveolar lavage, or other tissues, e.g., by at least 1.5, 2, 5, 10, or 50 fold.

The antagonists of the invention may be prepared with carriers that will protect against rapid elimination from the body, such as a controlled-release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions containing a GDF-8 antagonist, e.g., one or more anti-GDF-8 antibodies, can also be used as pharmaceutically acceptable carriers. These can be prepared according to methods known to those skilled in the art.

For example, a GDF-8 antibody can be associated with a polymer, e.g., a substantially nonantigenic polymer, such as polyalkylene oxides or polyethylene oxides. Suitable polymers will vary substantially by weight. Polymers having molecular number average weights ranging from about 200 to about 35,000 (or about 1,000 to about 15,000, or about 2,000 to about 12,500) can be used.

For example, a GDF-8 antibody can be conjugated to a water-soluble polymer, e.g., hydrophilic polyvinyl polymers, e.g., polyvinylalcohol and polyvinylpyrrolidone. A nonlimiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides, which comprise the saccharide monomers D-mannose, D- and L-galactose, fucose, fructose, D-xylose, L-arabinose, D-glucuronic acid, sialic acid, D-galacturonic acid, D-mannuronic acid (e.g., polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g., hyaluronic acid; polymers of sugar alcohols such as polysorbitol and polymannitol; heparin, etc.

Other compounds can also be attached to the same polymer, e.g., a cytotoxin, a label, or another targeting agent, e.g., another GDF-8 antibody or an unrelated ligand. Mono-activated, alkoxy-terminated polyalkylene oxides (PAOs), e.g., monomethoxy-terminated polyethylene glycols (mPEGs), $C_{1-4}$ alkyl-terminated polymers, and bis-activated polyethylene oxides (glycols) can be used for cross-linking (see, e.g., U.S. Pat. No. 5,951,974).

In one embodiment, the polymer prior to cross-linking to the ligand need not be, but preferably is, water-soluble. Generally, after cross-linking, the product is water-soluble, e.g., exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion, aerosolization, or injection, if the conjugate is intended to be administered by such routes.

In one embodiment, the polymer contains only a single group that is reactive. This helps to avoid cross-linking of ligand molecules to one another. However, it is within the scope herein to maximize reaction conditions to reduce cross-linking between ligand molecules, or to purify the reaction products through gel filtration or ion exchange chromatography to recover substantially homogenous derivatives. In other embodiments, the polymer contains two or more reactive groups for the purpose of linking multiple ligands to the polymer backbone. Again, gel filtration or ion exchange chromatography can be used to recover the desired derivative in substantially homogeneous form.

The molecular weight of the polymer can range up to about 500,000 D, and preferably is at least about 20,000 D, or at least about 30,000 D, or at least about 40,000 D. The molecular weight chosen can depend upon the effective size of the conjugate to be achieved, the nature (e.g., structure, such as linear or branched) of the polymer, and the degree of derivatization.

A covalent bond can be used to attach a GDF-8 antibody to a polymer, for example, cross-linking to the N-terminal amino group of the ligand and epsilon amino groups found on lysine residues of the ligand, as well as other amino, imino, carboxyl, sulfhydryl, hydroxyl or other hydrophilic groups. The polymer may be covalently bonded directly to the GDF-8 antibody without the use of a multifunctional (ordinarily bifunctional) cross-linking agent. Covalent binding to amino groups is accomplished by known chemistries based upon cyanuric chloride, carbonyl diimidazole, aldehyde-reactive groups (PEG alkoxide plus diethyl acetyl of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylchloroformate activated PEG.) Carboxyl groups can be derivatized by coupling PEG-amine using carbodiimide. Sulfhydryl groups can be derivatized by coupling to maleimido-substituted PEG (e.g., alkoxy-PEG amine plus sulfosuccinimidyl 4-(N-maleimidomethyl)cyclohexane-1-carboxylate) (see WO 97/10847) or PEG-maleimide). Alternatively, free amino groups on the ligand (e.g., epsilon amino groups on lysine residues) can be thiolated with 2-imino-thiolane (Traut's reagent) and then coupled to maleimide-containing derivatives of PEG, e.g., as described in Pedley et al. (1994) *Br. J. Cancer* 70:1126-30.

Functionalized PEG polymers that can be attached to a GDF-8 antibody are available, e.g., from Shearwater Polymers, Inc. (Huntsville, Ala.). Such commercially available PEG derivatives include, e.g., amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives may vary depending on the GDF-8 antibody, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of a GDF-8 antibody and a polymer can be separated from the unreacted starting materials, e.g., by gel filtration or ion exchange chromatography, or other forms of chromatography, e.g., HPLC. Heterologous species of the conjugates are purified from one another in the same fashion. Resolution of different species (e.g., containing one or two PEG residues) is also possible due to the difference in the ionic properties of the unreacted amino acids (see, e.g., WO 96/34015).

The polynucleotides and proteins of the present invention are expected to exhibit one or more of the uses or biological activities (including those associated with assays cited below) identified herein. Uses or activities described for proteins of the present invention may be provided by administration or use of such proteins, or by administration or use of polynucleotides encoding such proteins (such as, e.g., in gene therapies or vectors suitable for introduction of DNA).

It may be advantageous to formulate oral or parenteral compositions in dosage unit form for ease of administration and uniformity of dosage. Dosage unit form as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the invention are dictated by and directly dependent on the unique characteristics of the active compound, the particular therapeutic effect to be achieved, and the limitations inherent in the art of formulating such an active compound for the treatment of individuals.

Another aspect of the present invention accordingly relates to kits for carrying out the administration of the GDF-8 antibodies of the invention, e.g., with or without other therapeutic compounds, or for using the anti-GDF-8 antibodies as a research or therapeutic tool to determine the presence and/or level of GDF-8 in a biological sample, such as an ELISA kit.

In one embodiment, the kit comprises one or more anti-GDF-8 antibodies formulated in a pharmaceutical carrier, and at least one agent, e.g., a therapeutic agent, formulated as appropriate, in one or more separate pharmaceutical preparations.

The Examples which follow are set forth to aid in the understanding of the invention but are not intended to, and should not be construed to, limit the scope of the invention in any way. The Examples do not include detailed descriptions of conventional methods, such as hybridoma formation, ELISA, proliferation assays, flow cytometric analysis and recombinant DNA techniques. Such methods are well known to those of ordinary skill in the art.

The entire contents of all references, patents, published patent applications, and other patent documents cited throughout this application are hereby incorporated by reference herein.

EXAMPLES

Example 1

Creation and Identification of Anti-GDF-8 Antibody RK35

Human GDF-8 protein (mature GDF-8 and GDF-8 propeptide) and BMP-11 protein were isolated and characterized as described in U.S. Published Patent Application No. 2004/0142382.

Six female myostatin knockout BALB/c mice (8 weeks old; McPherron et al., supra) were immunized by subcutaneous injections with 20 μg of recombinant GDF-8 dimer in Freund's complete adjuvant.

Several booster injections of the same amount of antigen in Freund's incomplete adjuvant were given at 2-week intervals and a final intravenous injection (tail vein) of 2 μg in PBS was given prior to the fusion. Splenocytes from two of the mice demonstrating the highest antibody titers were fused with mouse myeloma cells (ATCC Accession No. P3X63.Ag8.653) using standard techniques (Oi and Herzenberger (1980) In: Mishell, B. B., Shiigi, S. M., Henry, C., Mishell, R. I. (Eds.), *Selected Methods in Cellular Immunology* W.H. Freemen, San Francisco, pp. 351-72). After 10-14 days, the supernatants were harvested and screened for anti-GDF-8 antibody production by solid and solution phase ELISA (Whittemore et al., supra). Standard ELISA techniques and the pGL3-(CAGA)$_{12}$ reporter assay (Theis et al (2001) *Growth Factors* 18:251-59) were used to determine the IC$_{50}$ for inhibition of binding of myostatin to its receptor, ActRIIB, using a chimeric ActRIIB-Fc generated by fusing the extracellular domain of the human ActRIIB-Fc receptor with human IgG1 Fc region. Hybridomas chosen for further studies were rendered monoclonals by repeated limiting dilution to ensure monoclonality. Monoclonal antibody RK35 was selected for further study.

Example 2

RK35 Monoclonal Antibody has High Affinity for GDF-8 and Exhibits Neutralization Activity

Example 2.1

Experimental Procedures

For the ELISA, biotinylated GDF-8 was coated overnight at 4° C. onto 96-well streptavidin microtiter plates (Pierce, Rockford, Ill.) at 1 μg/ml. After coating, the solutions were removed from the wells, and the plates blocked for 1 hour at room temperature in SuperBlock solution (Pierce). Plates were rinsed with PBS, and 100 μl of RK35 antibody was added to the wells at various concentrations. The plates were incubated at room temperature for 1 hour and then washed with PBS. To each well, 100 μl of a 1:5000 dilution of anti-huIgG-HRP conjugate (Southern Biotech, Birmingham, Ala.) was added and the plates were incubated at room temperature for 1 hour. Each plate was washed three times with PBS. TMB substrate (100 μl) was added to each well and incubated until color development. The reaction was stopped by the addition of 100 μl of 0.18 M H$_2$SO$_4$. The signal generated was measured by reading the absorbance at 450 nm using a microtiter plate reader. Binding to GDF-8 was confirmed using human isotype control antibody.

Recombinant ActRIIB-Fc chimera (R&D Systems, Minneapolis, Minn., Cat. No. 339-RB/CF) was coated on 96-well flat-bottom assay plates (Costar, N.Y., Cat. No. 3590) at 1 μg/ml in 0.2 M sodium carbonate buffer overnight at 4° C. Plates were then blocked with 1 mg/ml bovine serum albumin and washed following standard ELISA protocol. Aliquots (100 μl) of biotinylated GDF-8 or BMP-11 were added to the blocked ELISA plate at various concentrations, incubated for 1 hr, washed, and the amount of bound GDF-8 or BMP-11 was detected by streptavidin-horseradish peroxidase (SA-HRP, BD PharMingen, San Diego, Calif., Cat. No. 13047E) followed by the addition of TMB (KPL, Gaithersburg, Md., Cat. No. 50-76-04). Colorimetric measurements were taken at 450 nm in a Molecular Devices microplate reader. To analyze the inhibitory activity, RK35 was tested at various concentrations by preincubation with 20 ng/ml GDF-8 or 20 ng/ml BMP-11. After incubation for 1 hr at room temperature, 100 μl of RK35 and GDF-8 or BMP-11 mixture was added to the plate. Detection and quantitation of bound factor is described in Whittemore et al. (2003) *Biochem. Biophys. Res. Commun.* 300:965-71.

To demonstrate the activity of GDF-8, a reporter gene assay (RGA) was developed using a reporter vector pGL3 (CAGA)$_{12}$ expressing luciferase under control of TGF-β induced promoter. The CAGA is a TGF-β-responsive sequence within the promoter of the TGF-β-induced gene PAI-1 (Denner et al. (1998) *EMBO J.* 17:3091-3100). A reporter vector containing 12 CAGA boxes was made using the basic luciferase reporter plasmid pGL3 (Promega, Madison, Wis.). The TATA box and transcription initiation site from the adenovirus major later promoter (−35/+10) was inserted between the BglII and HindIII sites. Oligonucleotides containing 12 repeats of the CAGA boxes, i.e., AGC-CAGACA, were annealed and cloned into the XhoI site. The human rhabdomyosarcoma cell line A204 (ATCC HTB-82) was transiently transfected with pGL3(CAGA)$_{12}$ using FuGENE 6 transfection reagent (Boehringer Manheim, Germany). Following transfection, cells were cultured on 96-well plates in McCoy's 5A medium supplemented with 2 mM glutamine, 100 U/ml streptomycin, 100 μg/ml penicillin and 10% fetal calf serum for 16 hrs. Cells were then treated with or without 10 ng/ml GDF-8 in McCoy's 5A medium with glutamine, streptomycin, penicillin, and 1 mg/ml bovine serum albumin for 6 hrs at 37° C. Luciferase was quantified in the treated cells using the Luciferase Assay System (Promega). To test the inhibitory activity of RK35, GDF-8 was preincubated with the antibody for 1 hr at room temperature. This mixture was then added to the transfected cells and cells were incubated for 6 hrs at 37° C. Luciferase was quantified using the Luciferase Assay System (Promega).

Example 2.2

Results

Figure 1B:
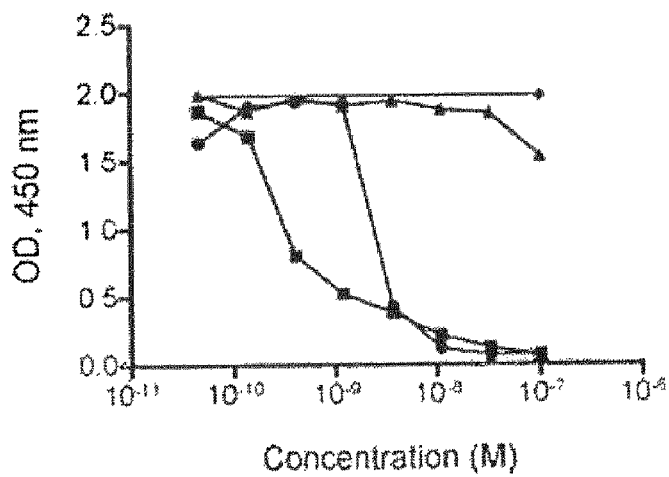
Figure 1C:
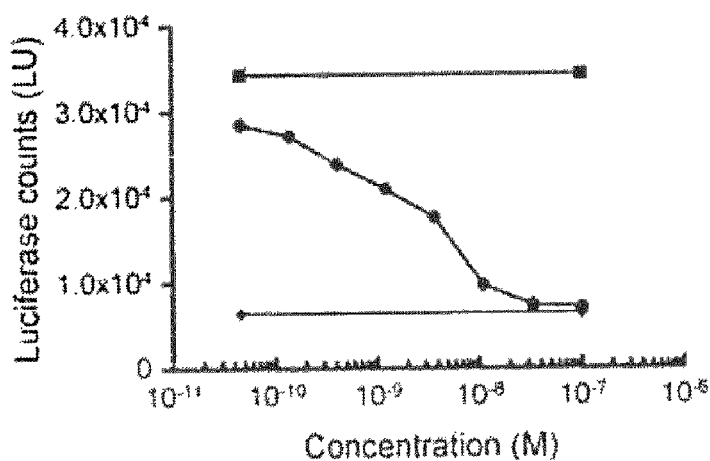

A high affinity mouse monoclonal antibody to myostatin was generated by immunizing GDF-8 knockout mice with purified recombinant human GDF-8, which is identical in amino acid sequence to mature murine myostatin (McPherron et al., 1997). The RK35 antibody bound with high affinity to GDF-8 as tested by direct ELISA (4 nM; FIG. 1A). A competition ELISA was used to assess the ability of RK35 to inhibit GDF-8 binding to its high affinity receptor, ActRIIB. RK35 blocked binding of biotinylated GDF-8 to immobilized ActRIIB-Fc with an IC50~2.5 mM (FIG. 1B). Soluble ActRIIb also blocked binding of GDF-8 to immobilized ActRIIb-Fc while control antibodies did not block binding. The neutralization activity of RK35 was also measured using a pGL3-(CAGA)12 cell based reporter assay. In this assay the luciferase gene was cloned under control of GDF-8/TGF-β responsive promoter and human A204 rhabdomyosarcoma cells were transiently transfected with the reporter plasmid. Increases in luciferase activity in A204 cells induced by GDF-8 were blocked in a dose dependent manner by RK35 (FIG. 1C). RK35 reduced the GDF-8 signal transduction activity with an IC50 of 0.2 nM. Therefore, RK35 is a new highly potent murine monoclonal neutralizing antibody directed against GDF-8.

Example 3

In Vivo Activity of RK35 in Wild Type and ALS Rodent Models

Example 3.1

Experimental Procedures

Example 3.1.1

Animals and Drug Treatment

All procedures involving animals were approved by the IACUC of either the University of Pennsylvania or Wyeth. Transgenic mice expressing human SODG93A (Gurney et al., supra) on a B6SJL hybrid background (Jackson Laboratories) were mated in-house to B6SJLF1 female breeder mice (Jackson Laboratories). Progeny were screened by PCR; mice negative for the transgene were used as aged-matched littermate wild type controls. Mice were divided into four groups: 29 SODG93A mice treated with the anti-myostatin antibody RK35, 28 SODG93A mice treated with phosphate-buffered saline (PBS) (vehicle), 23 wild type mice treated with RK35, and 23 wild type mice treated with PBS. Starting at 28 days after birth, mice were intraperitoneally injected on a weekly basis, with either anti-GDF-8 monoclonal antibody RK35 or an equivalent volume of PBS. The first dose was 40 mg/kg; subsequent doses were 20 mg/kg/week following the protocol described by for the anti-myostatin antibody JA16 (Whittemore, et al., supra). 9-12 mice from each group were sacrificed between 84 and 90 days (12 weeks) in age (mean of 88 days) to assess wet muscle mass and histology, and the remaining mice were monitored until reaching end-stage disease (~134 days), defined as a failure to right within 30 sec from both left and right lateral recumbency.

In parallel, transgenic rats (58) expressing human SODG93A (Howland et al., supra) in an equal mix of males and females were administered either PBS (vehicle) or RK35. Ten rats in each group were euthanized at 95 days in age to determine the effect of RK35 on wet muscle mass. The remaining 19 rats in each group continued through to end-stage disease. A second study using female transgenic and wild type littermate control rats was used to compare body weight increases as well as grip strength changes across treatment groups and genotype. In each study, rats were intraperitoneally injected with RK35 at 40 mg/kg (at 6 weeks (~42 days) of age) and subsequently injected with 20 mg/kg/week or vehicle continuing until either sacrifice at 95 days to analyze muscle mass, or end-stage as measured by right reflex failure.

Example 3.1.2

Body Weight and Muscle Mass Measurements

Initial body weights were used to evenly distribute animals among cohorts so as to ensure equivalent average body weights at the start of the study. Onset of weight loss was scored as the age at which the first of three consecutive measures of weight loss was observed. Wet muscle mass was determined on the gastrocnemius, the cranial tibialis, the quadriceps, and the diaphragm at a point consistent with early disease (88 days for mice, 95 days for rats) and at end-stage (~134 days for mice and ~128 days for rats). Animals were euthanized and muscles from each leg were quantitatively dissected and weighed; values from right and left legs were averaged.

Example 3.1.3

Muscle Histopathology and Motor Neuron Counts

Gastrocnemius and diaphragm were fixed and sectioned for H&E staining (Howland et al. (2002) *Proc. Natl. Acad. Sci. U.S.A.* 99:1604-29). Scoring for atrophy and hypertrophy was performed by two independent pathologists, blinded to sample identity. Fiber diameters were measured by morphometry (Axiovision 4.3, Zeiss, Thornwood, N.Y.) on gastrocnemius muscle (PBS- and RK35-treated SODG93A mice and PBS-treated wild type mice) at 88 days and end-stage, as well as for diaphragm muscle (PBS- and RK35-treated SODG93A and PBS-treated wild type mice) and end-stage. Three muscles per group were snap frozen in dry-ice-cooled isopentane, cryosectioned at a thickness of 8 μm, and immunostained using an anti-laminin antibody (Sigma, St. Louis, Mo.; catalog number L9393). Linear measurements of the maximum diameter of the minor axis of at least two hundred fibers were taken, using Zeiss Axiovision software. Fiber diameters were binned in 20 μm intervals, and frequency histograms were generated for each muscle group.

Motor neuron counts were performed on 3 mice from each group (wild type, PBS-treated SODG93A, and RK35-treated SODG93A) at both early-stage and end-stage disease (total of 18 mice analyzed). Spinal columns removed from decapitated mice were post-fixed in 4% paraformaldehyde, then cords were dissected and post-fixed for an additional 24 hours in 4% paraformaldehyde. Using MultiBrain™ technology (Neuroscience Associates, Knoxville, Tenn.), 18 lumbar spinal cords were embedded together on a single block, and cross-sectioned at 50 um in the coronal plane along the entire segment (~6 mm) of the lumbar enlargement. Every sixth section (300 μm) was stained with thionine NISSL to reveal cell bodies (Bjugn (1993) *Brain Res.* 627:25-33; Kieran et al. (2004) *Nat. Med.* 10:402-05). Counts were performed using two independent approaches. First, ten spinal cord sections encompassing L3-5 for each of 18 mice were analyzed by an observer blinded to sample identity using a Zeiss Axoplan2 at 20× and 40×. Both ventral horns from each section were counted, identifying large healthy motor neurons by the presence of visible nucleoli as described previously (Kieran et al., supra). The resulting data were represented as the average number of large motor neurons per ventral horn. Second, sections from the L3-L5 region were analyzed stereologically using a Zeiss Axioskop2 equipped with a motorized specimen stage, electronic microcator, and stereology software (Stereo Investigator (MBF Bioscience, Williston, Vt.), as described (West et al. (1991) *Anat. Rec.* 231:482-97; Schmitz and H of (2000) *J. Chem. Neuroanat.* 20:93-114; Schmitz and Hof (2005) *Neuroscience* 130:813-31); α-motor neurons were scored as neurons with a maximum projection area greater than 300 $\mu m^2$.

Example 3.1.4

Phenotypic Analysis

Grip strength measurements (Columbus Instruments, Columbus, Ohio) were performed biweekly starting 28 days after birth on both the front and hind limbs of treated and control mice (n=8-24) as described (LaMonte et al. (2002) *Neuron* 34:715-24). Transgenic and wild type rats were tested for forelimb grip strength twice weekly using a Dunnett rat grip strength meter (MJS Technology, Stevenage, Hertfordshire, England) in early disease phase (between 95 and 110 days after birth; n=10). Rats were also analyzed by rotorod (Ugo Basile, Comerio, Italy) as well as monitored for abnormalities in gait and degrees of limb mobility (data not shown).

Example 3.1.5

Electrophysiology

Electromyography (EMG) recordings and data analysis were performed blinded to genotype and treatment group. Nembutal-anesthetized rats maintained at 35-37° C. body temperature were subjected to needle EMG by inserting a concentric monopolar needle electrode (9013R0011, Medtronic, Minn., USA) into the surgically-exposed diaphragm muscle until bursts of EMG interference pattern appeared with each inspiration. Electrical signals were acquired at 20 KHz with a BIOPAC setup consisting of MP150 Data Acquisition Unit, UIM100C Universal Interface Module, EMG 10° C. Electromyography module, and the Acknowledge software (BIOPAC Systems Inc, Goleta, Calif.). The signals were first analyzed to remove 60 Hz artifact and band-pass filtered between 500 and 1000 Hz to remove movement artifacts due to breathing and to emphasize the motor-unit discharges. EMG bursts were identified by rectifying the signal, low-pass filtering at 10 Hz, and then detecting the times at which the resulting envelope was greater than its mean value. Bursts that lasted less than 100 ms were not counted, and nonburst periods that lasted less than 100 ms were counted as parts of the surrounding bursts. Finally, the spikes in the nonrectified signal were detected using a peak detection threshold set equal to three times the standard deviation of the signal amplitude during the nonburst periods. Spike burst analysis was performed with custom software written by K. C. McGill (Stanford University, CA), and the burst spike rate (Hz) for each animal computed as the mean number of spikes per burst divided by the mean burst duration.

Example 3.1.6

Data Analysis and Statistics

A two-factor-repeated measures ANOVA model was applied on body weight data as well as all grip strength data using an SAS mixed procedure. A two-factor ANOVA linear model was applied on muscle mass data using the SAS GLM procedure. Electrophysiology data was analyzed by the two sample t-test. For motor neuron count data, a generalized linear model (GLM) assuming Poisson distribution was used. Muscle fiber data were analyzed by ANOVA followed by Tukey's multiple comparison test. Comparisons were considered statistically significant when p values were less than 0.05; comparisons with $0.05<p<0.15$ were noted as trends.

Example 3.2

Results

Example 3.2.1

Figure 2A:
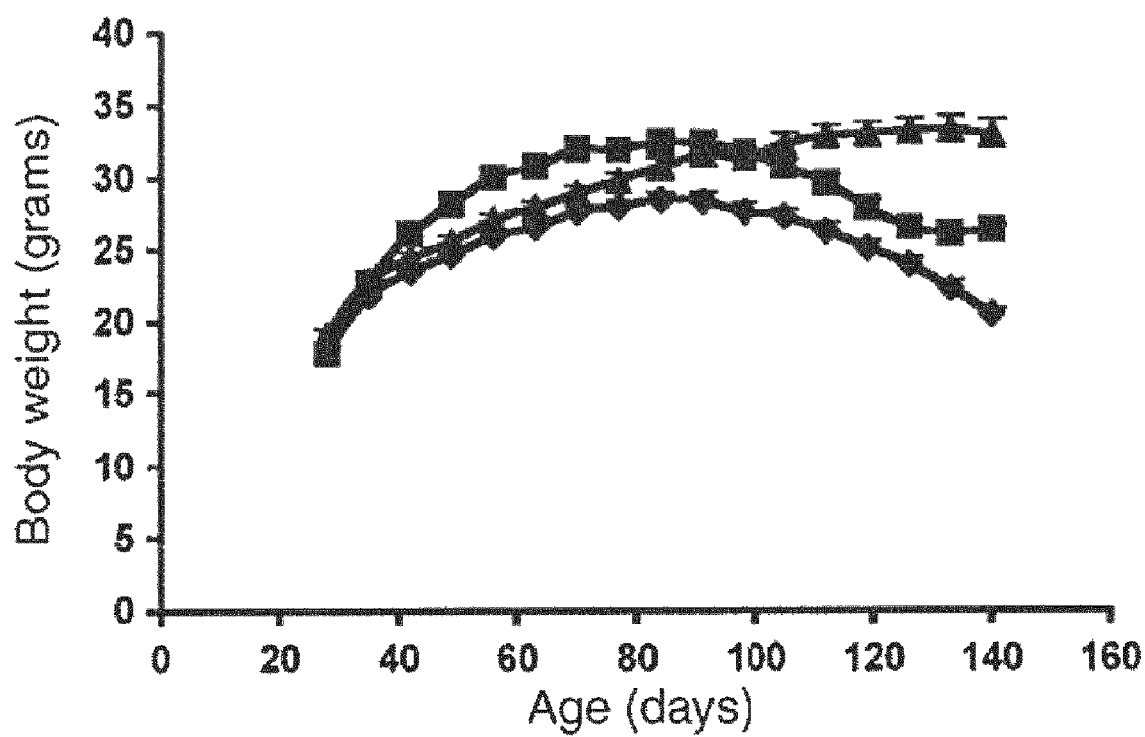
FIG. 2. Inhibition of myostatin leads to increased body weight and increased muscle mass in both SODG93A mice and rats. A. Body weights of RK35-treated (squares) (n=11) and PBS-treated (diamonds) (n=11) transgenic SODG93A mice and PBS-treated littermate control (wild type) mice (triangles) (n=9). B. Body weights of male (circles) and female (triangles) RK35-treated and male (squares) and female (diamonds) PBS-treated transgenic SODG93A rats (n=10 per group). C. Muscle mass of RK35- and PBS-treated SODG93A and PBS-treated littermate control mice (n=9-12) during early-stage disease. Wet weights were determined for the gastrocnemius (gastroc), cranial tibialis (tibialis), quadriceps (quad) and diaphragm (diaphragm) muscles from 88-day old wild type mice treated with PBS (black bars), SODG93A mice treated with PBS (white bars), and SODG93A mice treated with RK35 (grey bars). D. Muscle mass from SODG93A rats, treated with PBS (white bars) or RK35 (grey bars), at early-stage disease (~95 days) (n=7 per group). E. Muscle mass of wild type mice treated with PBS (black bars), SODG93A mice treated with PBS (white bars), and SODG93A mice treated with RK35 (grey bars) at end-stage disease (~134 days). F. Muscle mass from SODG93A rats, treated with PBS (white bars) or RK35 (grey bars) at end-stage disease (~128 days). Asterisks (*) denote statistically (p<0.05) differences between indicated groups.

RK35 Treatment Increased Body Weights of SODG93A Rodents but Did not Extend Survival SODG93A mice were treated with the anti-myostatin antibody RK35 starting 28 days after birth and continuing to end-stage disease (approximately 134 days after birth). RK35 treatment resulted in significantly increased body weight from 40 to 120 days after birth compared to PBS-treated SODG93A mice. While PBS-treated SODG93A mice reached a maximum body weight of 27.78±0.46 g at 70 days, RK35-treated mice reached a maximum of 32.13±0.48 g, a relative increase of 16% (FIG. 2A). While wild type mice continued to gain weight throughout the study, both PBS- and RK35-treated SODG93A mice began to show significant signs of weight loss due to disease progression approximately 98 days after birth.

Figure 2B:
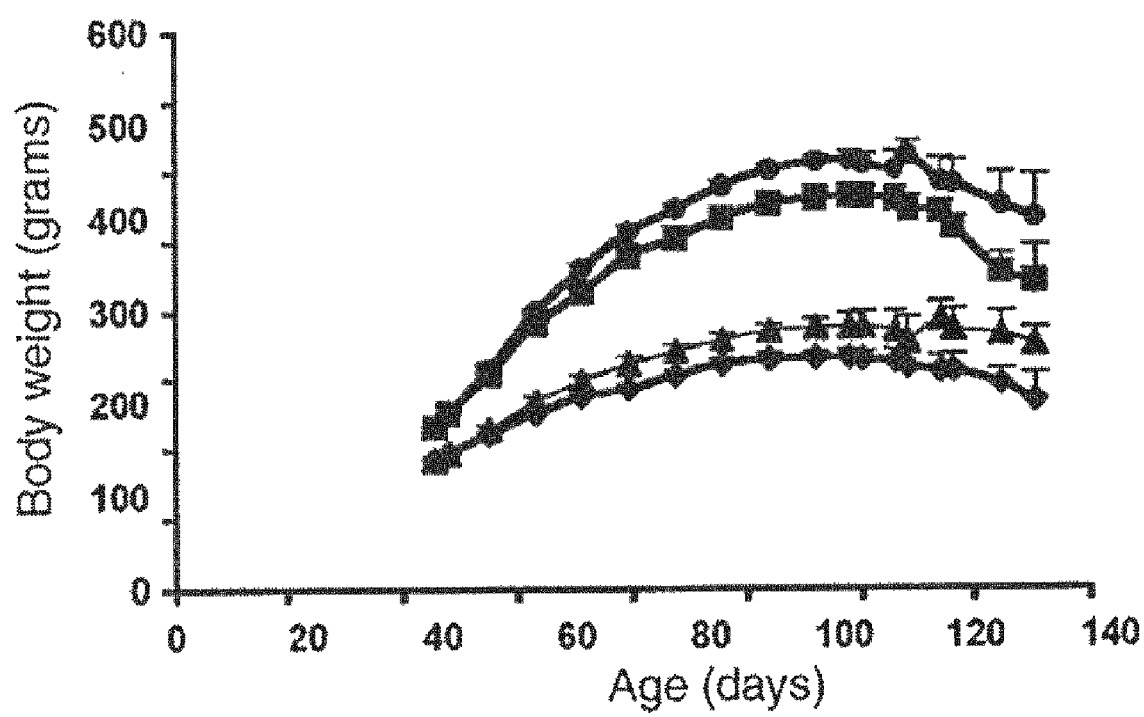

Transgenic SODG93A rats were also treated with RK35 antibody starting 42 days after birth and continuing to end-stage disease (~128 days old). Treatment with anti-myostatin RK35 led to increased body weight in SODG93A rats compared to PBS-treated rats (FIG. 2B). Transgenic rats receiving RK35 weighed significantly more than PBS-treated transgenic rats as early as 60 days after birth (p<0.05), corresponding to 3 weeks after initiation of dosing. RK35-treated male rats reached a maximum of 458.8±6.5 g at 96 days, a 10% increase over PBS-treated male rats at 419.1±10.7 g. RK35-treated females reached a maximum of 289.7±9.3 g, a 15% increase over PBS-treated females at 252.8±6.0 g. SODG93A rats treated with either PBS or RK35 began to show significant weight loss after ~112 days due to disease progression; RK35 treatment did not delay the initiation of weight loss.

While RK35 treatment led to significant increases in body weight, the inventors observed no effects of RK35 treatment on survival. Time to end-stage, as measured using the defined endpoint of failure to right within 30 seconds, was 132±8 days for RK35-treated SODG93A mice (n=16), while PBS-treated SODG93A mice reached end-stage by 134±7 days (n=17). SODG93A rats treated with RK35 reached end-stage by 125±8 days compared to 128±6 days for PBS-treated SODG93A rats. None of these differences were statistically significant, indicating that inhibition of myostatin does not delay time to end-stage disease in either mouse or rat models of ALS.

Example 3.2.2

Effects of Myostatin Inhibition on Muscle Mass and Strength

Figure 2C:
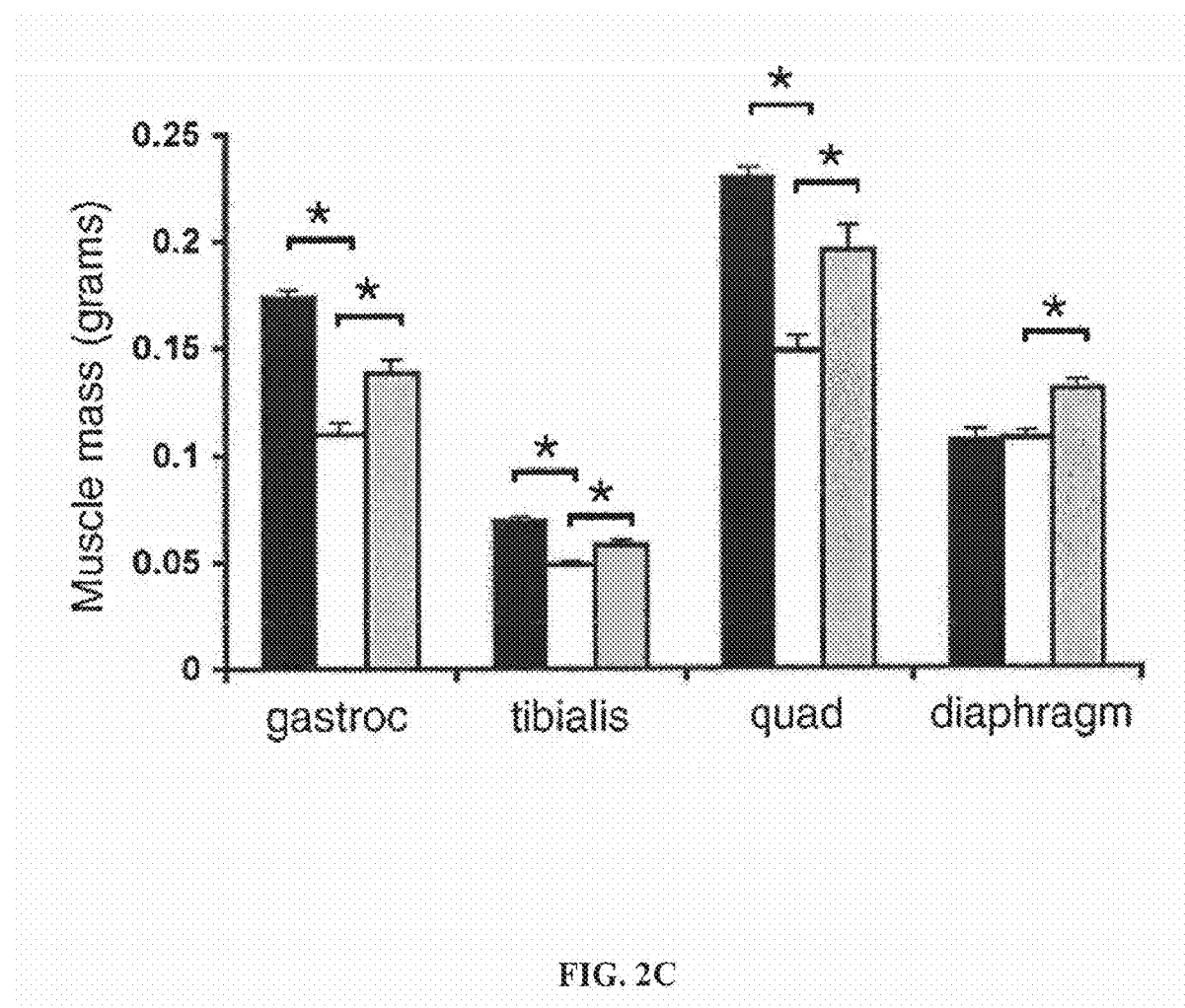

In order to determine whether myostatin inhibition slowed muscle wasting, SODG93A transgenic and wild type mice from each group were sacrificed at 88 days after birth, a time point close to the maximum increase in body weight induced by the RK35 treatment. At this time point, PBS-treated SODG93A mice show significant decreases in muscle mass in the gastrocnemius, cranial tibialis, and quadriceps relative to wild type control mice consistent with early-stage disease (FIG. 2C). In contrast, RK35-treated SODG93A mice displayed statistically significant improvements in muscle mass in all muscles examined in comparison to age-matched PBS-treated SODG93A mice at the 88-day time point ranging from ~19% to 32% (gastrocnemius muscle, +26%; cranial tibialis, +19%; quadriceps, +32%). While no significant loss of muscle mass was observed in diaphragms from PBS-treated SODG93A mice during early-stage disease; RK35 treatment induced a significant increase in mass in this muscle as well (+21%).

Figure 2D:
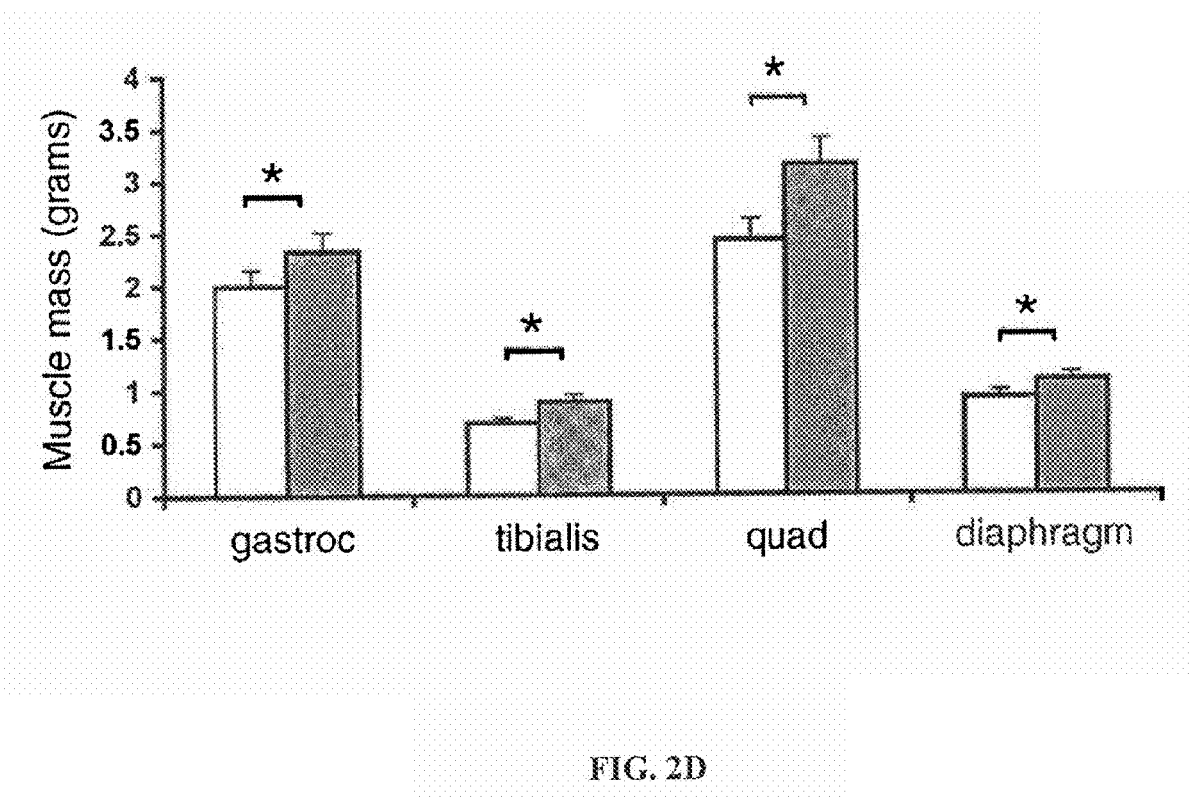
Figure 2E:
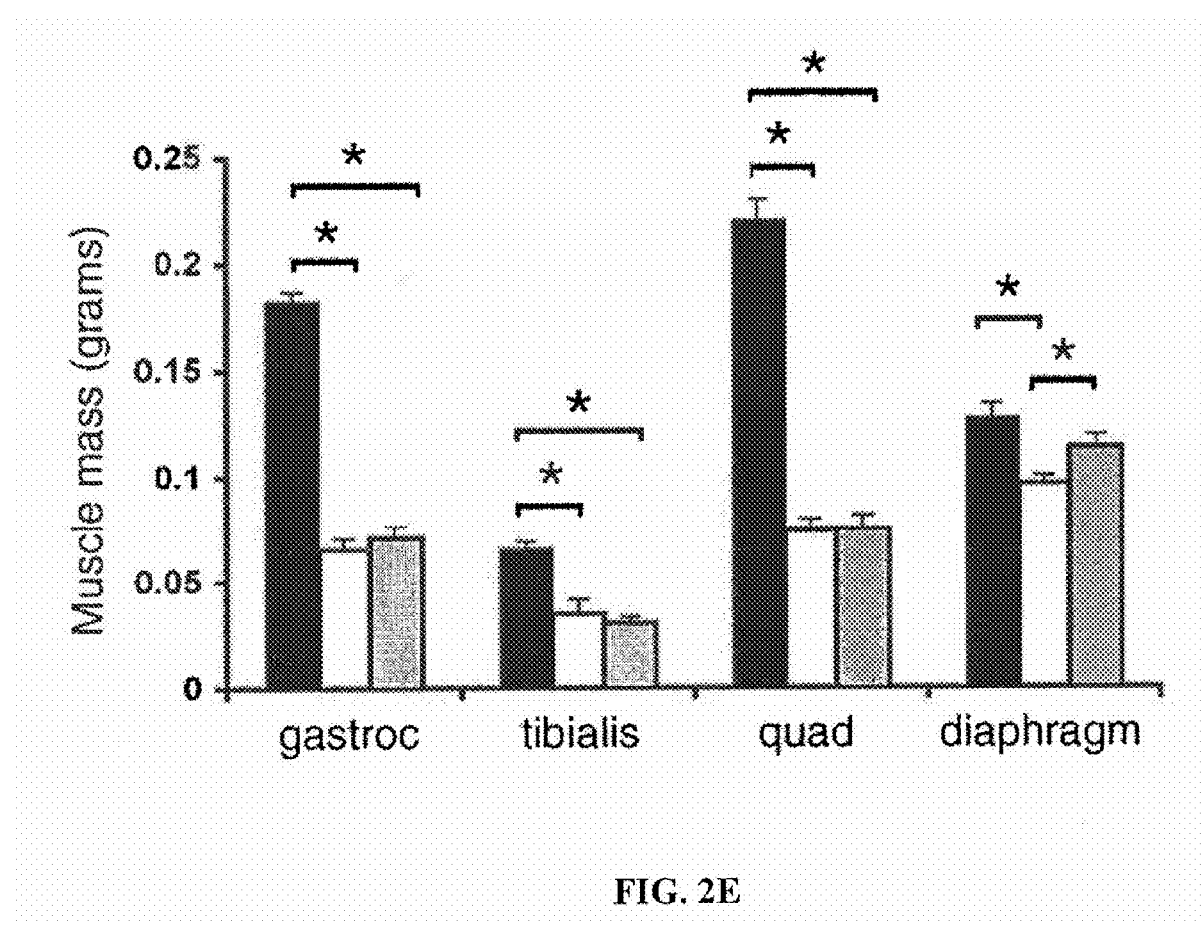

The remaining mice in each cohort were monitored until end-stage as defined by the right reflex test. At end-stage, leg muscle wasting was observed in both RK35-treated and PBS-treated SODG93A mice (FIG. 2E). In contrast to the observations on tissue from 88-day mice, at end-stage disease PBS-treated SODG93A mice showed a significant reduction in diaphragm muscle mass relative to wild type animals (FIG. 2E). However, the RK35-induced increase in diaphragm mass observed in treated SODG93A mice remained significant at end-stage, indicating that myostatin inhibition slowed atrophy of the diaphragm in the SODG93A mouse.

Figure 2F:
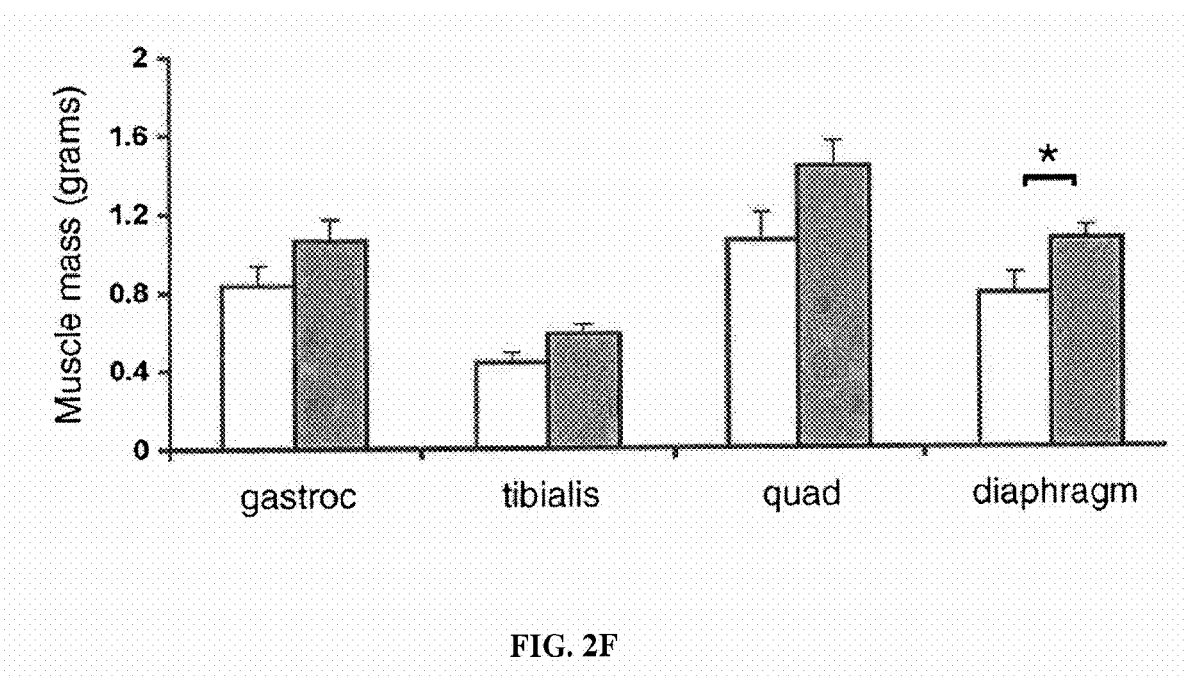

The effects of anti-myostatin antibody on muscle mass were also investigated in SODG93A rats. Similar to observations made in mice, ~95-day-old SODG93A rats treated with RK35 showed significantly increased mass over PBS-treated SODG93A rats in gastrocnemius (+17%), cranial tibialis (+30%), quadriceps (+30%) and diaphragm (+17%) muscles (FIG. 2D). By end-stage disease, leg muscle atrophy was apparent in both PBS- and RK35-treated SODG93A rats (FIG. 2F). A trend toward increased leg muscle mass as a result of RK35 treatment in the SODG93A rats persisted to end-stage, but these effects did not reach significance. However, a robust and significant 35% increase in diaphragm mass from RK35-treated SODG93A rats over PBS-treated controls (~35%) was still evident at end-stage disease (FIG. 2F), in agreement with the observations seen with the SODG93A mice (FIG. 2E).

Figure 3A:
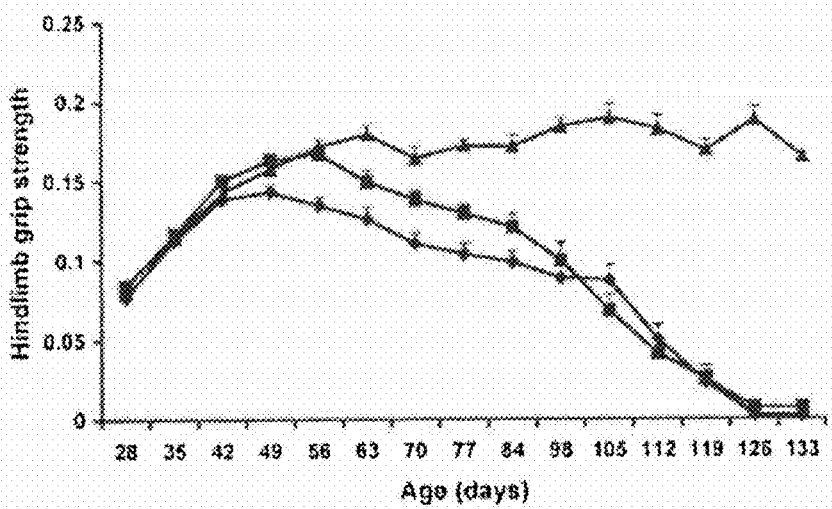
FIG. 3. Myostatin inhibition enhances muscle strength in SODG93A mice and rats. A. Hindlimb grip strength in PBS-treated wild type mice (triangles), and SODG93A mice treated with either PBS (diamonds) or RK35 (squares) as a function of age. Hind limb grip strength is expressed as compression in kilograms (kg). B. Forelimb grip strength in PBS-treated wild type mice (triangles), and SODG93A mice treated with either PBS (diamonds) or RK35 (squares) as a function of age. C. Forelimb grip strength in wild type rats treated with PBS (WT+PBS), or SODG93A rats treated with PBS (SOD+PBS) or RK35 (SOD+RK35). For rats, measurements were taken during a 4-week interval corresponding to early disease phase, between 95-110 days in age. Forelimb grip strength is expressed as tension in kilograms (kg). Asterisks (*) denote a statistically significant difference (p<0.0001) between indicated groups.
Figure 3B:
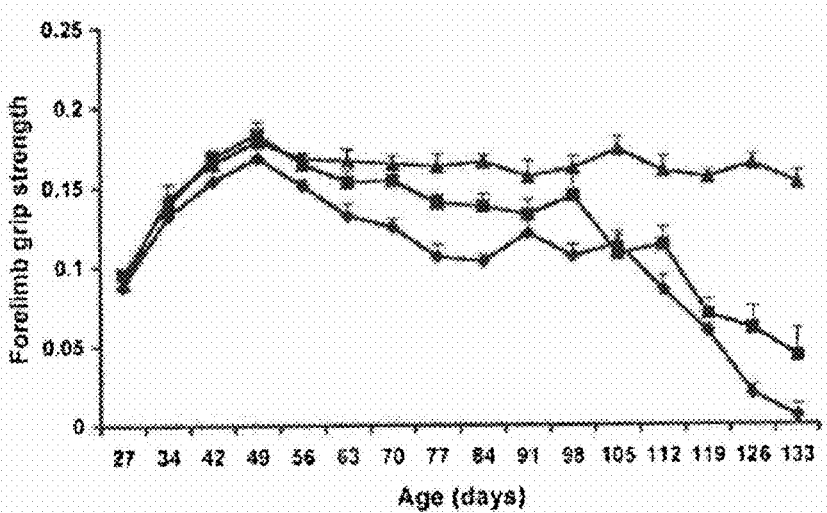

In order to test the effects of myostatin inhibition on muscle function, quantitative grip strength assays on RK35 and PBS-treated mice were performed. Both RK35-treated and PBS-treated SODG93A mice showed developmental increases in hind limb grip strength between 28 and 56 days after birth. By 56 days after birth, PBS-treated SODG93A mice become significantly weaker than age-matched control mice (FIG. 3A) ($p<0.0001$). While declines in grip strength were also apparent in RK35-treated SODG93A mice by 63 days after birth, the RK35-treated mice remained significantly stronger (or tended toward stronger) than PBS-treated SODG93A mice from 49 to 88 days after birth ($p<0.05$). Analysis of forelimb grip strength showed a similar pattern (FIG. 3B). Peak forelimb strength in both PBS- and RK35-treated SODG93A mice was observed by ~49 and 56 days after birth, respectively. PBS-treated SODG93A mice became significantly weaker than wild type animals by 56 days after birth ($p<0.05$) and continued to decline thereafter. RK35-treated SODG93A mice were stronger than PBS-treated SODG93A mice from 56 to 88 days in age (56d; $p=0.08$; 63d: $p=0.06$; 70-88d; $p<0.001$). These data indicate that myostatin inhibition slows loss of muscle function through early-stage disease in the SODG93A mice. However, after ~100 days, declines in grip strength were similar in both treated and untreated SODG93A mice.

Figure 3C:
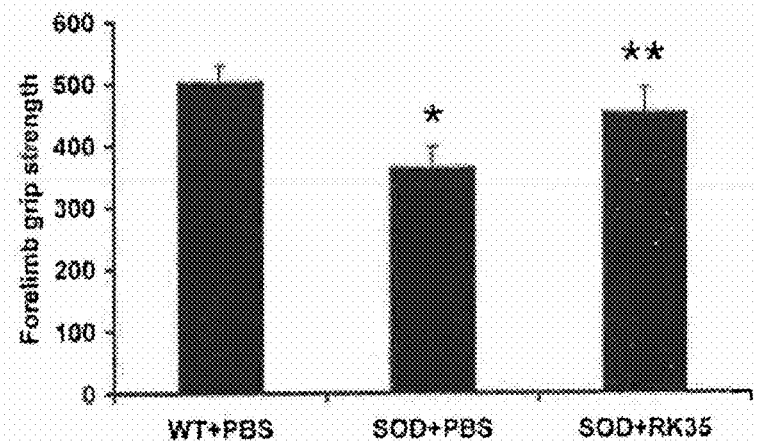

To determine if RK35 treatment induced similar changes in SODG93A rats, forelimb grip strength was also analyzed in RK35 and PBS-treated SODG93A rats and age matched wild type littermates during early-stage disease (FIG. 3C). PBS-treated SODG93A rats were significantly weaker than wild type controls, confirming that SODG93A rats also exhibit an early disease phase that precedes overt motor deficits and weight loss in a manner similar to mice. Grip strength measurements of RK35-treated SODG93A rats were generally lower than those of PBS-treated wild type rats, although the groups were not significantly different. Myostatin inhibition in SODG93A rats did significantly improve grip strength when compared to PBS-treated SODG93A rats at this age interval.

Example 3.2.3

Myostatin Inhibition Slowed the Degeneration of Limb Muscles and Diaphragm in SODG93A Mice and Rats The effects of RK35 treatment on muscle morphology were also examined. Diaphragm and medial gastrocnemius muscle from 88 day (early-stage disease) and ~134 day (end-stage disease) SODG93A mice were examined, comparing the effects of RK35 treatment with PBS, in parallel with tissue from age-matched wild type controls. The degree of atrophy and hypertrophy in each tissue was scored in a blinded analysis (0, none; 1, slight; 2, mild; 3, moderate; 4, marked; 5, severe) as shown in Table 4. PBS-treated SODG93A mice showed significant atrophy of gastrocnemius at early-stage disease (mean score of 2.0; and FIG. 4B). The observed shrinkage of muscle fibers, centrally placed nuclei and chromatin-condensed nuclei were consistent with muscle undergoing active denervation; there was also evidence of inflammation compared to wild type mice (FIGS. 4A and B). In contrast, the gastrocnemius from early-stage SODG93A mice treated with RK35 (FIG. 4C) showed little to no atrophy (Table 4; mean score of 0.3). These results support the muscle mass data indicating that atrophy of the skeletal leg muscle in early phase disease (88 days after birth) in the SODG93A mice is significantly reduced by myostatin inhibition.

Examination of gastrocnemius from end-stage SODG93A mice confirmed moderate muscle atrophy in both PBS (Table 4; mean score of 3.0) and RK35 treated (Table 4; mean score of 3.3) (FIGS. 4E and F) groups with no degenerative signs in wild type muscle (FIG. 4D). These results are consistent with the muscle mass data, indicating that the protective effects of myostatin inhibition in early disease do not persist through end-stage disease in SODG93A mice.

The diaphragm from either PBS-treated or RK35-treated SODG93A mice showed little to no atrophy (Table 4; mean scores of 0.6) compared to wild type mice at 88 days. By end-stage, however, mild to moderate atrophy was observed in diaphragm from PBS-treated SODG93A mice (FIG. 4H; Table 4; mean score of 2.3). In contrast, diaphragm from RK35-treated SODG93A mice analyzed at end-stage disease showed no significant signs of atrophy compared to PBS-treated SODG93A animals (Table 4; compare FIGS. 4H and 4I), similar to diaphragm from age-matched wild type mice (FIG. 4G). Taken together, the muscle mass and histological assessment indicate that myostatin inhibition by RK35 preserves diaphragm but not skeletal leg muscle integrity through end-stage of disease.

TABLE 4

Summary of muscle pathology observed in SODG93A mice treated with PBS or RK35, in comparison with age-matched wild type control mice.

| | genotype: | | | | | |
|---|---|---|---|---|---|---|
| | G93A | G93A | WT | G93A | G93A | WT |
| RK35: | − | + | − | − | + | − |
| Age: | 88 d | 88 d | 88 d | 134 d | 134 d | 134 d |
| # mice: | 3 | 3 | 3 | 3 | 3 | 3 |
| gastrocnemius | | | | | | |
| hypertrophy | 0 | 0 | 0 | 0 | 0 | 0 |
| atrophy | 2 | 0.3 | 0 | 3.0 | 3.3 | 0 |
| diaphragm | | | | | | |
| hypertrophy | 0 | 0.6 | 0 | 0 | 1.7 | 0 |
| atrophy | 0.6 | 0.6 | 0 | 2.3 | 0 | 0 |

Scoring:
0, none;
1, slight;
2, mild;
3, moderate;
4, marked;
5, severe

Figure 5A:
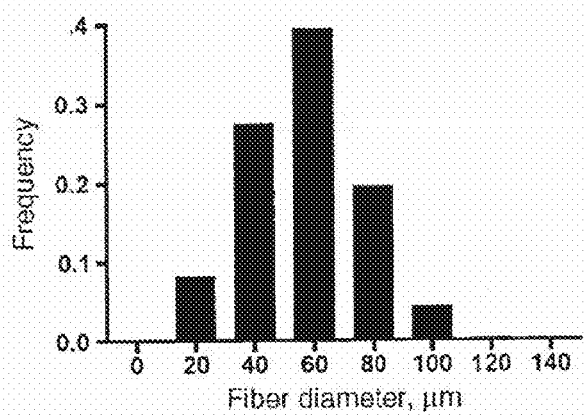
FIG. 5. RK35 treatment slows the decrease in muscle fiber diameter in gastrocnemius muscle through early-stage disease in SODG93A mice, and in diaphragm through end-stage disease. Fiber diameters were measured by morphometry on gastrocnemius muscle from PBS-treated (A) and RK35-treated (B) SODG93A mice and PBS-treated wild type mice (C) at 88 days. Means were significantly different by ANOVA (p<0.0001); pairwise comparisons by Tukey's multiple comparison post-test were also significant (p<0.001). By end-stage, no significant differences in fiber distribution were observed in the gastrocnemius muscle of PBS-treated and RK35-treated SODG93A mice (data not shown). D. Analysis of fiber diameters of diaphragm muscle from end-stage PBS-treated and RK35-treated SODG93A mice in comparison to age-matched wild type control mice. Diaphragm muscle from RK35-treated SODG93A mice shows a fiber diameter distribution intermediate between PBS-treated SODG93A mice and wild type control mice at end-stage. Means were significantly different by ANOVA (p<0.0001); pairwise comparisons by Tukey's multiple comparison post-test were also significant (p<0.01). Three muscles per group were analyzed; linear measurements of the maximum diameter of the minor axis of at least two hundred fibers were taken, using Zeiss Axiovision software. Fiber diameters were binned in 20 µm intervals, and frequency histograms were generated for each muscle group.
Figure 5B:
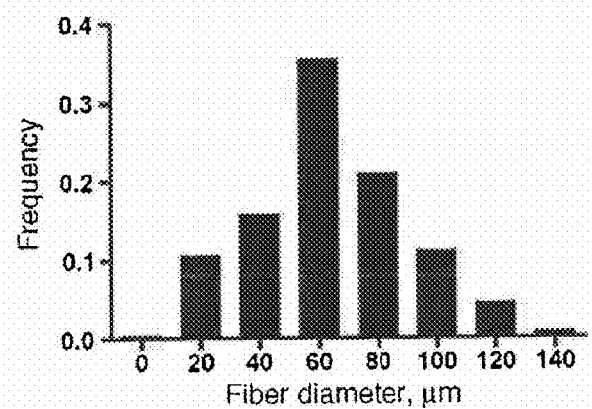
Figure 5C:
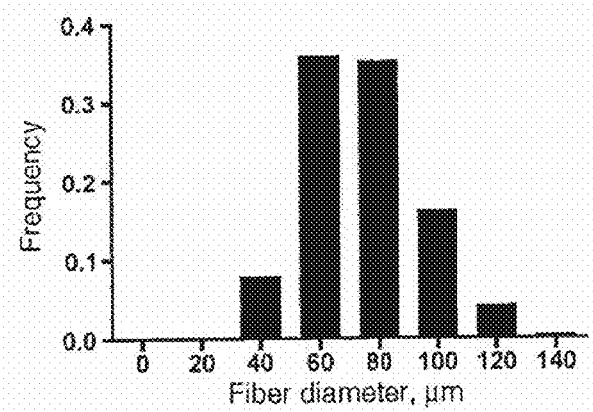
Figure 5D:
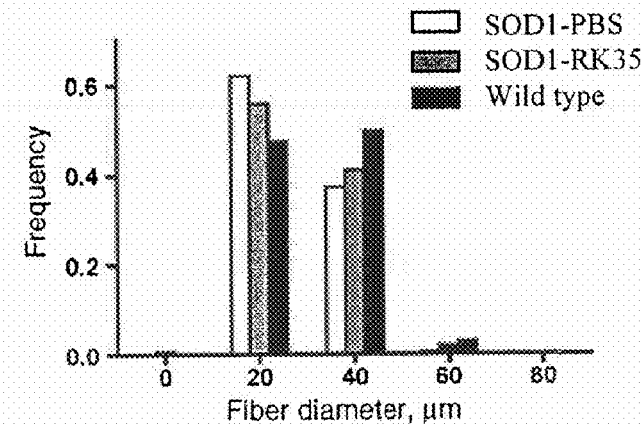

Analysis of muscle fiber size in gastrocnemius and diaphragm muscle showed a similar pattern. Frequency distributions of fiber diameter measurements from 88-day gastrocnemius muscle show a shift toward smaller fibers in SODG93A mice (FIG. 5A) in comparison to wild type control mice (FIG. 5C). The distribution of fiber diameters from RK35-treated SODG93A mice (FIG. 5B) is intermediate between untreated SODG93A mice and wild type mice during early-stage disease. By end-stage, however, average fiber diameter in the gastrocnemius muscle of RK35-treated SODG93A mice did not differ significantly from PBS-treated SODG93A mice (data not shown). Average fiber diameters in the gastrocnemius muscle from both RK35-treated and PBS-treated SODG93A mice were significantly different than wild type at end-stage, consistent with the marked muscle atrophy observed by histology. Significant differences in fiber size between wild type and PBS-treated SODG93A mice were also evident at end-stage in diaphragm muscle. Diaphragm muscle fiber size from RK35-treated SODG93A mice showed a significant shift in average fiber diameter, leading to a size distribution intermediate between wild type and PBS-treated SODG93A mice (FIG. 5D).

Figure 4J:
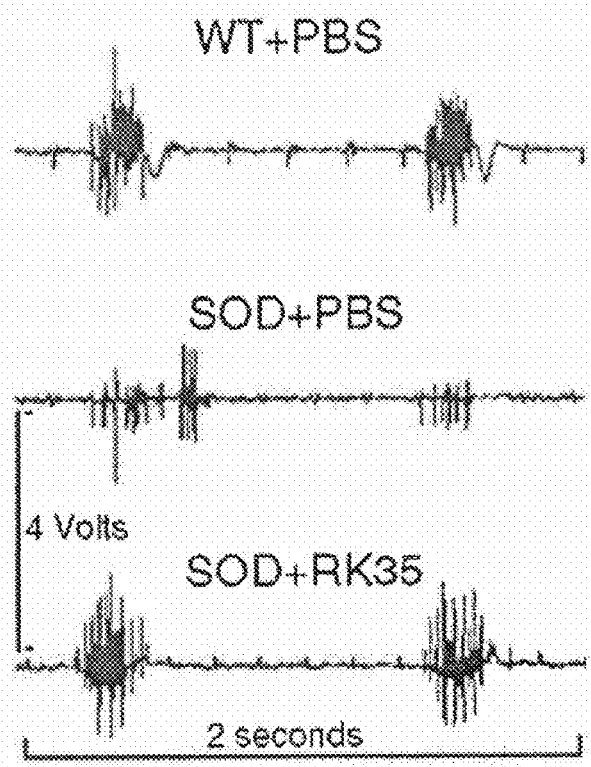
FIG. 4. Effects of myostatin inhibition on muscle structure and function in SODG93A rodents. Hematoxylin and eosin staining of medial gastrocnemius muscle from mice at 88 days indicates significant atrophy in (B) PBS-treated SODG93A mice, in comparison to either (A) wild type or (C) RK35-treated SODG93A mice. Hematoxylin and eosin staining of medial gastrocnemius muscle from both (E) PBS-treated and (F) RK35-treated SODG93A mice at end-stage indicates both significant muscle atrophy and centrally placed nuclei (arrowheads) compared to (D) wild type mouse gastrocnemius. Hematoxylin and eosin staining of diaphragm from (G) PBS-treated wild type mice and (H) PBS- or (I) RK35-treated SODG93A mice, respectively, at end-stage. Examples of atrophic myofibers are marked ("a"). The asterisk in panel H denotes fiber splitting. Bars shown denote 50 µm in scale in panels A-F and 25 µm in panels G-I. Panel J: EMG interference pattern showing inspiratory bursts, recorded from the diaphragm muscles of wild type rats treated with PBS (WT+PBS) or SODG93A rats treated with PBS (SOD+PBS) or RK35 (SOD+RK35). Panel K: EMG burst spike rates (in Hz) from the diaphragm muscles of wild type rats (n=4), and from SODG93A rats treated either with vehicle (PBS, n=9) or RK35 (n=8). Asterisks (*) denote a statistically significant difference (p<0.05) between the indicated groups.
Figure 4K:
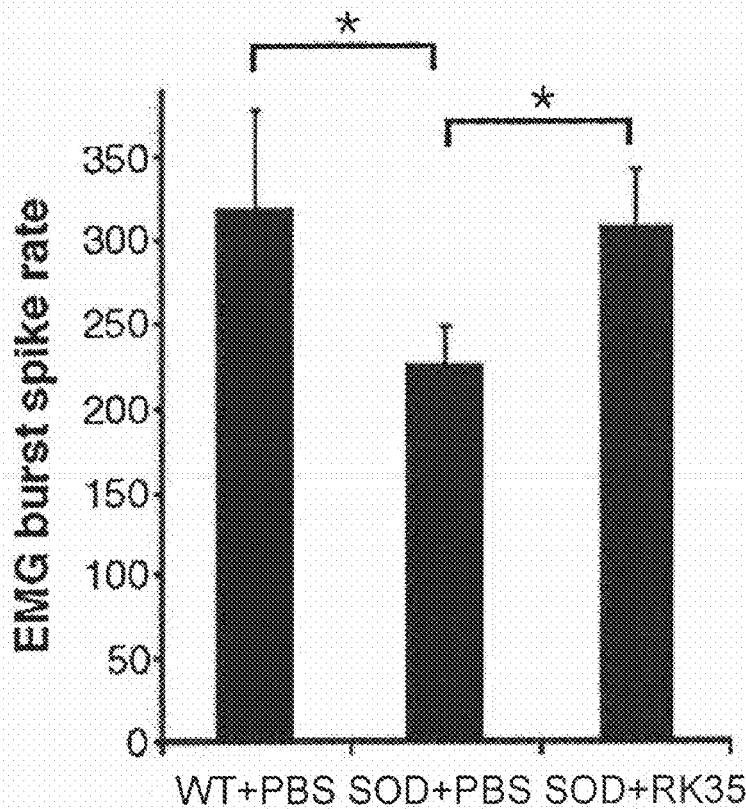

The effects of SODG93A expression on the electrical activity of the diaphragm muscle (FIGS. 4J and 4K) were next examined using the rat model at a time corresponding to clinical onset (~12 days; Howland et al. (2002) Proc. Natl. Acad. Sci. U.S.A. 99:1604-09). The EMG shown for the PBS-treated SODG93A rat group shows sparse spike activity as well as some presence of abnormal spontaneous activity (FIG. 4J). Spike activity of SODG93A rats treated with RK35 was similar to that observed for wild type rats, with no evidence of abnormal spontaneous activity. As shown in FIG. 4K, diaphragm muscle from transgenic SODG93A rats showed a statistically significant decrease in EMG burst spike rates indicative of impaired function. In contrast, SODG93A rats treated with RK35 showed a burst spike rate that was significantly higher than the PBS-treated SODG93A rats, and which was not significantly different from age-matched wild type controls. Therefore, myostatin inhibition by RK35 was effective in preserving both diaphragm structure and diaphragm function.

Example 3.2.4

Myostatin Inhibition Slows Loss of Motor Neurons in the Ventral Horn

To determine whether RK35 slowed the loss of large motor neurons in spinal cord, large motor neurons in lumbar L3-5 mouse spinal cord from SODG93A mice treated with RK35 or PBS and wild type mice treated with PBS were counted. Counts were performed on spinal cord at 12 weeks (84-90 days in age; mean of 88 days), a time when RK35 treatment resulted in increased muscle mass, increased body weight, increased grip strength and attenuated muscle histopathology in SODG93A mice. At this time, there is significant loss (25-40%) of large motor neurons in the SODG93A mouse (Guo et al. (2003) Hum. Mol. Genet. 12:2519-32; Sharp (2005) Neuroscience 130:897-910; Schutz et al. (2005) J. Neurosci. 25:7805-12).

Figure 6A:
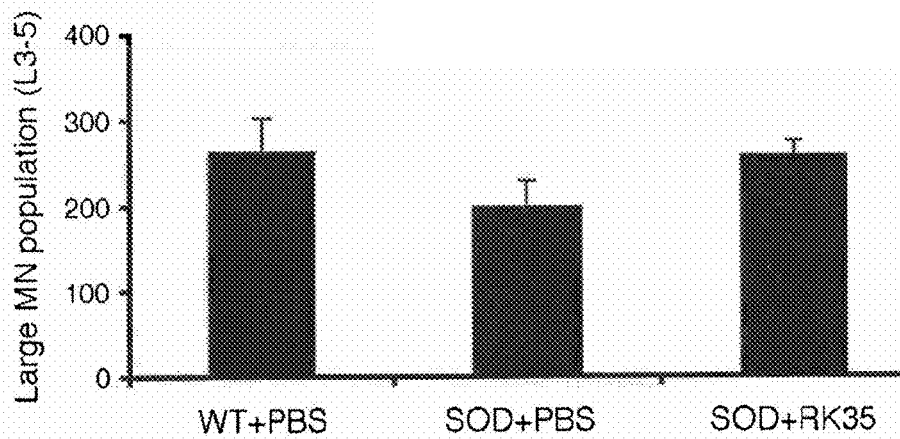
FIG. 6. Effect of anti-myostatin treatment on motor neuron loss in the ventral horn of the spinal cord. Shown are stereological analyses of large motor neurons (area greater than 300 µm$^2$) from the L3-5 regions of the ventral horn from SODG93A mice treated with either PBS (SOD+PBS) or RK35 (SOD+RK35) at early-stage (A) and end-stage (C) disease in comparison to age-matched wild type mice (WT+PBS). RK35 treatment showed a trend towards reversing the motor neuron loss (p=0.08) in early-stage disease (A). Individual counts of large healthy motor neurons with visible nucleoli were performed on NISSL-stained sections L3-5 from SODG93A mice treated with either PBS or RK35 at (B) early-stage and (D) end-stage disease in comparison to age-matched wild type mice. For each section, both ventral horns were counted (total of 20 ventral horns per animal) and data are represented as average number of large motor neurons per ventral horn. Asterisks (*) denote statistically significant differences (P<0.001) between the indicated groups. Representative images from NISSL-stained ventral horn sections (20× magnification) are shown for (E and H) wild type mice treated with PBS, (F and I) SODG93A mice treated with PBS, and (G and J) SODG93A mice treated with RK35 analyzed at early (88 days) (E-G) and end-stage disease (134 days; H-J). Bar denotes scale of 200 µm.
Figure 6B:
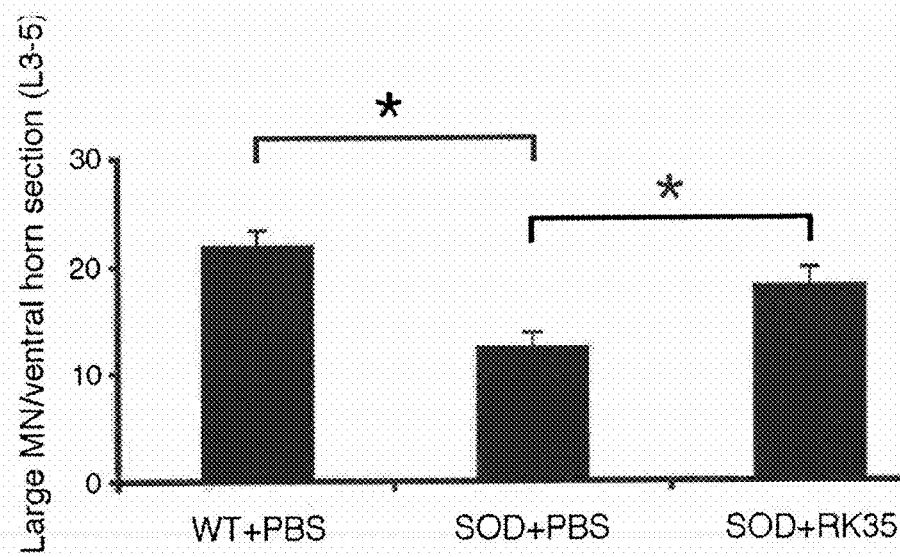
Figure 6C:
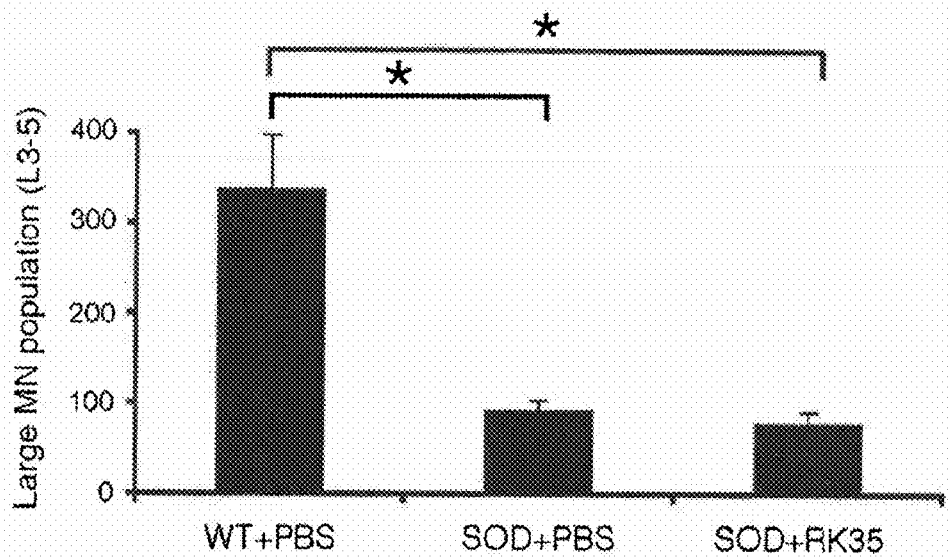
Figure 6D:
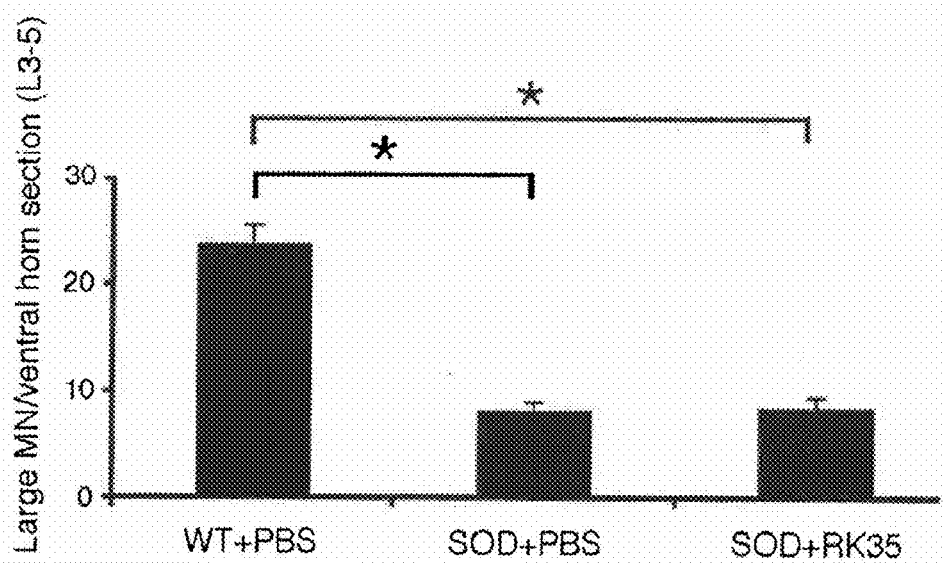
Figure 6E:
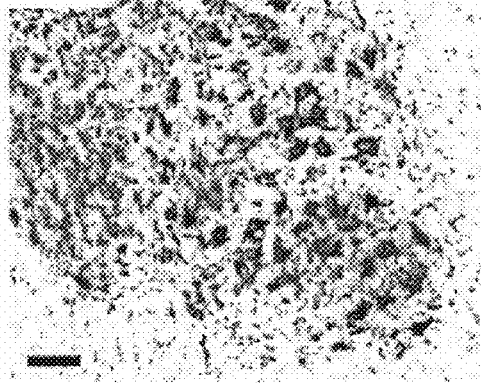

Counts of large lumbar motor neurons (FIGS. 6A-D) in PBS-treated SODG93A mice (FIG. 6F) decreased significantly compared to littermate wild type controls (FIG. 6E). RK35 treatment reduced the loss of motor neurons at early-stage disease (FIG. 6G) to a level intermediate between PBS-treated SODG93A mice and wild type mice.

Figure 6H:
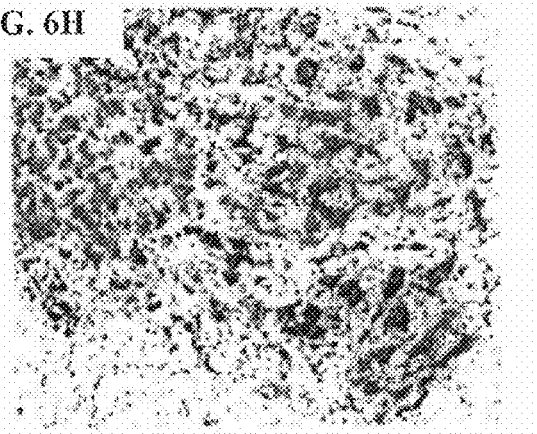
Figure 6F:
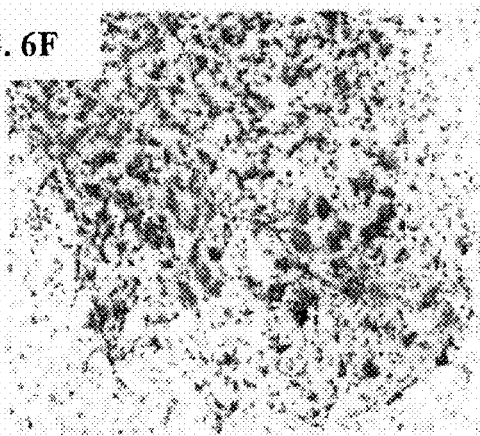
Figure 6I:
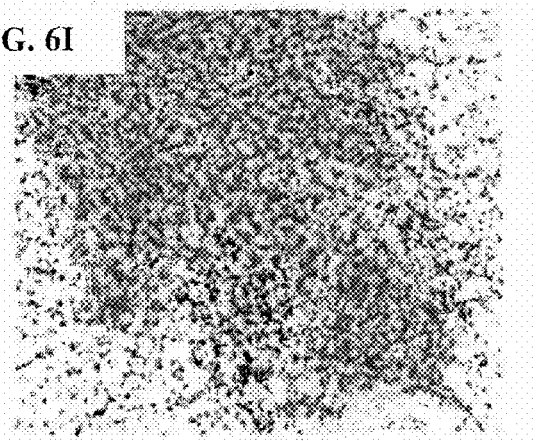
Figure 6G:
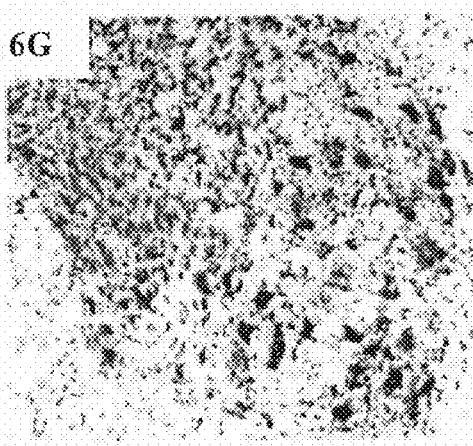
Figure 6J:
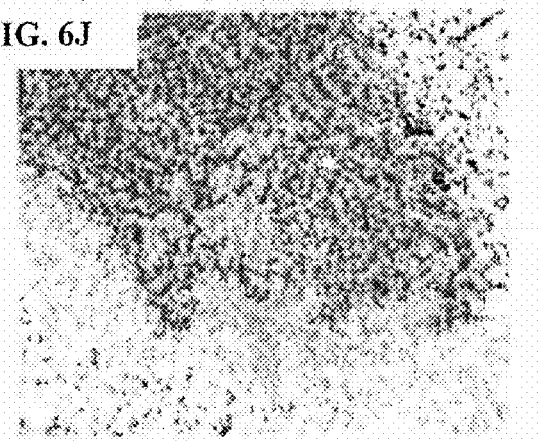

By end-stage disease, significant losses of large motor neurons in the lumbar ventral horn as well as increased gliosis were evident in the SODG93A mice regardless of treatment (FIGS. 6I and J) with no corresponding changes noted in wild type mice (FIG. 6H).

Stereological counting of the total population of large motor neurons (area greater than 300 $\mu m^2$) revealed a trend of 25% motor neuron loss in PBS-treated SODG93A mice in comparison to wild type controls. A trend toward a slowing of motor neuron loss was observed in mice treated with RK35 (p=0.08) (FIG. 6A). If counts were restricted to large motor neurons with visible nucleoli to avoid counting motor neurons showing signs of degeneration (i.e., presence of irregular membrane and vacuoles), there is a 40% decrease in the average number of large motor neurons per section in PBS-treated SODG93A mice in comparison to wild type control mice (FIG. 6B), as well as a statistically significant difference between RK35-treated and PBS-treated SODG93A mice (FIG. 6B). Taken together, however, the composite data shown in FIGS. 6A and B indicate that both the loss of large motor neurons and the effects of RK35 treatment on this loss are relatively subtle at the 12-week (88 day) age interval.

By end-stage, motor neuron counts in both RK35-treated and PBS-treated SODG93A mice were significantly different from wild type control mice by both methods of analysis (FIGS. 6C and D). These data are consistent with data on skeletal muscle structure and function presented above that the RK35-mediated improvements observed during early-stage disease are not maintained at end-stage.

Example 4

Discussion

ALS is a fatal and progressive disease in which motor neurons of the spinal cord and brain stem degenerate with subsequent muscle atrophy. Considerable attention has focused on mechanisms involved in motor neuron cell death.

Several recent studies have suggested that multiple cell types may be involved in the etiology of the disease by controlling the production of key factors in the extracellular microenvironment of the neuromuscular junction (Bruijn et al. (2004) *Annu. Rev. Neurosci.* 27:723-49). Studies using chimeric mice have shown that the presence of wild type nonneuronal cells can extend survival of motor neurons expressing mutant SOD1 (Clement et al. (2003) *Science* 302:113-17). These observations have led to the investigation of therapies that might slow neuronal degeneration by providing an optimal microenvironment for survival. For example, administration into muscle of virally expressed growth factors including IGF-1, GDNF and VEGF have all been shown to prolong survival in the SODG93A mouse model (Kaspar et al. (2003) *Science* 301:839-42; Azzouz et al. (2004) *Nature* 429:413-17; Wang et al (2002) *J. Neurosci.* 22:6920-28). Furthermore, muscle-specific expression of IGF-1 has been shown to stabilize neuromuscular junctions, enhance motor neuron survival, and delay onset and progression of disease in the SODG93A transgenic mouse model, indicating that direct effects on muscle can impact disease onset and progression (Dobrowolny et al. (2005) *J. Cell. Biol.* 168:193-99). Changes in muscle metabolism and motor neuron vulnerability have also been reported in ALS mice, further supporting the hypothesis that muscle may be an active driver of disease pathology (Dupois et al. (2004) *Proc. Natl. Acad. Sci. USA* 101:111159-64).

Myostatin, or GDF-8, is an endogenous inhibitor of muscle growth, eliciting its biological function, at least in part, by activation of the Activin IIb receptor (ActRIIb), resulting in repression of myoblast cell proliferation and differentiation (Langley et al. (2002) *J. Biol. Chem.* 277:49831-40; Thomas et al. (2000) *J. Biol. Chem.* 275:40235-43). Inhibition of GDF-8 function using anti-GDF-8 neutralizing antibodies has been shown to enhance muscle mass and strength in healthy adult mice as well as provide functional improvement in the mdx mouse model of muscular dystrophy (Whittemore et al. (2003) *Biochem. Biophys. Res. Commun.* 300:965-71; Bogdanovich et al. (2002) *Nature* 420:418-21). To better understand the role of muscle in motor neuron disease progression, a novel neutralizing antibody to GDF-8, RK35, which binds with higher affinity than a previously described reagent ($IC_{50}$ 3 nM for RK35 vs. >100 nM for JA16; Whittemore et al. (2003) *Biochem. Biophys. Res. Commun.* 300:965-71; Bogdanovich et al. (2002) *Nature* 420:418-21) was used, resulting in greater increases in muscle mass in wild type mice treated with RK35 (data not shown).

In SODG93A mouse and rat models of familial ALS, treatment with RK35 resulted in increased body weight and increased muscle mass and strength during the early phases of motor neuron disease. This early phase of disease is defined as the age (56-88 days after birth) at which SODG93A mice show a significant loss of muscle strength, as measured by grip strength assessment (Ligon et al. (2005) *Neuroreport* 16:533-36) and gait abnormalities (Wooley et al. (2005) *Muscle Nerve* 32:43-50), and which coincides with the denervation of neuromuscular junctions (Frey et al. (2000) *J. Neurosci.* 20:2534-42; Fischer et al (2004) *Experimental Neurology* 185:232-40). Muscle mass increases resulting from GDF-8 inhibition by RK35 were most evident in the quadriceps muscles, but were also pronounced in the gastrocnemius, cranial tibialis and the diaphragm in both rodent models tested. These increases correlated well with increased strength, as hindlimb and forelimb strength declined more slowly in RK35-treated mice in comparison to controls. The extent of muscle mass increase induced by treatment with the RK35 anti-GDF-8 antibody was similar in magnitude to a 25% increase in muscle mass observed in mice heterozygous for disruption of the GDF-8 gene; muscle mass from mice that are homozygous null for GDF-8 is about two-fold that of wild type mice (McPherron (1997) *Nature* 387:83-90).

At approximately 84-88 days after birth in SODG93A mice, and approximately 110 days for SODG93A rats, overt signs of disease including body weight decreases, gait abnormalities and paralysis become evident. RK35 treatment did not extend survival in either SODG93A mice or rats. The increased muscle mass and strength induced by anti-GDF-8 treatment in the early phase of disease did not delay the appearance of gait abnormalities and limb paralysis in both SODG93A mice and rats (data not shown), nor were gains in leg muscle mass maintained.

However significant increases in diaphragm mass in RK35-treated SODG93A mice and rats as compared to vehicle-treated SODG93A controls in both early and end-stage disease phases were observed. Diaphragm muscle in RK35-treated SODG93A mice at end-stage was comparable to that of age-matched wild type controls in both mass and histological evaluation. RK35-treated SODG93A rats also maintained a significant increase in diaphragm muscle mass at end-stage. Consistent with these morphological changes, electrophysiological analysis of diaphragms from untreated SODG93A rats indicates that expression of mutant SOD 1 results in significant inhibition of muscle function, and that treatment with RK35 effectively preserved muscle function in the diaphragm.

In this study a defined endpoint (failure of the right reflex test, indicating significant limb paralysis) was used, as the criteria for "end-stage" and euthanasia. Therefore it is not clear whether the enhanced diaphragm muscle mass, decreased atrophy, and improved electrophysiological function induced by RK35 treatment would have resulted in prolonged lifespan in rodents provided with nutritional supplementation. However, these findings are potentially important given the fact that respiratory dysfunction is the leading cause of death in patients with ALS (Lechtzin et al. (2002) *Amyotroph. Lateral Scler. Other Motor Neuron Disord* 3:5-13). Treatments such as RK35 designed to enhance diaphragm function may have the potential to delay the necessity for mechanically assisted breathing in ALS patients.

GDF-8 inhibition by RK35 may influence motor neuron loss in the lumbar spinal cord in the early disease phase, although many therapeutic benefits apparently were lost by end-stage disease. These data indicate that therapies acting directly on muscle can have a benefit on motor neurons innervating muscle, possibly by modulating the trophic microenvironment, although this approach is apparently not sufficient to delay disease. These observations are therefore consistent with the results of Dobrowolny et al. ((2005) *J. Cell. Biol.* 168:193-99), in which expression of a muscle-specific isoform of IGF led to slowed loss of motor neurons in the SODG93A mouse model, and that of Kaspar et al. ((2003) *Science* 301:839-42), where viral delivery of IGF1 to muscle resulted in reduced motor neuron loss in early-stage disease. Similar to the observations of Kaspar et al. ((2003), supra), beneficial effects of treatment on motor neuron survival were not maintained through end-stage disease. Improved trophic factor support from muscle is therefore likely to be insufficient to prevent motor neuron loss in the SODG93A model.

In summary, in both mouse and rat models of familial ALS, inhibition of myostatin results in enhanced muscle mass and strength, which is maintained through the early stages of disease but lost by end-stage. Myostatin inhibition slowed degenerative changes in skeletal muscle in early-stage disease, but did not delay onset of paralysis nor extend survival, as defined by right reflex failure, nor did myostatin inhibition significantly slow motor neuron loss. However, both morphological and functional differences through late-stage disease were observed in the diaphragm muscle of animals treated with anti-myostatin antibody, in comparison to untreated controls. Overall, the data provided herein support the potential for a beneficial effect of muscle building by treatment with RK35, which may contribute to an enhanced "quality of patient life" early in the disease process. Given that anti-GDF-8 antibodies are currently in clinical development, use of such clinical reagents in ALS for the maintenance of limb and diaphragm muscle mass warrants further investigation as a component of a multi-pronged approach to the treatment of ALS. The combination of an antiGDF-8 therapy with existing drugs such as the glutamate-antagonist riluzole, or newer agents entering clinical development, might not only improve the level of efficacy by helping maintain muscle mass but also have significant impact on overall patient quality of life.

Example 5

Mapping of Epitopes for RK35

In order to map the exact antibody epitopes to GDF-8, 48 overlapping 13-residue peptides representing the entire sequence of mature GDF-8 set forth in SEQ ID NO: 1 were synthesized directly on cellulose paper using the spot synthesis technique (e.g., Molina et al. (1996) *Peptide Res.* 9:151-55; Frank et al. (1992) *Tetrahedron* 48:9217-32). The overlap of the peptides was 11 amino acids. In this array, cysteine residues were replaced with serine in order to reduce the chemical complications caused by cysteines. Cellulose membranes modified with polyethylene glycol and Fmoc-protected amino acids were purchased from Abimed (Lagenfeld, Germany). The array was defined on the membrane by coupling a β-alanine spacer, and peptides were synthesized using standard DIC (diisopropylcarbodiimide)/HOBt (hydroxybenzotriazole) coupling chemistry as described previously (Molina et al., supra; Frank et al., supra).

Activated amino acids were spotted using an Abimed ASP 222 robot. Washing and deprotection steps were done manually, and the peptides were N-terminally acetylated after the final synthesis cycle. Following peptide synthesis, the membrane was washed in methanol for 10 minutes and in blocker (TBST (Tris-buffered saline with 0.1% (v/v) Tween™ 20) and 1% (w/v) casein) for 10 minutes. The membrane was then incubated with 2.5 µg/ml of an anti-GDF-8 antibody in blocker for 1 hr with gentle shaking. After washing in blocker 3 times for 10 min, the membrane was incubated with HRP-labeled secondary antibody (0.25 µg/ml in blocker) for 30 min. The membrane was then washed three times for 10 min each with blocker and 2 times for 10 minutes each with TBST. Bound antibody was visualized using SuperSignal™ West reagent (Pierce) and a digital camera (Alphananotech Fluoromager). As shown in FIG. 7, the RK35 epitope maps to a region of GDF-8 between amino acids 30-40 and 84-97, that putatively interacts with the GDF-8 Type II receptor as predicted by GDF-8 receptor sequence comparison with homologous TGF-β family receptors with characterized domains.

Example 6

Characterizing the RK35 Antibody

The variable heavy (VH) and variable light (VL) genes encoding RK35 were cloned from hybridoma cells producing the antibody, and the amino acid sequences were determined. Sequence data for the RK35 antibody was used to identify the nearest germline sequence for the heavy and light chain. A comparison of RK35 light and heavy variable regions with the closest human germline sequences is shown in FIG. 8. Appropriate mutations may be made using standard site-directed mutagenesis techniques with the appropriate mutagenic primers. Mutation of the antibody is then confirmed by sequence analysis. Exemplary amino acid sequences for humanized RK35 are set forth in SEQ ID NOs:7 (VH) and 9 (VL), both of which may be encoded by a nucleic acid sequence readily determined by a skilled artisan, e.g., the nucleic acid sequences set forth as SEQ ID NO:6 (VH) and 8 (VL). A skilled artisan will recognize that any and/or all amino acids in the framework of the humanized antibody may be mutated back to the original murine amino acid, e.g., to maintain the conformation of the antigen binding fragment. Nonlimiting examples of SEQ ID NO:7 (VH) and SEQ ID NO:9 (VL) with some back-mutations that may help to maintain the affinity of the antibody to GDF-8 are set forth as SEQ ID NO:26 and SEQ ID NO:27, respectively.

To create chimeric antibodies, the VH sequence is subcloned into a pED6 huIgG1 mut expression vector, which encodes human IgG1 containing two point mutations (L234A and G237A) to reduce binding to human Fc receptors and complement components (Morgan et al. (1995) *Immunology* 86:319-24; Shields et al (2001) *J. Biol. Chem.* 276:6591-604). The VL sequence of RK35 may be subcloned into the pED6 Kappa expression vector. The expression vectors containing the RK35 VH and VL sequences are then cotransfected into COS-1 cells and a chimeric RK35 antibody is purified from conditioned medium.

Example 7

Treatment of Muscle Disorders

Inhibitors of GDF-8, i.e., GDF-8 antagonists, such as, for example, inhibitory antibodies, are useful for treatment of metabolic disorders associated with GDF-8 such as type 2 diabetes, impaired glucose tolerance, metabolic syndrome (e.g., syndrome X), insulin resistance (e.g., induced by trauma such as burns or nitrogen imbalance), and adipose tissue disorders (e.g., obesity). Inhibitors of GDF-8 are also useful for the treatment of bone and muscle disorders associated with GDF-8, such as ALS, muscular dystrophy and osteoarthritis. The anti-GDF-8 antibodies and antibody fragments of the invention may be used to treat a subject, e.g., a human subject, preferably a subject suffering from ALS, at disease onset, or a subject having an established metabolic or bone/muscular disease. The inhibitory antibodies against GDF-8 may also be used to prevent and/or to reduce the severity and/or the symptoms of the disease. It is anticipated that the anti-GDF-8 antibodies and antibody fragments are administered, e.g., subcutaneously, as frequently as once per day and as infrequently as once per month. Treatment durations range from about one month (or less) to several years.

To test the clinical efficacy of anti-GDF-8 in humans, subjects suffering from or at risk for ALS are identified and randomized to treatment groups. Treatment groups include a placebo group and one to three or more groups receiving antibody (at different doses when there are two or more groups). Individuals are followed prospectively for, e.g., one month to three years to assess changes in weight, muscle mass, and grip strength. It is anticipated that individuals receiving treatment will exhibit an improvement.

A GDF-8 antagonist, preferably in the form of an antibody or antibodies, is administered as the sole active compound or in combination with another compound or composition. When administered as the sole active compound or in combination with another compound or composition, the dosage is preferably from approximately 1 µg/kg to 100 mg/kg, depending on the severity of the symptoms and/or the progression of the disease. The appropriate effective dose may be selected by a treating clinician from the following nonlimiting list of ranges: 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg to 1 mg/kg, and 500 µg/kg to 1 mg/kg. Exemplary nonlimiting treatment regimens and potential outcomes are summarized in Table 5.

TABLE 5

Examples of Potential Clinical Cases

| Status prior to treatment | Treatment Regimen | Potential Outcome |
|---|---|---|
| No clinical signs, family history of ALS | 0.01-1 mg/kg every 4 weeks for 48 weeks | Prevention of ALS or delay of onset |
| Mild clinical signs of ALS | 0.01-100 mg/kg weekly for 4 or more weeks | Improved grip strength, weight gain, and muscle mass |
| Advanced stage of ALS characterized by severe muscle wasting, weight loss, and loss of strength, etc. | 0.01-100 mg/kg twice weekly for 6 or more weeks | Improvement of clinical signs, reduction in severity of symptoms and/or increase in muscle mass/body fat ratio |

The specification is most thoroughly understood in light of the teachings of the references cited within the specification, all of which are hereby incorporated by reference herein in their entireties. The embodiments within the specification provide illustrations of the invention and should not be construed to limit the scope of the invention. The skilled artisan recognizes that many other embodiments are encompassed by the claimed invention, and that the specification and examples should be considered as exemplary only.

What is claimed is:

1. A method for increasing muscle mass in a mammal comprising administering a therapeutically effective amount of an antibody selected from the group consisting of:
   (a) an isolated antibody capable of binding GDF-8 comprising a heavy chain variable region comprising three complementarity determining regions (CDRs) comprising the amino acid sequences of SEQ ID NO: 10, SEQ ID NO: 11, and SEQ ID NO: 12, and a light chain variable region comprising three CDRs comprising the amino acid sequences of SEQ ID NO: 13, SEQ ID NO: 14, and SEQ ID NO: 15; and
   (b) an isolated antibody capable of binding GDF-8 comprising the amino acid sequences of SEQ ID NO: 10, SEQ ID NO: 11, SEQ ID NO: 12, SEQ ID NO: 13, SEQ ID NO: 14, and SEQ ID NO: 15,
   thereby increasing muscle mass in the mammal.

2. A method for treating or ameliorating amyotrophic lateral sclerosis (ALS) in a mammal comprising administering a therapeutically effective amount of an antibody selected from the group consisting of:
   (a) an isolated antibody capable of binding GDF-8 comprising a heavy chain variable region comprising three complementarity determining regions (CDRs) comprising the amino acid sequences of SEQ ID NO: 10, SEQ ID NO: 11, and SEQ ID NO: 12, and a light chain variable region comprising three CDRs comprising the amino acid sequences of SEQ ID NO: 13, SEQ ID NO: 14, and SEQ ID NO: 15; and
   (b) an isolated antibody capable of binding GDF-8 comprising the amino acid sequences of SEQ ID NO: 10, SEQ ID NO: 11, SEQ ID NO: 12, SEQ ID NO: 13, SEQ ID NO: 14, and SEQ ID NO: 15
   thereby treating or ameliorating ALS in a mammal.

3. The method of any of claims 1-2, wherein said heavy chain variable region comprises a CDR 1 comprising the amino acid sequence of SEQ ID NO: 10, a CDR 2 comprising the amino acid sequence of SEQ ID NO: 11, and a CDR 3 comprising the amino acid sequence of SEQ ID NO: 12, and said light chain variable region comprises a CDR1 comprising the amino acid sequence of SEQ ID NO: 13, a CDR2 comprising the amino acid sequence of SEQ ID NO: 14, and a CDR3 comprising the amino acid sequence of SEQ ID NO: 15.

4. The method of claim 3, wherein the antibody comprises a heavy chain variable region comprising an amino acid sequence selected from the group consisting of the amino acid sequence of SEQ ID NO: 3, and the amino acid sequence of SEQ ID NO:7, and a light chain variable region comprising an amino acid sequence selected from the group consisting of the amino acid sequence of SEQ ID NO: 5, and the amino acid sequence of SEQ ID NO: 9.

5. The method of claim 4, wherein the antibody is selected from the group consisting of:
   a) an antibody comprising a heavy chain variable region comprising the amino acid sequence of SEQ ID NO: 7, and a light chain variable region comprising the amino acid sequence of SEQ ID NO: 9;
   b) an antibody comprising a heavy chain variable region comprising the amino acid sequence of SEQ ID NO: 3, and a light chain variable region comprising the amino acid sequence of SEQ ID NO: 5;
   c) an antibody comprising a heavy chain variable region comprising the amino acid sequence of SEQ ID NO: 7, and a light chain variable region comprising the amino acid sequence of SEQ ID NO: 5; and
   d) an antibody comprising a heavy chain variable region comprising the amino acid sequence of SEQ ID NO: 3, and a light chain variable region comprising the amino acid sequence of SEQ ID NO: 9.

6. The method of any of claims 1-2, wherein said antibody comprises a heavy chain variable region comprising the amino acid sequence of SEQ ID NO: 7, and a light chain variable region comprising the amino acid sequence of SEQ ID NO: 9.

7. The method of any of claims 1-2, wherein the antibody comprises a heavy chain variable region comprising the amino acid sequence of SEQ ID NO: 3; and a light chain variable region comprising the amino acid sequence of SEQ ID NO: 5.

8. The method of any of claims 1-2, wherein the antibody is a monoclonal antibody.

9. The method of any of claims 1-2, wherein the antibody is a humanized monoclonal antibody.

10. The method of claim 3, wherein the antibody is a monoclonal antibody or a humanized monoclonal antibody.

11. The method of claim 4, wherein the antibody is a monoclonal antibody or a humanized monoclonal antibody.

12. The method of claim 5, wherein the antibody is a monoclonal antibody or a humanized monoclonal antibody.

13. The method of claim 6, wherein the antibody is a monoclonal antibody or a humanized monoclonal antibody.

14. The method of claim 7, wherein the antibody is a monoclonal antibody or a humanized monoclonal antibody.

* * * * *

SEQUENCE LISTING

<160> NUMBER OF SEQ ID NOS: 34

<210> SEQ ID NO 1
<211> LENGTH: 109
<212> TYPE: PRT
<213> ORGANISM: Homo sapiens

<400> SEQUENCE: 1

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 2
<211> LENGTH: 348
<212> TYPE: DNA
<213> ORGANISM: Mus musculus

<400> SEQUENCE: 2
gaagtgcagc tggtggagtc tgggggaggc ttagtgaagc ctggagggtc cctgaaactc      60
tcctgtgcag cctctggatt cactttcagt agctatgcca tgtcttgggt tcgccagact     120
ccggagaaga ggctggagtg ggtcgcaacc attagtagtg gtggtagtta cacctcctat     180
ccagacagtg tgaagggtcg attcaccatc tccagagaca atgccaagaa cacactgtac     240

```
ctgcaaatga gcagtctgag gtctgaggac acggccatgt attactgtgc aagacaagac    300
tatgctatga actactgggg tcaaggaacc tcagtcaccg tctcctca                 348
```

<210> SEQ ID NO 3
<211> LENGTH: 116
<212> TYPE: PRT
<213> ORGANISM: Mus musculus

<400> SEQUENCE: 3

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Asp Tyr Ala Met Asn Tyr Trp Gly Gln Gly Thr Ser Val
            100                 105                 110

Thr Val Ser Ser
        115
```

<210> SEQ ID NO 4
<211> LENGTH: 321
<212> TYPE: DNA
<213> ORGANISM: Mus musculus

<400> SEQUENCE: 4

```
gacattgaga tgacccagtc tcacaaattc atgtccacat cagtaggaga cagggtcagc    60
atcacctgca aggccagtca ggatgtgagt actgctgtag cctggtatca acagaaacca   120
ggacaatctc ctaaaactact gctttactcg gcatcctacc ggtacactgg agtccctgat   180
cggttcactg gcagtggatc tgggacggat ttcactttca ccatcagcag tgtgcaggct   240
gaagacctgg cagtttatta ctgtcagcaa cattatagta ctccgtggac gttcggtgga   300
ggcaccaagc tggaaatcaa a                                             321
```

<210> SEQ ID NO 5
<211> LENGTH: 107
<212> TYPE: PRT
<213> ORGANISM: Mus musculus

<400> SEQUENCE: 5

```
Asp Ile Glu Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Leu
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
```

```
                      85                  90                  95
Thr Phe Gly Gly Gly Thr Lys Leu Glu Ile Lys
                 100                 105

<210> SEQ ID NO 6
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaggtccaac tattagaatc gggaggcggt ctggttcagc caggagggag tctcaggctt      60
agttgcgctg cgtcgggatt cacctttca agttacgcaa tgtcatgggt cgtcaggca      120 ccggggaaag gcttagagtg ggtgtcaact attagctctg gcggtagcta tacgtcgtat    180
cctgactctg tgaagggacg atttacaata agccgggaca attctaaaaa cactttgtac    240
ctacagatga attccttgag agccgaagat accgccgtct actattgtgc gaagcaagat    300
tacgctatga actattgggg tcaagggaca atggtaacgg tatcctcc                 348

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Tyr Ala Met Asn Tyr Trp Gly Gln Gly Thr Met Val
            100                 105                 110

Thr Val Ser Ser
        115

<210> SEQ ID NO 8
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gacattcaaa tgacccaaag cccttcttcc ttaagcgcat cagtaggtga ccgagttaca     60
ataacgtgta aagcgagcca agatgtgagt actgcagtag cgtggtatca gcaaaagcca    120
gggaaggctc cgaaactatt gatttactcc gcctcttaca gatatacggg cgttcctgat    180
```

```
aggtttagtg gaagtgggtc gggtacggac tttaccctga ctatatcgtc acttcagcca    240
gaggattttg ctacctacta ttgccaacag cattattcaa caccgtggac attcggccag    300
ggaactaagg tcgaaataaa a                                              321
```

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105
```

<210> SEQ ID NO 10
<211> LENGTH: 5
<212> TYPE: PRT
<213> ORGANISM: Mus musculus

<400> SEQUENCE: 10

```
Ser Tyr Ala Met Ser
1               5
```

<210> SEQ ID NO 11
<211> LENGTH: 17
<212> TYPE: PRT
<213> ORGANISM: Mus musculus

<400> SEQUENCE: 11

```
Thr Ile Ser Ser Gly Gly Ser Tyr Thr Ser Tyr Pro Asp Ser Val Lys
1               5                   10                  15

Gly
```

<210> SEQ ID NO 12
<211> LENGTH: 7
<212> TYPE: PRT
<213> ORGANISM: Mus musculus

<400> SEQUENCE: 12

```
Gln Asp Tyr Ala Met Asn Tyr
1               5
```

<210> SEQ ID NO 13
<211> LENGTH: 11
<212> TYPE: PRT
<213> ORGANISM: Mus musculus

<400> SEQUENCE: 13

```
<210> SEQ ID NO 13 (continued)

Lys Ala Ser Gln Asp Val Ser Thr Ala Ala
1               5                   10

<210> SEQ ID NO 14
<211> LENGTH: 7
<212> TYPE: PRT
<213> ORGANISM: Mus musculus

<400> SEQUENCE: 14

Ser Ala Ser Tyr Arg Tyr Thr
1               5

<210> SEQ ID NO 15
<211> LENGTH: 7
<212> TYPE: PRT
<213> ORGANISM: Mus musculus

<400> SEQUENCE: 15

Gln Gln His Tyr Ser Thr Pro
1               5

<210> SEQ ID NO 16
<211> LENGTH: 321
<212> TYPE: DNA
<213> ORGANISM: Homo sapiens

<400> SEQUENCE: 16
cgaaccgtag cggcaccgtc agtattcata ttccctccat cggacgagca attgaaaagt      60
gggacagctt cggtcgtgtg tctcttgaat aacttttacc ccagagaagc taaggtccag     120
tggaaagttg acaatgcgtt acagagcgga aattctcaag aatccgttac tgaacaggat     180
agtaaggatt ctacgtattc acttagcagt actctgaccc tatcaaaggc agattatgaa     240
aaacacaagg tatacgcctg cgaggtgacg catcaaggct atccagccc agttacaaaa      300
tcttttaaca ggggtgagtg t                                                321

<210> SEQ ID NO 17
<211> LENGTH: 107
<212> TYPE: PRT
<213> ORGANISM: Homo sapiens

<400> SEQUENCE: 17

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 18
<211> LENGTH: 990
<212> TYPE: DNA
<213> ORGANISM: Homo sapiens
```

-continued

<400> SEQUENCE: 18

```
gcctccacaa aaggaccatc tgttttttccc ttggcgccat caagtaaatc tacttccgga      60
ggtaccgctg cgcttggctg cctcgtgaaa gactatttcc cagaacctgt cacagtctcg     120
tggaatagtg gtgctttaac ctcgggcgta catactttc ctgctgtact tcaatcaagc     180
ggactgtact cattatcgtc tgtagtcacg gtcccgagtt cttcactcgg aacacagact     240
tatatatgca acgttaatca taagcctagc aacaccaagg ttgacaaaaa ggtggaacca     300
aaatcgtgcg ataagacgca cacatgtcca ccctgtcctg caccagaagc tctgggcgcg     360
ccatcggttt tcttgttccc acccaaacct aaggacacgt taatgataag tcgaacgcca     420
gaggtgacat gtgttgtagt ggatgtgagc cacgaagatc cggaagtaaa attcaattgg     480
tatgtagatg gtgttgaagt ccataacgca aaaactaagc cgagggaaga gcagtacaac     540
tctacttata gggtagtctc cgtactaact gtcttgcacc aagattggct aaatgggaag     600
gaatataaat gtaaggtttc aaataaggca ctaccagccc cgatagagaa gacaataagc     660
aaagcgaagg ggcaaccaag agagccccaa gtgtacacct tgcctccgag cagagaggaa     720
atgacaaaaa atcaagtatc ccttacgtgt ctggtaaagg gattttatcc aagtgacata     780
gcagtggagt gggagagtaa cggccagcca gaaaacaatt acaaaaccac tcccccggtt     840
ttagatagcg atgggagttt cttttttgtac tcaaagttga ccgttgacaa gtcacgatgg     900
cagcaaggta atgtatttag ttgttctgtt atgcatgagg ccttacataa tcactacacg     960
cagaaatctc tctccttaag ccccgggaaa                                        990
```

<210> SEQ ID NO 19
<211> LENGTH: 330
<212> TYPE: PRT
<213> ORGANISM: Homo sapiens

<400> SEQUENCE: 19

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 10
<212> TYPE: PRT
<213> ORGANISM: Mus musculus

<400> SEQUENCE: 20

Gly Phe Thr Phe Ser Ser Tyr Ala Met Ser
1               5                   10

<210> SEQ ID NO 21
<211> LENGTH: 10
<212> TYPE: PRT
<213> ORGANISM: Mus musculus

<400> SEQUENCE: 21

Thr Ile Ser Ser Gly Gly Ser Tyr Thr Ser
1               5                   10

<210> SEQ ID NO 22
<211> LENGTH: 7
<212> TYPE: PRT
<213> ORGANISM: Mus musculus

<400> SEQUENCE: 22

Gln Asp Tyr Ala Met Asn Tyr
1               5

<210> SEQ ID NO 23
<211> LENGTH: 11
<212> TYPE: PRT
<213> ORGANISM: Mus musculus

<400> SEQUENCE: 23

Lys Ala Ser Gln Asp Val Ser Thr Ala Val Ala
1               5                   10

<210> SEQ ID NO 24
<211> LENGTH: 7
<212> TYPE: PRT
<213> ORGANISM: Mus musculus

<400> SEQUENCE: 24
```

```
Ser Ala Ser Tyr Arg Tyr Thr
1               5
```

<210> SEQ ID NO 25
<211> LENGTH: 7
<212> TYPE: PRT
<213> ORGANISM: Mus musculus
<400> SEQUENCE: 25

```
Gln Gln His Tyr Ser Thr Pro
1               5
```

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Glu Lys Arg Leu Glu Trp Val
        35                  40                  45

Ala Thr Ile Ser Ser Gly Gly Ser Tyr Thr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Lys Gln Asp Tyr Ala Met Asn Tyr Trp Gly Gln Gly Thr Met Val
            100                 105                 110

Thr Val Ser Ser
            115
```

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 27

```
Asp Ile Glu Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105
```

<210> SEQ ID NO 28
<211> LENGTH: 405
<212> TYPE: DNA
<213> ORGANISM: Mus musculus

<400> SEQUENCE: 28

| | | | | |
|---|---|---|---|---|
| atgaactttg tgctcagctt gattttcctt gccctcattt taaaaggtgt ccagtgtgaa | | | | 60 |
| gtgcagctgg tggagtctgg gggaggctta gtgaagcctg agggtccct gaaactctcc | | | | 120 |
| tgtgcagcct ctggattcac tttcagtagc tatgccatgt cttgggttcg ccagactccg | | | | 180 |
| gagaagaggc tggagtgggt cgcaaccatt agtagtggtg gtagttacac ctcctatcca | | | | 240 |
| gacagtgtga agggtcgatt caccatctcc agagacaatg ccaagaacac cctgtacctg | | | | 300 |
| caaatgagca gtctgaggtc tgaggacacg gccatgtatt actgtgcaag acaagactat | | | | 360 |
| gctatgaact actggggtca aggaacctca gtcaccgtct cctca | | | | 405 |

<210> SEQ ID NO 29
<211> LENGTH: 135
<212> TYPE: PRT
<213> ORGANISM: Mus musculus

<400> SEQUENCE: 29

Met Asn Phe Val Leu Ser Leu Ile Phe Leu Ala Leu Ile Leu Lys Gly
1               5                   10                  15
Val Gln Cys Glu Val Gln Leu Val Glu Ser Gly Gly Gly Leu Val Lys
            20                  25                  30
Pro Gly Gly Ser Leu Lys Leu Ser Cys Ala Ala Ser Gly Phe Thr Phe
        35                  40                  45
Ser Ser Tyr Ala Met Ser Trp Val Arg Gln Thr Pro Glu Lys Arg Leu
    50                  55                  60
Glu Trp Val Ala Thr Ile Ser Ser Gly Gly Ser Tyr Thr Ser Tyr Pro
65                  70                  75                  80
Asp Ser Val Lys Gly Arg Phe Thr Ile Ser Arg Asp Asn Ala Lys Asn
                85                  90                  95
Thr Leu Tyr Leu Gln Met Ser Ser Leu Arg Ser Glu Asp Thr Ala Met
            100                 105                 110
Tyr Tyr Cys Ala Arg Gln Asp Tyr Ala Met Asn Tyr Trp Gly Gln Gly
        115                 120                 125
Thr Ser Val Thr Val Ser Ser
    130                 135

<210> SEQ ID NO 30
<211> LENGTH: 381
<212> TYPE: DNA
<213> ORGANISM: Mus musculus

<400> SEQUENCE: 30

| | | | | |
|---|---|---|---|---|
| atggagtcac agattcaggt ctttgtattc gtgtttctct ggttgtctgg tgttgacgga | | | | 60 |
| gacattgaga tgacccagtc tcacaaattc atgtccacat cagtaggaga cagggtcagc | | | | 120 |
| atcacctgca aggccagtca ggatgtgagt actgctgtag cctggtatca acagaaacca | | | | 180 |
| ggacaatctc ctaaactact gctttactcg gcatcctacc ggtacactgg agtccctgat | | | | 240 |
| cggttcactg gcagtggatc tgggacggat ttcactttca ccatcagcag tgtgcaggct | | | | 300 |
| gaagacctgg cagtttatta ctgtcagcaa cattatagta ctccgtggac gttcggtgga | | | | 360 |
| ggcaccaagc tggaaatcaa a | | | | 381 |

<210> SEQ ID NO 31
<211> LENGTH: 127
<212> TYPE: PRT
<213> ORGANISM: Mus musculus

<400> SEQUENCE: 31

Met Glu Ser Gln Ile Gln Val Phe Val Phe Val Phe Leu Trp Leu Ser
1               5                   10                  15

Gly Val Asp Gly Asp Ile Glu Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Lys Leu Leu Leu Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Ser Thr Pro Trp Thr Phe Gly Gly Gly Thr Lys Leu Glu Ile Lys
        115                 120                 125

<210> SEQ ID NO 32
<211> LENGTH: 95
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 33
<211> LENGTH: 98
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95
Ala Lys

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Gly Gly Ser Gly Gly Gly Gly Ser Gly Gly Gly Gly Ser
1               5                   10                  15
```